United States Patent
Moreno

(10) Patent No.: US 11,900,603 B2
(45) Date of Patent: Feb. 13, 2024

(54) SYSTEMS AND METHODS FOR WHOLE-BRAIN CIRCUIT-BASED NEUROSTIMULATION TO TREAT BRAIN DISORDERS

(71) Applicant: Neurotherapeutix, LLC, Hopewell Junction, NY (US)

(72) Inventor: Marta Moreno, Hopewell Junction, NY (US)

(73) Assignee: Neurotherapeutix, LLC, Hopewell Junction, NY (US)

( * ) Notice: Subject to any disclaimer, the term of this patent is extended or adjusted under 35 U.S.C. 154(b) by 0 days.

(21) Appl. No.: 18/338,221

(22) Filed: Jun. 20, 2023

(65) Prior Publication Data

US 2023/0419484 A1  Dec. 28, 2023

Related U.S. Application Data

(63) Continuation of application No. PCT/US2023/068688, filed on Jun. 19, 2023.

(60) Provisional application No. 63/354,451, filed on Jun. 22, 2022, provisional application No. 63/383,241, filed on Nov. 10, 2022.

(51) Int. Cl.
*A61N 2/00* (2006.01)
*G06T 7/00* (2017.01)
*G01R 33/563* (2006.01)
*G01R 33/48* (2006.01)

(52) U.S. Cl.
CPC ........... *G06T 7/0012* (2013.01); *A61N 2/006* (2013.01); *G01R 33/4806* (2013.01); *G01R 33/56341* (2013.01); *G06T 2207/10088* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 2015/0119689 A1* | 4/2015 | Pascual-Leone | A61N 2/006 600/407 |
| 2020/0107777 A1 | 4/2020 | Javitt et al. | |
| 2020/0275838 A1 | 9/2020 | Javitt et al. | |
| 2022/0044404 A1* | 2/2022 | Sughrue | G16H 70/00 |

OTHER PUBLICATIONS

Liston et al., "Default Mode Network Mechanisms of Transcranial Magnetic Stimulation in Depression," Biol. Psychiatry, Oct. 2014; 76(7): 517-526 (Year: 2014).*
Glasser et al., "The Minimal Preprocessing Pipelines for the Human Connectome Project," Neuroimage, 80:105-124 (Oct. 15, 2013).
Glasser et al., "A multi-modal parcellation of human cerebral cortex", Nature, 536(7615):171-178 (Aug. 11, 2016).

(Continued)

*Primary Examiner* — Thaddeus B Cox
(74) *Attorney, Agent, or Firm* — Fox Rothschild LLP

(57) ABSTRACT

Targeted and individualized methods are provided herein for determining specific treatment sites based on an individual patient. Embodiments described herein may use functional and/or structural connections to create brain mapping of the patient and/or control groups having the same metrics as the patient, and combinations thereof in determining target locations for stimulation treatment.

14 Claims, 22 Drawing Sheets

(56) References Cited

OTHER PUBLICATIONS

Fox et al., "Efficacy of transcranial magnetic stimulation targets for depression is related to intrinsic functional connectivity with the subgenual cingulate", Biol Psychiatry 2012;72:595-603.

* cited by examiner

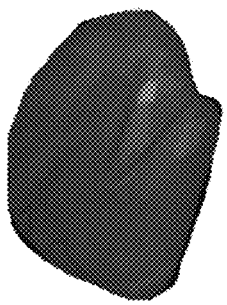 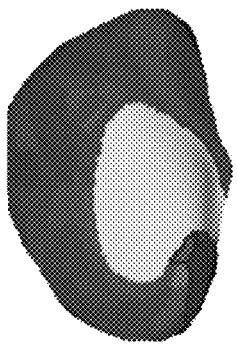 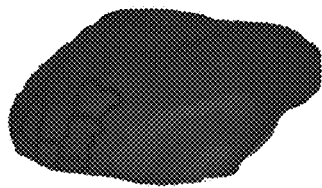
FIG. 10D  FIG. 10E  FIG. 10F
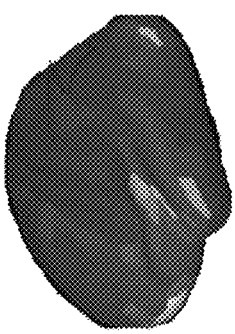 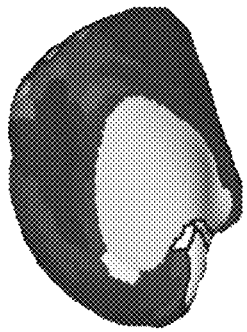 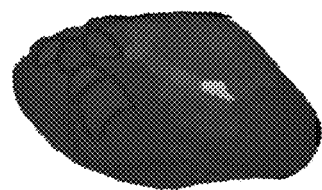
FIG. 10A  FIG. 10B  FIG. 10C
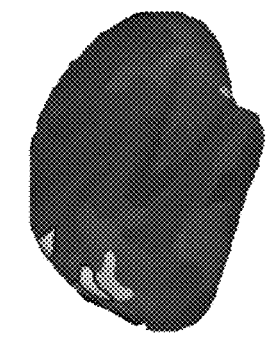 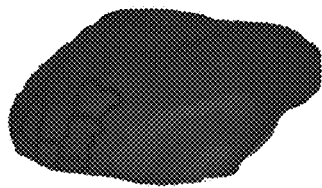 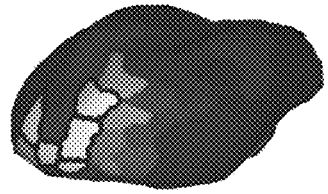
FIG. 9D  FIG. 9E  FIG. 9F
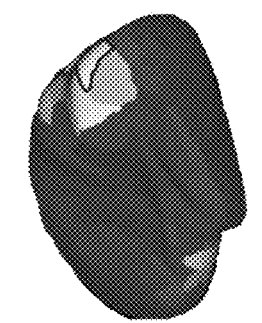 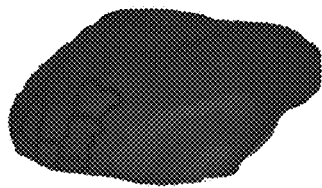 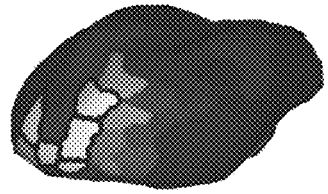
FIG. 9A  FIG. 9B  FIG. 9C

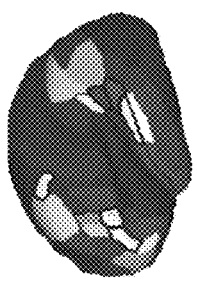
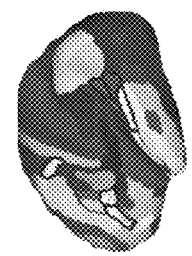
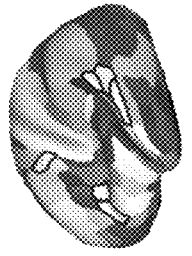
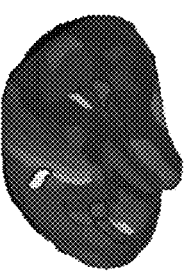
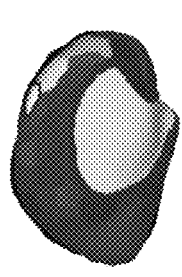
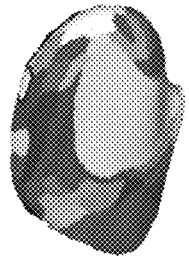
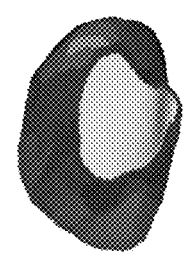
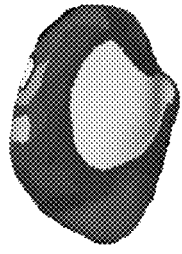
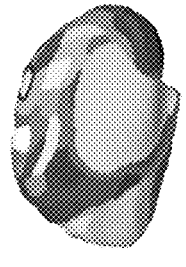
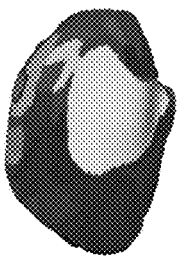
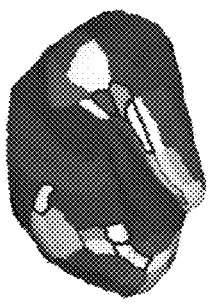
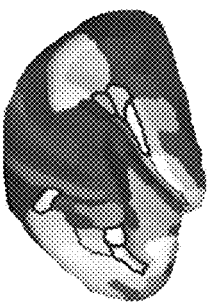
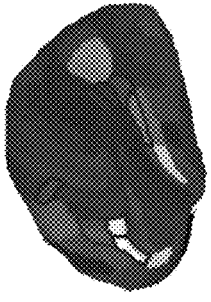

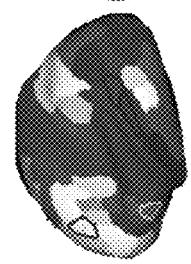
FIG. 34A
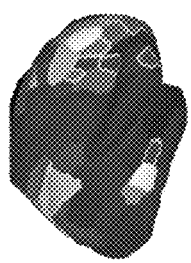
FIG. 34C
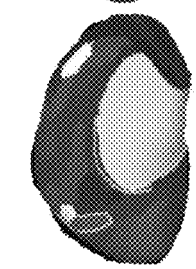
FIG. 34B
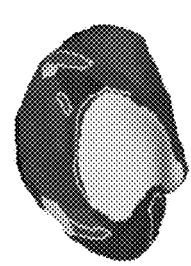
FIG. 34D
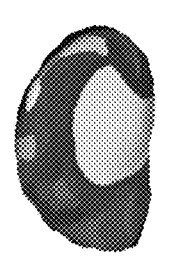
FIG. 37A
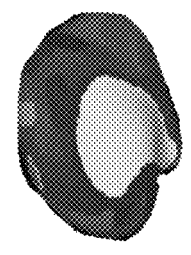
FIG. 37C
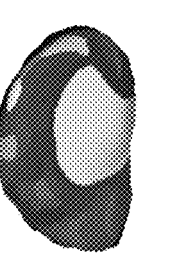
FIG. 37B
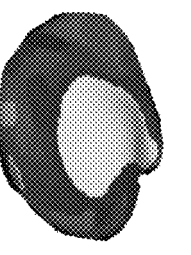
FIG. 37D
FIG. 33A
FIG. 33C
FIG. 33B
FIG. 33D
FIG. 36A
FIG. 36C
FIG. 36B
FIG. 36D
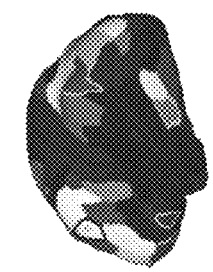
FIG. 32A
FIG. 32C
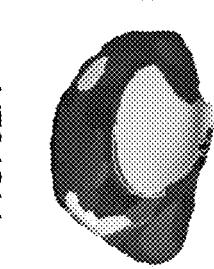
FIG. 32B
FIG. 32D
FIG. 35A
FIG. 35C
FIG. 35B
FIG. 35D

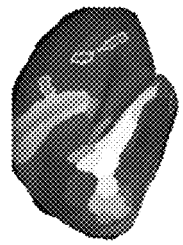 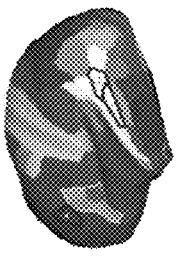 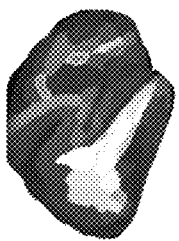  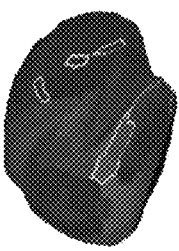 
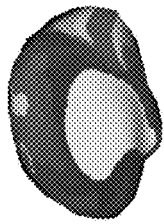 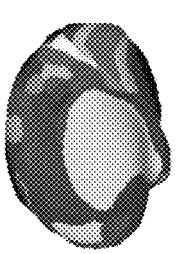 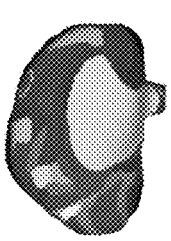 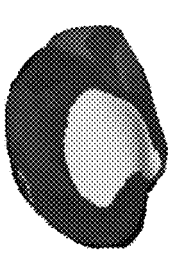 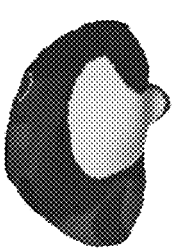
    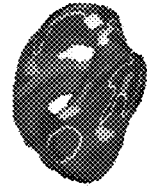  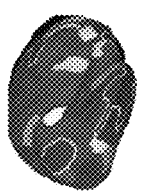 

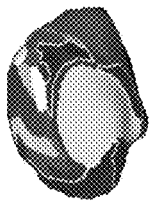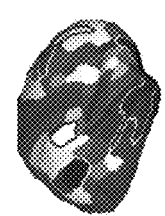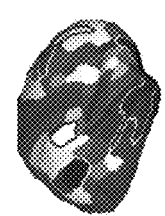
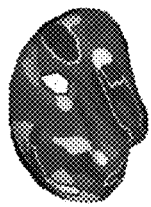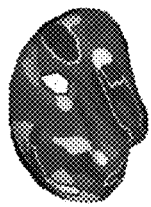
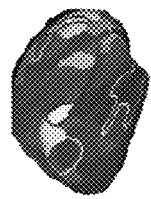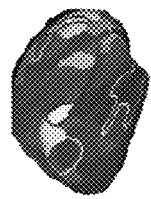
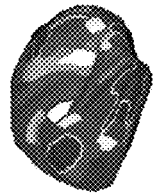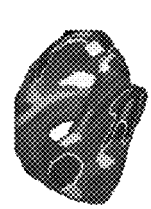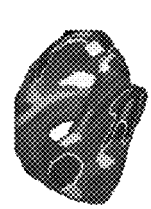
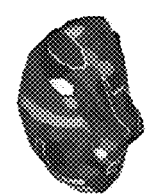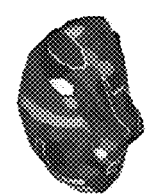
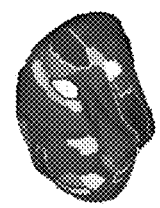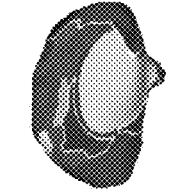
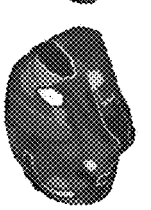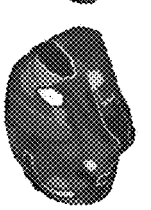
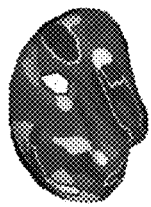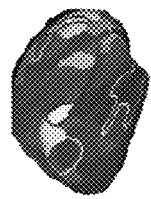
FIG. 45A FIG. 45B FIG. 45C FIG. 45D
FIG. 46A FIG. 46B FIG. 46C FIG. 46D
FIG. 47A FIG. 47B FIG. 47C FIG. 47D
FIG. 48A FIG. 48B FIG. 48C FIG. 48D
FIG. 49A FIG. 49B FIG. 49C FIG. 49D
FIG. 50A FIG. 50B FIG. 50C FIG. 50D
FIG. 51A FIG. 51B FIG. 51C FIG. 51D
FIG. 52A FIG. 52B FIG. 52C FIG. 52D FIG. 53A
FIG. 53B
FIG. 53C
FIG. 53D
FIG. 54A
FIG. 54B
FIG. 54C
FIG. 54D
FIG. 55A
FIG. 55B
FIG. 55C
FIG. 55D
FIG. 56A
FIG. 56B
FIG. 56C
FIG. 56D
FIG. 57A
FIG. 57B
FIG. 57C
FIG. 57D
FIG. 58A
FIG. 58B
FIG. 58C
FIG. 58D
FIG. 59A
FIG. 59B
FIG. 59C
FIG. 59D

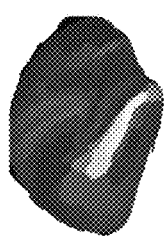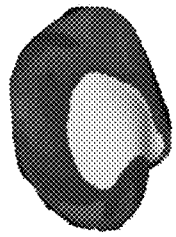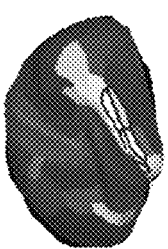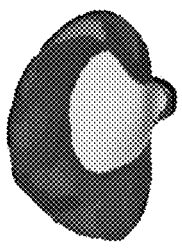
FIG. 62C  FIG. 62D
FIG. 62A  FIG. 62B
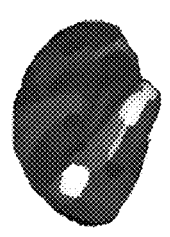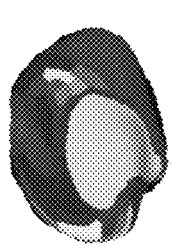
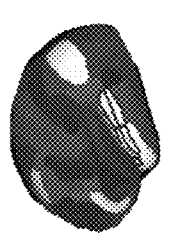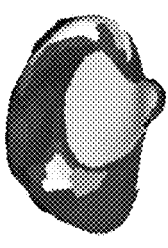
FIG. 65C  FIG. 65D
FIG. 65A  FIG. 65B
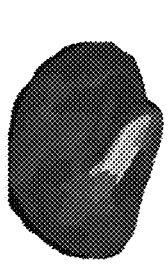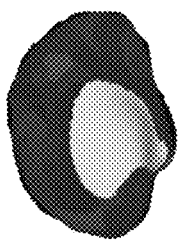
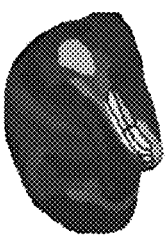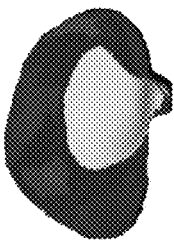
FIG. 61C  FIG. 61D
FIG. 61A  FIG. 61B
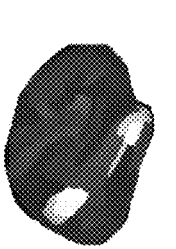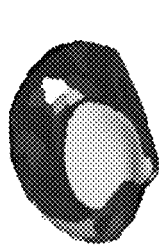
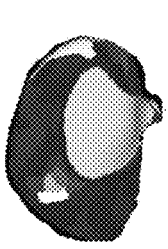
FIG. 64C  FIG. 64D
FIG. 64A  FIG. 64B
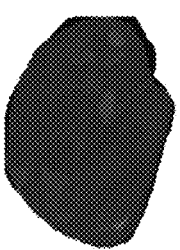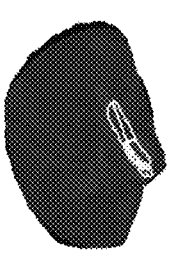
FIG. 60C  FIG. 60D
FIG. 60A  FIG. 60B
FIG. 63C  FIG. 63D
FIG. 63A  FIG. 63B

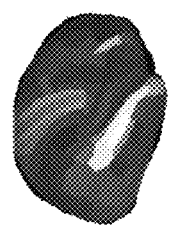
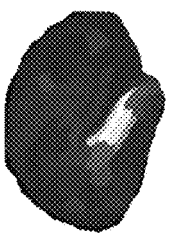
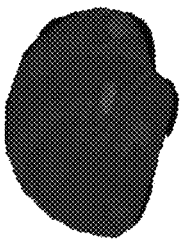
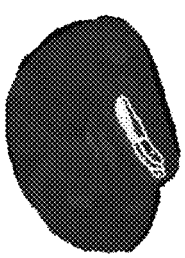
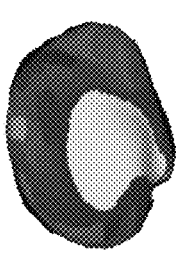
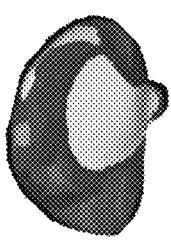
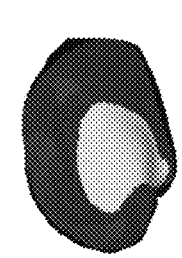
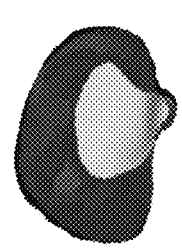
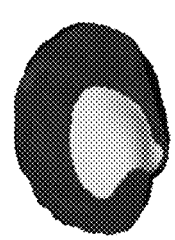
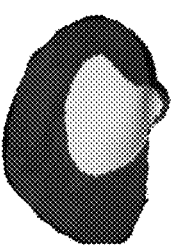
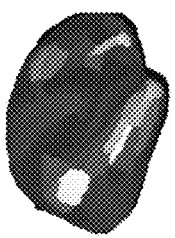
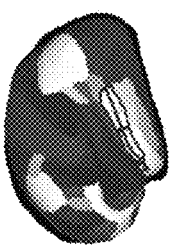
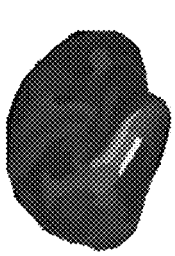
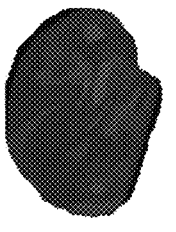
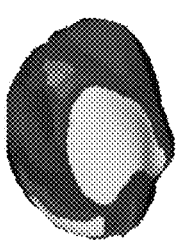
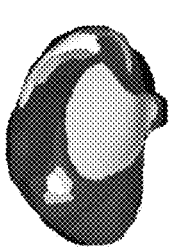
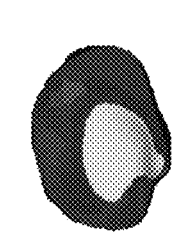
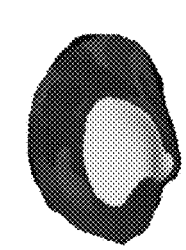

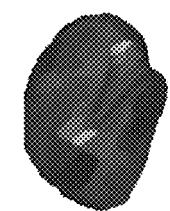
FIG. 74A
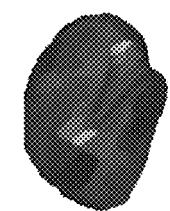
FIG. 74C
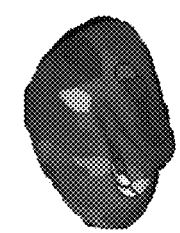
FIG. 74B
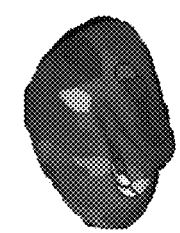
FIG. 74D
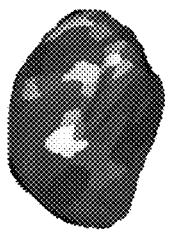
FIG. 77A
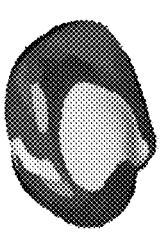
FIG. 77C
FIG. 77B
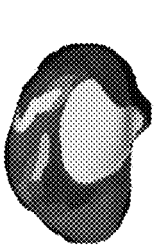
FIG. 77D
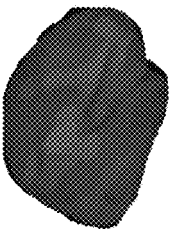
FIG. 73A
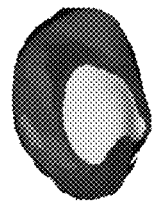
FIG. 73C
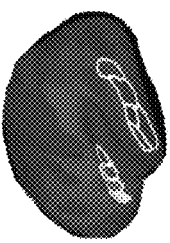
FIG. 73B
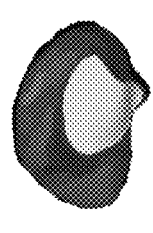
FIG. 73D
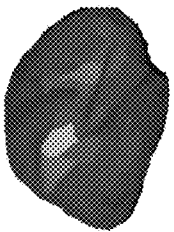
FIG. 76A
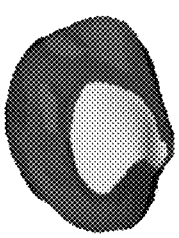
FIG. 76C
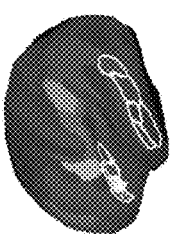
FIG. 76B
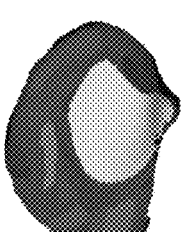
FIG. 76D
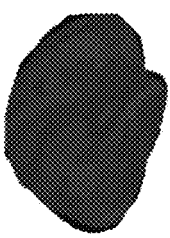
FIG. 72A
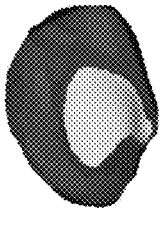
FIG. 72C
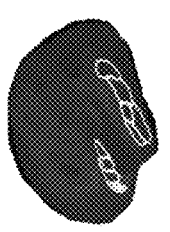
FIG. 72B
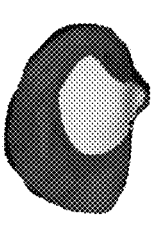
FIG. 72D
FIG. 75A
FIG. 75C
FIG. 75B
FIG. 75D

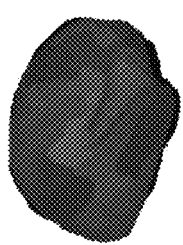
FIG. 80C
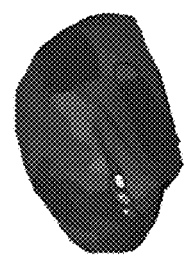
FIG. 80A
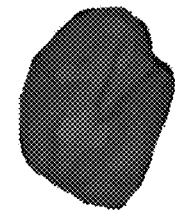
FIG. 79C
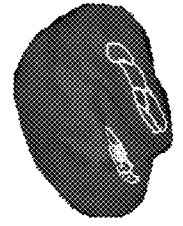
FIG. 79A
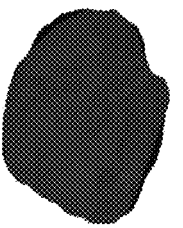
FIG. 78C
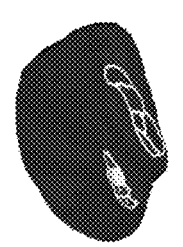
FIG. 78A
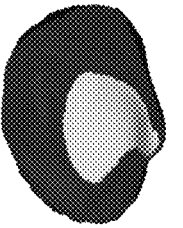
FIG. 78D
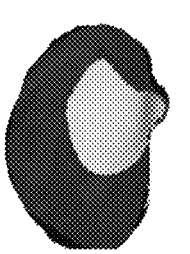
FIG. 78B
FIG. 80D
FIG. 80B
FIG. 79D
FIG. 79B
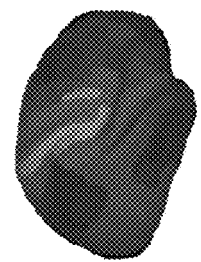
FIG. 83C
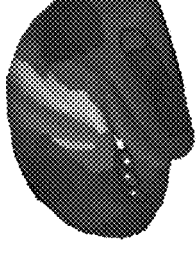
FIG. 83A
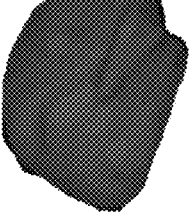
FIG. 82C
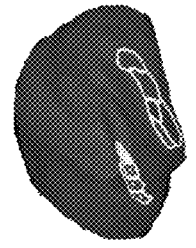
FIG. 82A
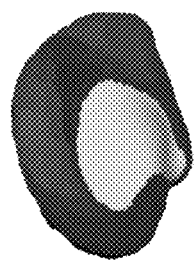
FIG. 83D
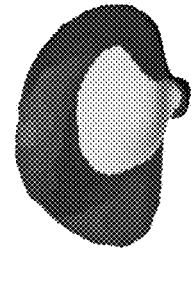
FIG. 83B
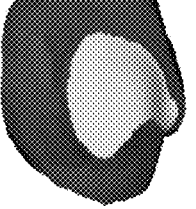
FIG. 82D
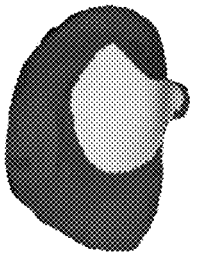
FIG. 82B
FIG. 81C
FIG. 81A
FIG. 81D
FIG. 81B

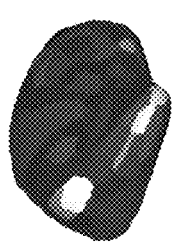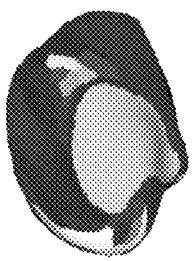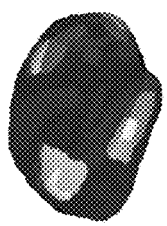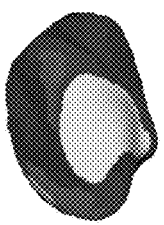
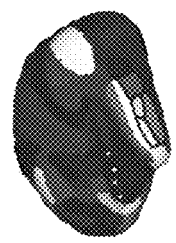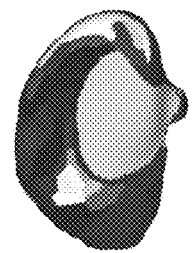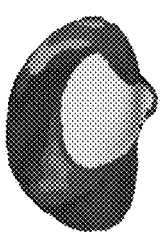
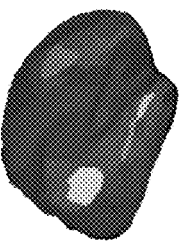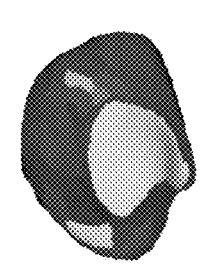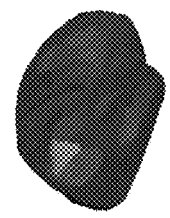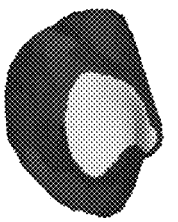
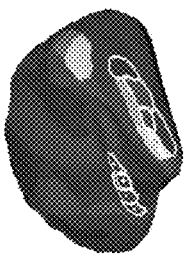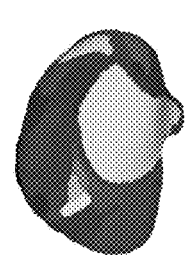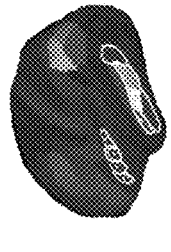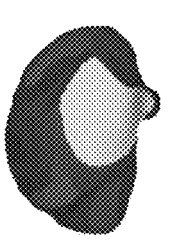
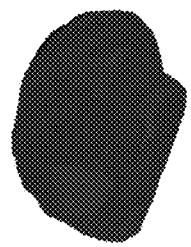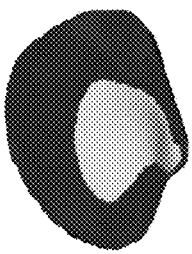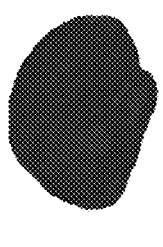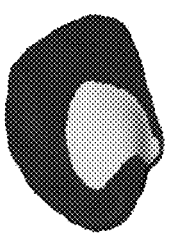
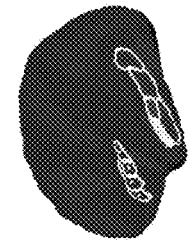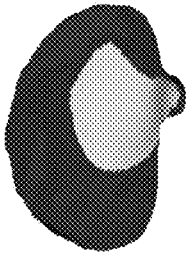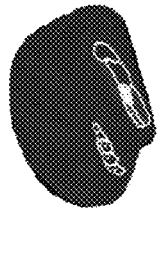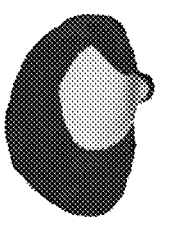

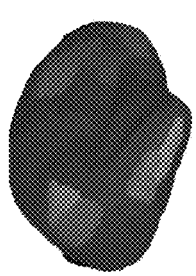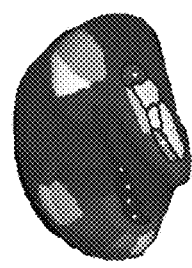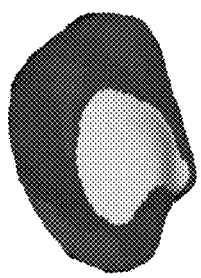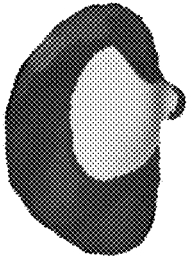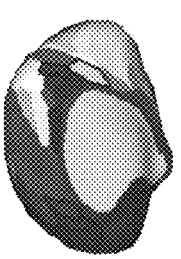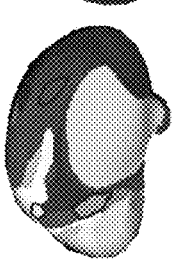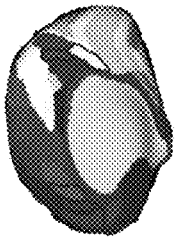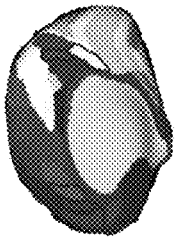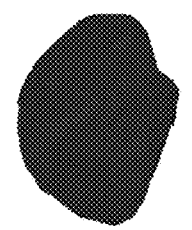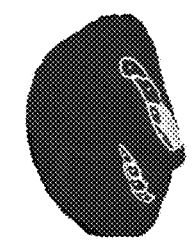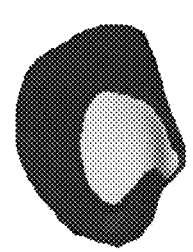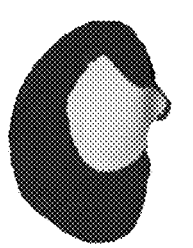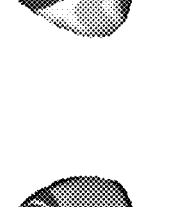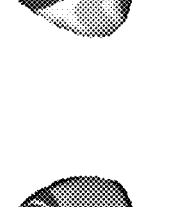

FIG. 104A FIG. 104B FIG. 104C FIG. 104D
FIG. 103A FIG. 103B FIG. 103C FIG. 103D
FIG. 102A FIG. 102B FIG. 102C FIG. 102D
FIG. 107A FIG. 107B FIG. 107C FIG. 107D
FIG. 106A FIG. 106B FIG. 106C FIG. 106D
FIG. 105A FIG. 105B FIG. 105C FIG. 105D

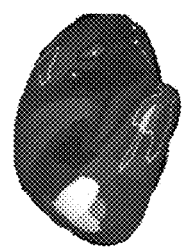  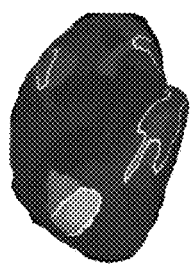 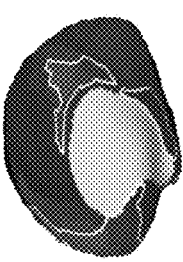
FIG. 110C  FIG. 110D  FIG. 113C  FIG. 113D
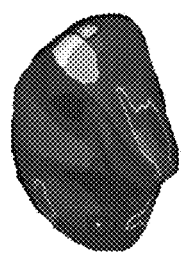 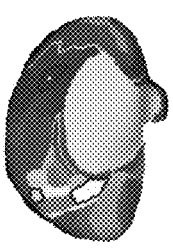
FIG. 110A  FIG. 110B  FIG. 113A  FIG. 113B
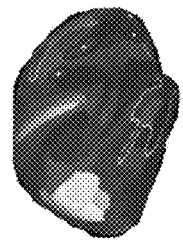 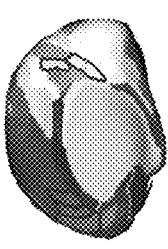 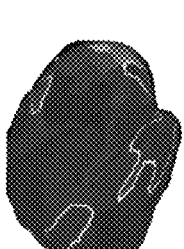 
FIG. 109C  FIG. 109D  FIG. 112C  FIG. 112D
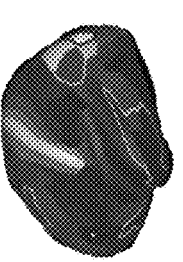 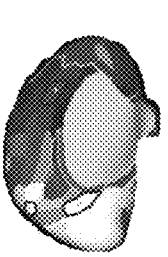 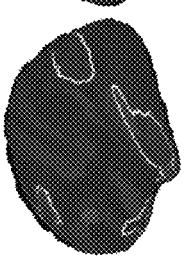 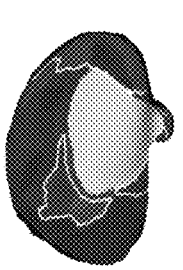
FIG. 109A  FIG. 109B  FIG. 112A  FIG. 112B
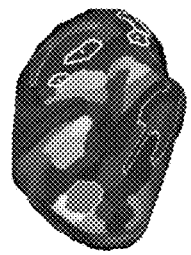 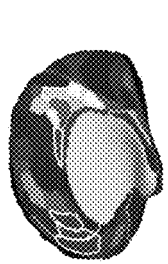 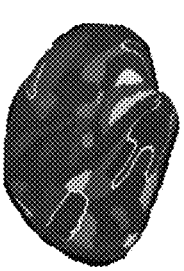 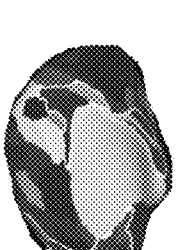
FIG. 108C  FIG. 108D  FIG. 111C  FIG. 111D
 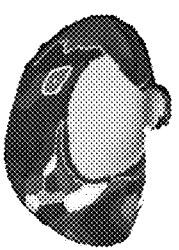 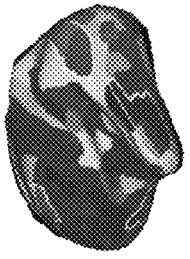 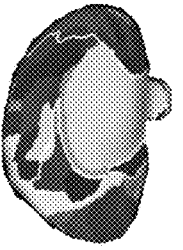
FIG. 108A  FIG. 108B  FIG. 111A  FIG. 111B

 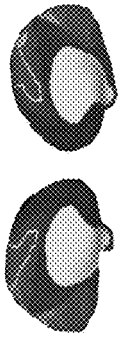
FIG. 116A FIG. 116C FIG. 116B FIG. 116D
 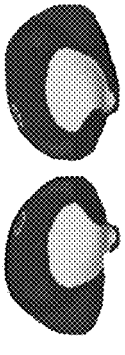
FIG. 119A FIG. 119C FIG. 119B FIG. 119D
FIG. 123A FIG. 123C FIG. 123B FIG. 123D
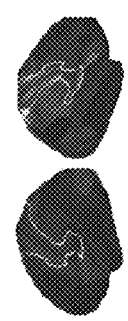 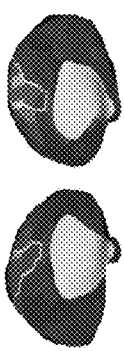
FIG. 115A FIG. 115C FIG. 115B FIG. 115D
 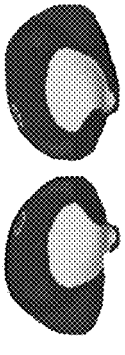
FIG. 118A FIG. 118C FIG. 118B FIG. 118D
FIG. 122A FIG. 122C FIG. 122B FIG. 122D
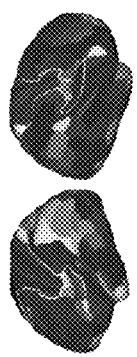 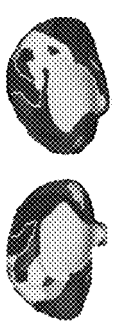
FIG. 114A FIG. 114C FIG. 114B FIG. 114D
 
FIG. 117A FIG. 117C FIG. 117B FIG. 117D
FIG. 121A FIG. 121C FIG. 121B FIG. 121D
FIG. 120A FIG. 120C FIG. 120B FIG. 120D

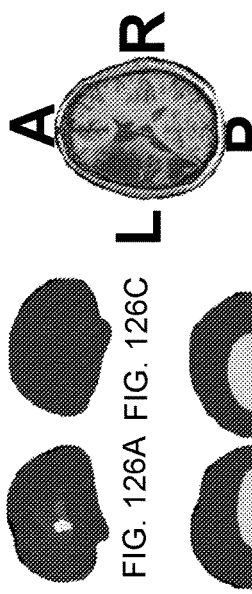
 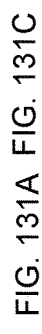    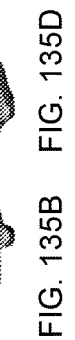 
FIG. 125 FIG. 126A FIG. 126B FIG. 126C FIG. 126D FIG. 127 FIG. 131A FIG. 131B FIG. 131C FIG. 131D FIG. 135A FIG. 135B FIG. 135C FIG. 135D
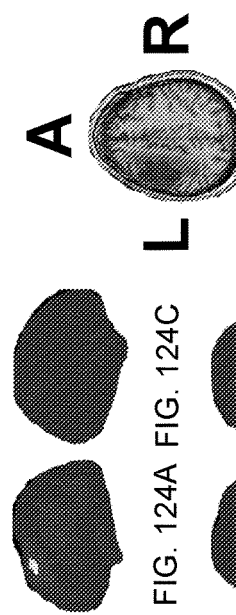
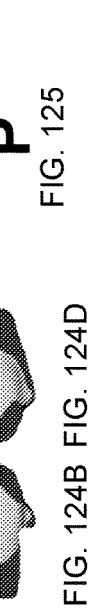
 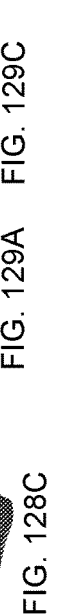      
FIG. 124A FIG. 124B FIG. 124C FIG. 124D FIG. 128A FIG. 128B FIG. 128C FIG. 128D FIG. 129A FIG. 129B FIG. 129C FIG. 129D FIG. 130A FIG. 130B FIG. 130C FIG. 130D FIG. 132A FIG. 132B FIG. 132C FIG. 132D FIG. 133A FIG. 133B FIG. 133C FIG. 133D FIG. 134A FIG. 134B FIG. 134C FIG. 134D

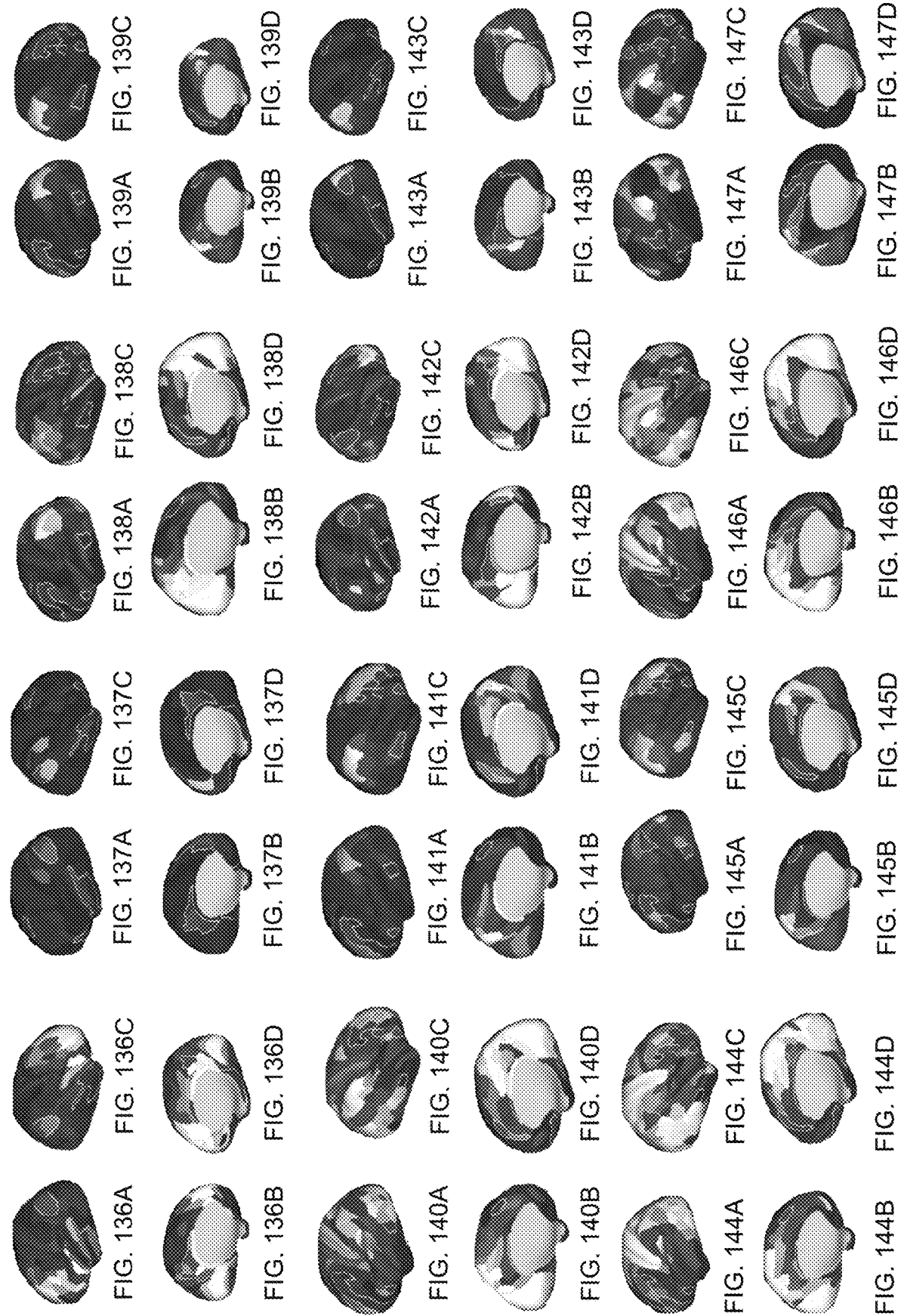

SYSTEMS AND METHODS FOR WHOLE-BRAIN CIRCUIT-BASED NEUROSTIMULATION TO TREAT BRAIN DISORDERS

CROSS-REFERENCE TO RELATED APPLICATIONS

This application is a continuation of International Appl. No. PCT/US2023/68688 filed Jun. 19, 2023; U.S. Provisional Patent Appl. No. 63/354,451 filed Jun. 22, 2022; and U.S. Provisional Patent Appl. No. 63/383,241 filed Nov. 10, 2022, the disclosures of all of which are hereby incorporated by reference in their entireties.

BACKGROUND

Transcranial magnetic stimulation (TMS) is a non-invasive, non-pharmacological procedure for treating neuropsychiatric disorders, in which a magnetic coil is used to stimulate specific regions of the brain. TMS uses short, magnetic field pulses to induce electrical currents in underlying cortical tissue. Through electromagnetic induction, the TMS coil induce an electric current inside the brain at pre-determined targets when a magnetic pulse is delivered to the coil that is placed on top of the patient's skull.

In psychiatry, TMS has been successfully used in treating depression, anxiety disorders, including panic disorder and obsessive-compulsive disorder (OCD). TMS has also been studied with a large number of neuropsychiatric disorders including autism, eating disorder, substance abuse and addiction, posttraumatic stress disorder (PTSD), Alzheimer's disease, coma recovery, stroke, tinnitus, multiple sclerosis, and neurorehabilitation. For treatment-resistant major depressive disorder, TMS has been most widely used in a high-frequency (HF) mode on the left frontal lobe region of the brain called the dorsolateral prefrontal cortex (DLPFC) effectively. It has also been used in low-frequency (LF) mode on the right DLPFC with complementary effectiveness.

TMS over the left dorsolateral prefrontal cortex (L-DLPFC) is an FDA approved treatment for treatment-refractory depression (TRD). This treatment is only partially effective, with response and remission rates of 41.2% and 35.3%, respectively. The FDA approved protocol for TRD identifies the left DLPFC stimulation site by moving the coil 5 cm anterior to the "hand motor hotspot" (motor cortex) along the curvature of the scalp. This approach provides only approximate targeting of the left DLPFC, with no consistent differentiation among DLPFC subregions. After ten years of the FDA-approval of TMS therapy, there has been no significant increase in clinical success.

SUMMARY

Embodiments described herein are exemplary only. Features of the embodiments provide examples of different combination of features. However, the disclosure covers variations of the features in different combinations as well.

The embodiments herein include functional connectivity analysis between regions, between regions and networks, and between networks in order to personalize TMS treatment. Embodiments comprise determining more than one treatment location for administering TMS treatment.

Embodiments of determining a treatment location for treatment comprise identifying one or more treatment regions and networks by comparing patient information to a healthy control group to determine those regions that are outside a desired range as compared to a healthy control group. Embodiments of determining a treatment location for treatment comprises identifying one or more treatment regions that have the highest change in a given region for pre-to post-treatment for individuals having the same characteristics as the patient. The characteristics may be any combination of gender, age, age range, ethnicity, weight, symptoms, diagnosis, prior treatment, response to prior treatment, genetic factors, prior medical conditions, symptoms and/or diagnosis of the patient.

Embodiments of determining a treatment location comprise comparing attributes of fMRI data including amplitude and frequency variations of the spontaneous blood oxygenation level as it fluctuates over time. The comparisons of brain regions and networks are made based on covariation of the variations of the spontaneous blood oxygenation level over time. The covariation may include changes in frequency and amplitude of the blood oxygenation levels over time. The determination of a treatment location for treatment comprises comparing, such as by taking the absolute value of a difference of, the covariation of each brain region to each other region, each brain region to each other network, and of each network to each other network.

The determination of a treatment location for treatment comprises using amplitude and frequency of brain activity within and between networks, between regions, and/or between regions and networks. Embodiments herein may use resting-stated functional connectivity to assess brain activity. Systems and methods herein may comprise Magnetic Resonance Imaging (MRI) systems. The resting-state functional connectivity may be based on changes in the blood oxygenation level of the brain over time. Embodiments herein may use blood oxygenation level dependent (BOLD) imaging to generate images in functional magnetic resonance imaging (fMRI).

TMS treatment systems and methods are provided herein that determine networks and regions within a patient's brain for administering TMS treatments. Although explained herein in terms of TMS treatment, exemplary embodiments are not so limited. In exemplary embodiments, the treatment may also or alternatively include low intensity focused ultrasound (LIFUS). In an exemplary embodiment, if the resulting brain region and/or network for treatment is identified as a cortical brain circuit, then the location may be stimulated with TMS. If the brain region and/or network for treatment is identified as a subcortical brain circuit, then the location may be stimulated with LIFUS. Other protocols and treatments may also be used, such as, for example electrical stimulation.

Systems and methods may be configured to analyze the frequency, amplitude, and frequency relative to amplitude (or vice versa) changes based on the fluctuations of the spontaneous blood oxygenation level-dependent as determined from an MRI of a patient's brain. The comparisons are based on the regions and networks of the brain. The system may be configured and/or the method may include calculating the activation (amplitude of the spontaneous BOLD fMRI fluctuations over time), correlation (frequency of the spontaneous BOLD fMRI fluctuations over time), and/or covariation (correlation to activation of the spontaneous BOLD fMRI fluctuations over time) for the various brain networks and/or regions.

Systems, methods, and non-transitory computer-accessible medium having stored thereon computer-executable instructions for provided herein for determining one or more target regions for TMS treatment of a patient. The systems, methods, and instructions may be configured to: receive fMRI data of a head of the patient; analyze the functional connection of the patient's brain through analysis of the fMRI data by determining changes in any combination of a first fluctuation in amplitude of the fMRI imaging data; a second fluctuation in frequency of the fMRI data, or a third fluctuation in frequency relative to amplitude of the fMRI data; and determine one or more target regions for TMS treatment of a patient based on the determination of any combination of the first fluctuation, the second fluctuation, or the third fluctuation.

The systems, methods, and instructions may be configured to compare the determination of any combination of the first fluctuation, the second fluctuation, or the third fluctuation with measurements of a healthy control group matching one or more characteristics of the patient. Exemplary characteristics of a patient may comprise any combination of gender, age, age range, ethnicity, weight, symptoms, diagnosis, prior treatment, response to prior treatment, genetic factors, prior medical conditions, symptoms and/or diagnosis of the patient. The systems, methods, and instructions may analyze the functional connection of a patient's brain by determining the activation, correlation, and covariation matrices between different brain networks of the patient's brain. The systems, methods, and instructions may analyze the functional connection of a patient's brain by determining activation, correlation, and covariation matrices between regions within networks.

The systems, methods, and instructions may analyze the functional connection of a patient's brain by determining the activation, correlation, and covariation matrices between different brain regions within a network and all other regions within the same network. The systems, methods, and instructions may analyze the functional connection of a patient's brain by determining the activation, correlation, and covariation matrices between different brain regions of different networks. The systems, methods, and instructions may select a first plurality of regions having a low change in amplitude, frequency, and frequency relative to amplitude with the larger number of brain networks or regions. The systems, methods, and instructions may select a second plurality of regions having a high change in amplitude, frequency, and frequency to amplitude with a large number of brain networks or regions.

The systems, methods, and instructions may compare the first plurality of regions and second plurality of regions with regions from a healthy control group matching the patient's characteristics, and selecting the regions above a first threshold value and below a second threshold value to create a potential target group of regions for treatment. The systems, methods, and instructions may compare the potential target group of regions for treatment with a second control group matching the patient's symptoms or diagnosis and determining a subset from the potential target group of regions by determining which of the regions has the greatest change in fMRI data from pre-treatment to post-treatment from the second control group. The systems, methods, and instructions may comprise comparisons of brain regions and networks outside of the DLPhFC.

The systems, methods, and instructions may comprise selecting more than one target location for treatment based on the analysis. The systems, methods, and instructions may include analyzing frequency changes as well as amplitude in determining target locations for treatment. The systems, methods, and instructions may include early stage diagnosis and treatment options for detecting areas in jeopardy of brain damage before structure detection is evident.

The systems, methods, and instructions may be used to determine regions of a patient's brain that is negatively correlated with a large number of other areas of the brain. Using the fMRI to compare functional connections of brain areas, the systems, methods, and instructions may provide early detection of future brain injury by identifying areas of the brain that are functionally disconnected, but which have not yet experienced neurological death or physical deterioration.

Systems, methods, and non-transitory computer-accessible medium having stored thereon computer-executable instructions for determining one or more target regions for TMS treatment of a patient may be configured to: receive MRI data of a head of the patient; analyze the structural connection of the patient's brain through analysis of the MRI data by generating a brain structural connectivity matrix, constructed based on white matter tractography from the whole brain. In an embodiment, structural data is used to run structural connectivity analysis (tractography). The structural data may be T1w/T2w. T1-weighted (T1w) and T2-weighted (T2w) are MRI sequence weighted scans in which T1w MRI may enhance the signal of fatty tissue and suppresses the signal of the water, while T2w MRI may enhance the signal of the water. The structural connectivity matrix may comprise a comparison of the strength of the white matter connection between each combination of two parcels within a plurality of parcels. The strength of the white matter connection may be made using diffusion MRI streamlines tractography. Using voxel-specific directional diffusion information from diffusion-weighted MRI (dMRI), computational tractography produces three-dimensional trajectories through the white matter within the MRI volume that are called streamlines. The connections between the corresponding regions of interest (ROIs) may be quantified as the number of streamlines therebetween. The systems and methods may include selecting target locations for stimulation may include choosing regions with a higher number of white matter connections as compared to other regions. The systems and methods may include selecting target locations for stimulation may include choosing regions with the highest number of white matter connections from the pool of targets based on fMRI functional connectivity.

The systems and methods herein may be used to determine target regions for stimulation using any combination of functional connectivity and/or structural connectivity. The structural connectivity and functional connectivity analysis may be used separately or in combination. When used in combination, the analysis may be run sequentially such that a first set of target regions are identified using a first analysis (whether structural or functional connectivity) and then focused using another analysis (the other of the functional or structural connectivity) of those first set of target regions. In this instance, the another analysis may be used on an outcome from the first analysis to further refine the results from the first analysis to create a target set of regions for stimulation treatment. When used in combination, the analysis may be run concurrently such that a first set of target regions are identified using a first analysis (whether structure or functional connectivity) and a second set of target regions are identified using a second analysis (whether functional or structure connectivity). The final determination of targets for stimulation may be a combination of regions from either or both results from the first analysis and second analysis.

Embodiments described herein may use more anatomically specific models of brain connectivity (functional and/or structural) that can be constructed for individual patients for targeted stimulation.

BRIEF DESCRIPTION OF THE DRAWINGS

The accompanying drawings, which are incorporated herein and constitute part of this specification, are illustrative of particular embodiments of the present disclosure and do not limit the scope of the present disclosure. The drawings are not to scale and are intended for use in conjunction with the explanations in the following detailed description.

With respect to FIGS. 3A-8B, figures with an "A" provide exemplary flow diagrams according to algorithms described herein, while figures with a "B" illustrate representative brain segmentations to explain the flow diagram. Accordingly.

FIGS. 9A-9F illustrates different views of the fMRI brain scan taken from patients before receiving TMS treatment. FIGS. 10A-10F illustrates different views of the fMRI brain scan from the patients of FIGS. 9A-9F after receiving TMS treatment.

FIGS. 11A-124D, 126A-D, and 128A-147D illustrate different views of fMRI scans of a patient before and after treatments and of control groups for comparison according to exemplary embodiments of methods for identifying target locations for stimulation treatment. The figures of the brain scans are separately identified with letters to identify different views for the same brain scan having the same number.

FIGS. 11A-11B are a set of scans at baseline showing target treatment areas at rSFC area STSdp.

FIGS. 14A-16B are a set of scans at baseline showing target treatment areas at RSFC area TPO1; FIGS. 16A-16B are scans of a healthy control group matching the same age and sex as the patient.

FIGS. 23A-23B are a set of scans at baseline showing target treatment areas at RSFC area 55b; FIGS. 24A-24B are scans after fMRI guided TMS according to methods herein; and FIGS. 25A-25B are of a healthy control group matching the same age and sex as the patient.

FIGS. 26A-26B are a set of scans at baseline showing target treatment areas at RSFC area 44; FIGS. 27A-27B are scans after fMRI guided TMS according to methods herein; and FIGS. 28A-28B are of a healthy control group matching the same age and sex as the patient.

FIGS. 29A-29B are a set of scans at baseline showing target treatment areas at RSFC area 45; FIGS. 30A-30B are scans after fMRI guided TMS according to methods herein; and FIGS. 31A-31B are of a healthy control group matching the same age and sex as the patient.

FIGS. 32A-32D are a set of scans at baseline showing target treatment areas at RSFC area p9-46v; FIGS. 33A-33D are scans after fMRI guided TMS according to methods herein; and FIGS. 34A-34D are of a healthy control group matching the same age and sex as the patient.

FIGS. 35A-35D are a set of scans at baseline showing target treatment areas at RSFC area STSdp; FIGS. 36A-36D are scans after fMRI guided TMS according to methods herein; FIGS. 37A-37D are of a healthy control group matching the same age and sex as the patient.

FIGS. 38A-38D are a set of scans at baseline showing target treatment areas at RSFC area TPOJ1; FIGS. 39A-39D are scans after fMRI guided TMS according to methods herein; FIGS. 40A-40D are of a healthy control group matching the same age and sex as the patient.

FIGS. 41A-41D are a set of scans at baseline showing target treatment areas at RSFC area 46 left; FIGS. 42A-42D are a set of scans after fMRI guided TMS according to methods herein including a complete circuit based individual target plan; FIGS. 43A-43D are a set of scans after a conventional single treatment of a targeted TMS treatment based on fMRI data comparing area 46 left within the DLPFC only; and FIGS. 44A-44D are a set of scans of control group matching the same age and sex as the patient.

FIGS. 45A-45D are a set of scans at baseline showing target treatment areas at RSFC area PF left; FIGS. 46A-46D are a set of scans after fMRI guided TMS according to methods herein including a complete circuit based individual target plan; FIGS. 47A-47D are a set of scans after a conventional single treatment of a targeted TMS treatment based on fMRI data comparing area PF left within the DLPFC only; and FIGS. 48A-48D are a set of scans of a health control group matching the same age and sex as the patient.

FIGS. 49A-49D are a set of scans at baseline showing target treatment areas at RSFC area 46 right; FIGS. 50A-50D are a set of scans after fMRI guided TMS according to methods herein including a complete circuit based individual target plan; FIGS. 51A-51D are a set of scans after a conventional single treatment of a targeted TMS treatment based on fMRI data comparing area 46 right within the DLPFC only; and FIGS. 52A-52D are a set of scans of a health control group matching the same age and sex as the patient.

FIGS. 53A-53D are a set of scans at baseline showing target treatment areas at RSFC area PF right; FIGS. 54A-54D are a set of scans after fMRI guided TMS according to methods herein including a complete circuit based individual target plan; FIGS. 55A-55D are a set of scans after a conventional single treatment of a targeted TMS treatment based on fMRI data comparing area PF right within the DLPFC only; and FIGS. 56A-56D are a set of scans of a health control group matching the same age and sex as the patient.

FIGS. 57A-57D are a set of scans at baseline showing target treatment areas at RSFC area STGa; FIGS. 58A-58D are scans after fMRI guided TMS according to methods herein; and FIGS. 59A-59D are of a healthy control group matching the same age and sex as the patient.

FIGS. 60A-60D at baseline showing target treatment areas at RSFC area STSda; FIGS. 61A-61D are a set of scans after fMRI guided TMS according to methods herein; and FIGS. 62A-62D are of a healthy control group matching the same age and sex as the patient.

FIGS. 63A-63D are a set of scans at baseline showing target treatment areas at RSFC area STSva; FIGS. 64A-64D are scans after fMRI guided TMS according to methods herein; and FIGS. 65A-65D are of a healthy control group matching the same age and sex as the patient.

FIGS. 66A-66D are a set of scans at baseline showing target treatment areas at RSFC area STSdp; FIGS. 67A-67D are scans after fMRI guided TMS according to methods herein; and FIGS. 68A-68D are of a healthy control group matching the same age and sex as the patient.

FIGS. 69A-69D are a set of scans at baseline showing target treatment areas at RSFC area STSvp; FIGS. 70A-70D are scans after fMRI guided TMS according to methods herein; and FIGS. 71A-71D are of a healthy control group matching the same age and sex as the patient.

FIGS. 72A-72D are a set of scans at baseline showing target treatment areas at RSFC area FOP5; FIGS. 73A-73D are scans after fMRI guided TMS according to methods herein; and FIGS. 74A-74D are of a healthy control group matching the same age and sex as the patient.

FIGS. 75A-75D are a set of scans at baseline showing target treatment areas at RSFC area FOP4; FIGS. 76A-76D are scans after fMRI guided TMS according to methods herein; and FIGS. 77A-77D are of a healthy control group matching the same age and sex as the patient.

FIGS. 78A-78D are a set of scans at baseline showing target treatment areas at RSFC area FOP3; FIGS. 79A-79D are scans after fMRI guided TMS according to methods herein; and FIGS. 80A-80D are of a healthy control group matching the same age and sex as the patient.

FIGS. 81A-83D are a set of scans at baseline showing target treatment areas at RSFC area FOP2; FIGS. 82A-82D are scans after fMRI guided TMS according to methods herein; and FIGS. 83A-83D are of a healthy control group matching the same age and sex as the patient.

FIGS. 84A-84D are a set of scans at baseline showing target treatment areas at RSFC area TE1a; FIGS. 85A-85D are scans after fMRI guided TMS according to methods herein; and FIGS. 86A-86D are of a healthy control group matching the same age and sex as the patient.

FIGS. 87A-87D are a set of scans at baseline showing target treatment areas at RSFC area TE1m; FIGS. 88A-88D are scans after fMRI guided TMS according to methods herein; and FIGS. 89A-89D are of a healthy control group matching the same age and sex as the patient.

FIGS. 90A-90D are a set of scans at baseline showing target treatment areas at RSFC area TE1p; FIGS. 91A-91D are scans after fMRI guided TMS according to methods herein; and FIGS. 92A-92D are of a healthy control group matching the same age and sex as the patient.

FIGS. 93A-93D are a set of scans at baseline showing target treatment areas at RSFC area PHT; FIGS. 94A-94D are scans after fMRI guided TMS according to methods herein; and FIGS. 95A-95D are of a healthy control group matching the same age and sex as the patient.

FIGS. 96A-96D are a set of scans at baseline showing target treatment areas at RSFC area TE2a; FIGS. 97A-97D are scans after fMRI guided TMS according to methods herein; and FIGS. 98A-98D are of a healthy control group matching the same age and sex as the patient.

FIGS. 99A-99D are a set of scans at baseline showing the inferior parietal cortex, area PGp, left having a high negative correlation/covariation with a large group of brain regions; FIGS. 100A-100D are a set of scans after treatment according to methods herein; and FIGS. 101A-101D are a set of scans of an exemplary control group based on age and sex.

FIGS. 102A-102D are a set of scans at baseline showing a high negative correlation/covariation with a large group of brain regions at the parieto-occipital sulcus area (are POS1, left); FIGS. 103A-103D are a set of scans after treatment according to methods herein; and FIGS. 104A-104D are a set of scans of an exemplary control group based on age and sex according to embodiments described herein.

FIGS. 105A-105D are a set of scans at baseline showing a frontal polar cortex (area a47r, right), having a high negative correlation/covariation with a large group of brain regions using methods described herein. FIGS. 106A-106D are scans after treatment according to methods herein; and FIGS. 107A-107D are of an exemplary control group based on age and sex.

FIGS. 108A-108D are a set of scans at baseline showing target stimulation at parieto-occiptial sulcus area (area POS1, right) having a high negative correlation/covariation with a large group of brain regions; FIGS. 109A-109D are after treatment according to methods herein; and FIGS. 110A-110D are a set of scans of an exemplary control group based on age and sex.

FIGS. 111A-111D are a set of scans at baseline showing dorsolateral prefrontal cortex (area 9p, right) having a high negative correlation/covariation with a large group of brain regions; FIGS. 112A-112D are a set of scans after treatment according to methods herein; and FIGS. 113A-113D are a set of scans of an exemplary control group based on age and sex.

FIGS. 114A-114D are a set of scans at baseline showing a superior parietal cortex (area 7PC, right) having a high negative correlation/covariation with a large group of brain regions; FIGS. 115A-115D are a set of scans after treatment according to methods herein; and FIGS. 116A-116D are a set of scans of a control group based on age and sex.

FIGS. 117A-117D are a set of scans at baseline showing exemplary inferior frontal ocrtex (area 45, right) having a high negative correlation/covariation with a large group of brain regions; FIGS. 118A-118D are scans after treatment according to methods described herein; and FIGS. 119A-119D are a set of scans of an exemplary control group based on age and sex.

FIGS. 120A-120D are a set of scans at baseline showing an exemplary frontal polar cortex (area 10pp, right) having a high negative correlation/covariation with a large group of brain regions; and FIGS. 121A-121B are scans after treatment according to methods herein.

FIGS. 122A-122D are a set of scans at baseline showing an exemplary frontal polar cortex (area TE1m, right) having a high negative correlation/covariation with a large group of brain regions; and FIGS. 123A-123D are after treatment according to methods herein.

FIGS. 124A-127 are brain scans for a patient having experienced a stroke. FIGS. 124A-124D and 126A-126D are from an fMRI brain scan for patients experiencing a stroke showing close to zero functional connectivity. FIGS. 125 and 127 illustrate the corresponding image to show the corresponding structural degradation of the brain areas injured by the stroke.

FIGS. 128A-147D are fMRI brain scans of patients before or after treatment according to exemplary embodiments described herein, or of control persons.

FIGS. 128A-128D are a set of scans at baseline (pre-treatment of a patient) to illustrates an exemplary RSFC area p9-46v identified as potential targets for stimulation; and FIGS. 129A-129D are a set of scans after fMRI guided TMS according to methods herein.

FIGS. 130A-130D are a set of scans at baseline to illustrate an exemplary RSFC area, right hemisphere, dorsolateral prefrontal, area a9-46v, right as potential targets for stimulation; and FIGS. 131A-131D are a set of scans after fMRI guided TMS according to methods herein.

FIGS. 132A-132D are a set of scans at baseline to illustrate an exemplary RSFC area right hemisphere, anterior cingulate, area d32, right, as potential targets for stimulation. FIGS. 133A-133D are a set of scans after fMRI guided TMS according to methods herein.

FIGS. 134A-134D are a set of scans at baseline to show an exemplary RSFC area right hemisphere, anterior cingulate, area a32pr, right, as potential targets for stimulation; FIGS. 135A-135D are a set of scans after fMRI guided TMS according to methods herein.

FIGS. 136A-136D are a set of scans at baseline to show an exemplary RSFC area right hemisphere, anterior cingulate, area 9m, right, as potential targets for stimulation; FIGS. 137A-137D are a set of scans after fMRI guided TMS according to methods herein.

FIGS. 138A-138D are a set of scans at baseline to show an exemplary RSFC area left hemisphere parieto-occipital sulcus areas, area POS2, left, showing target locations for stimulation; FIGS. 139A-139D are scans after fMRI guided TMS according to methods herein.

FIGS. 140A-140D are a set of scans at baseline to show potential targets for stimulation at an RSFC area, right hemisphere, parieto-occipital sulcus areas, area POS2, right; FIGS. 141A-141D are a set of scans after fMRI guided TMS according to methods herein.

FIGS. 142A-142D are a set of scans at baseline to show potential targets for stimulation at RSFC area right hemisphere, parieto-occipital sulcus areas, area POS1, right; FIGS. 143A-143D are a set of scans after fMRI guided TMS according to methods herein.

FIGS. 144A-144D are a set of scans at baseline to show potential targets for stimulation at RSFC area right hemisphere, superior parietal lobule areas, area 7Pm, right; FIGS. 145-145D are a set of scans after fMRI guided TMS according to methods herein.

FIGS. 146A146D are a set of scans at baseline to show potential targets for stimulation at RSFC area right hemisphere, superior parietal lobule areas, area 7Am, right; FIGS. 147A-147D are a set of scans after fMRI guided TMS according to methods herein.

DETAILED DESCRIPTION

Figure 1:
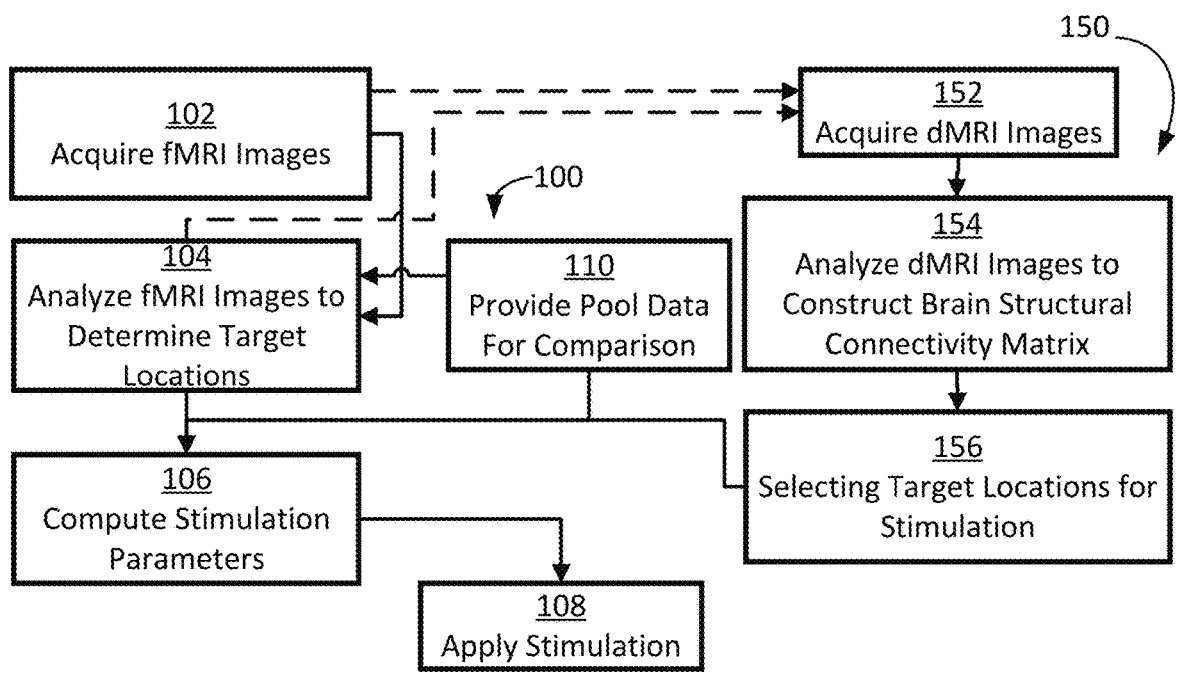
FIG. 1 illustrates a process diagram of embodiments of the method using the network guided stimulation approach.

The following discussion omits or only briefly describes conventional features of the disclosed technology that are apparent to those skilled in the art. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations. A person of ordinary skill in the art would know how to use the instant invention, in combination with routine experiments, to achieve other outcomes not specifically disclosed in the examples or the embodiments.

Unless otherwise specifically defined herein, all terms are to be given their broadest possible interpretation including meanings implied from the specification as well as meanings understood by those skilled in the art and/or as defined in dictionaries, treatises, etc. Unless defined otherwise, all technical and scientific terms used herein have the same meaning as commonly understood by one of ordinary skill in the art in the field of the disclosed technology. It must also be noted that, as used in the specification and the appended claims, the singular forms "a," "an" and "the" include plural referents unless otherwise specified, and that the terms "includes" and/or "including," when used in this specification, specify the presence of stated features, elements, and/or components, but do not preclude the presence or addition of one or more other features, steps, operations, elements, components, and/or groups thereof. Additionally, methods, equipment, and materials similar or equivalent to those described herein can also be used in the practice or testing of the disclosed technology.

Because a patient's mind is the outcome of electrical signals generated all around the brain upon command, the way that the brain learns to carry out tasks is by coordinating these electrical signals and bunching them together based on their frequencies. As such, if the oscillation of the electrical signals falls out of pace with other members of the network, the network loses its ability to properly function. Depending on which network is malfunctioning, the individual experiences the outcome through adverse cognition, emotions and behavior, the classic trademarks of psychiatric disorders.

The system and methods for network guided stimulation provided herein include a personalized approach for correcting the connections of a patient's brain. Embodiments of region and/or network guided stimulation use fMRI as the revolutionary treatment's guidance to restore patient wellness. Because brain illnesses do not follow a one-size-fits all treatment approach, the disclosed systems and methods may include advanced fMRI technology to treat complex brain illnesses with an advanced precise approach using stimulation, such as, for example, TMS. Individual variations in brain organization may require stimulation to be applied to slightly different locations in different individuals. Thus, an important goal of stimulation therapy is to guide stimulation targeting on a personalized basis in order to improve consistency of targeting across individuals. Although descried herein as a treatment method using TMS, other stimulation methods may also be used, such as, for example ultrasound and/or electrical.

The systems and methods for network guided stimulation, such as TMS, described herein include "Network/Circuit" detection that are used as targets for applying stimulation (such as TMS) therapy. Circuits or networks are detected based on activation and connectivity as determined based on images from the fMRI technology. The systems and methods of network guided stimulation (such as TMS) may: (1) Use network guided stimulation for targeting specific circuits instead of single regions of the patient's brain; (2) Use network guided stimulation herein on traumatic brain injuries and other neurological conditions, such as stroke, dementias, etc., and not just psychiatric conditions; (3) Use network guided stimulation on psychiatric conditions with network-based targeting post-treatments having improvements over single region application of TMS.

FIG. 1 illustrates an process diagram of a method 100, 150 using the network guided stimulation approaches. The systems and methods may use any combination of functional 100 and structural 150 connections between areas of the brain (including regions and networks) to determine personalized locations for stimulation treatment. As illustrated, the systems and methods may include acquiring high-resolution fMRI images of the patient's brain, step 102; acquiring dMRI images of the patient's brain, step 152; analyzing the fMRI images to identify the circuits of the patient's brain to be treated from the analyzed fMRI images, step 104; analyzing the dMRI images to identify white matter tractography, step 154; computing the appropriate stimulation based on the analyzed fMRI and/or dMRI images, step 106; and applying appropriate stimulation to the patient's brain based on the appropriate stimulation, step 108.

FIG. 1, step 102, the method 100 may include acquiring images for analysis. The images may be of the patient's brain. The images may include acquiring high-resolution fMRI brain images, which allow detection for each individual of a unique pattern of active brain areas (Nodes) and inter-Node connections (Circuits) that comprise a variety of networks, each with different functions. Embodiments may also or alternatively use dMRI images to make assessments of target locations for stimulation treatment.

The systems and methods may include receiving a detailed medical and psychiatric history if the patient. The method may also include creating a detailed map of the brain where the problems reside. The methods may include seating a patient comfortably in a chair similar to dental chairs and fitting with a sensor cap. A tracker (sensors) attached to a band is placed around the patient's head. The tracker can then receive signals from the patient. Embodiments include obtaining a fMRI, which is a radiological scan that shows how blood is flowing through the brain in real-time. If blood flow to a particular brain region is too high or low compared to normal it will be correlated to the clinical presentation. Areas of abnormal blood flow have been determined to represent poorly functioning regions and their associated dysfunctions.

The system and methods may include obtaining a resting state fMRI (rsfMRI). rsfMRI is an imaging technique that can detect functionally linked brain regions. If multiple fast MRI images are acquired, then a map of fMRI can be constructed by finding the temporal fluctuations in the time series of each brain region (voxel). This is achieved by fMRI's sensitivity to spontaneous BOLD contrast fluctuations. Since the BOLD signal between different brain regions that work together is temporally correlated when the subject is at rest (the subject is presented with no specific stimulus or task) fMRI can reveal deficiencies of various brain networks.

The systems and methods may include receiving fMRI images. The system may be configured with a Magnetic Resonance Imaging machine. The MRI machine may be configured to detect changes associated with blood flow in different parts of the brain. The system may be communication with the MRI machine to take and receive the fMRI images. The system and methods may also be configured to receive fMRI images that are previously taken or separately taken before the TMS treatment. In this case, the system may be configured to communicate, such as through the internet, e-mail, electronic transfer or file share, electronic transfer through memory devices, or other methods in order to receive electronic files having the fMRI images taken with an MRI device before the TMS procedure.

FIG. 1, step 104, the method 100 may include analyzing the fMRI images to determine target locations for treatment sites. Resting-state networks (RSN) are made of a set of brain regions with coherent spontaneous fluctuations in activity. fMRI allows us to explore the brain's functional organization and to examine its differences with normal controls to find malfunctions in neurological or psychiatric diseases. Functional connectivity (FC) may then be calculated by finding statistical dependencies between different regions (voxels). For Gaussian distribution of data, second-order dependencies (i.e., covariances or correlations) are found to build functional connectivity maps.

The system and methos may include determining what loci (locations) of the brain are poorly functioning and correlate it with very sophisticated software. Based on the poor functional connections of the brain, a treatment plan may be devised based on brain circuit (functional), wiring and realigning the target pathways with magnetic beams. After reviewing thousands of the individual's fMRI images, The systems and methods herein may identify the unique pattern of network anomalies, which would include abnormal node function and/or abnormal internode and intranode connections. Embodiments may identify and extract amplitude and frequency of brain activity within and/or between brain networks and/or brain regions in order to analyze connectivity between circuits. The systems and methods may also include algorithms for identifying and extracting amplitude and frequency of brain activity within and between brain networks and/or regions for precise and personalized stimulation treatment, such as TMS treatment.

The systems and methods may use BOLD imaging to measure brain activity. The BOLD images may be subdivided into regions and networks to make different comparisons of the fMRI data of the patient and/or between the patient and one or more healthy and/or control groups. The regions of the brain may be divided based on recognized regions, such as, for example, the Brodmann areas. Other subdivisions of the brain may also be made, such as, for example, based on different functional, connective, and/or developmental criteria. The region may be defined by the Glasser atlas. Regions may be thought of as broader brain areas, e.g., the DLPFC may be a brain region, which is divided based on multimodal techniques into smaller brain areas such as e.g., a9-46v, 9-46, etc. Glasser uses the word area to refer to these subdivisions within regions. Glasser divides the brain in 22 brain regions (bilateral) and 360 brain areas total. The networks of the brain may be identified as collections of regions. The collection of regions may be based on functional connectivity by statistical analysis of the fMRI BOLD signal of the patient and/or based on recognized networks of healthy patients. Networks may also be identified through other recording methods such as EEG, PET, or MEG. Networks may be defined as a group of regions of the brain that are functionally connected. Functional connections may be found using algorithms such as cluster analysis, spatial independent component analysis (ICA), seed based, and others. Networks may be defined based on the resting state of the individual and may include resting state networks (RSN). Networks may include, for example, any combination of medial frontoparietal, midcingulo-insular, dorsal frontoparietal, lateral frontoparietal, pericentral, occipital, limbic, auditory, cerebellar, spatial attention, language, lateral visual, temporal, visual perception, left/right executive. The networks are defined by the Cole-Anticevic atlas. A network may be a group of brain areas (that may be different from brain regions)(or subset of areas within regions) that are interconnected (structurally and/or functionally). Exemplary embodiments may be in terms of identifying regions for TMS target treatment locations, and/or using brain regions in comparisons to identify the target regions. Embodiments may also use areas for target TMS treatment and/or using areas for determining the target locations. Therefore, embodiments may be applied to areas as described herein with respect to regions.

The systems and methods may be used to target individual brain areas based on functional connectivity. Embodiments may use the concept of a circuit to refer to multiple brain areas from the same and/or different networks in order to target the circuits to restore the integrity of a network or the interaction between networks. Comparisons of the BOLD images may be made by comparing different regions and networks of the patient's brain. The regions and networks may be analyzed by comparing the activation, correlation and covariation matrices of the different BOLD regions and/or networks.

The systems and methods may be used to target individual brain areas based on structural connectivity. Embodiments may use dMRI tractography. Structural connectomes may use dMRI tractography in addition to or in combination with those derived through other imaging modalities (e.g., functional MRI) to study and identify underlying white matter tracts of the cortical regions shown as faulty in the functional connectivity maps (i.e., based on activation, covariation, and/or correlation). Functional data may be used initially to select certain brain regions as potential stimulation targets, and then structural data analyses may be used to refine and select priority targets from the potential stimulation targets. fMRI data may be used to guide structural analyses, such as for use when psychiatric disorders may occur with unknown concurrence of stroke, traumatic brain injury, neurodevelopmental or neurodegenerative disorders. Structural data may be used to guide functional analysis, such as when stroke, traumatic brain injury, neurodevelopment or neurodegenerative disorders are present in the patient. The analysis of structural connectivity may be used alone or in combination with the analysis of functional connectivity.

If functional analysis is used to guide structural analysis, the process may include: (1a) use fMRI data to construct the activation, correlation and covariation matrixes and select the targets with stronger (positive and/or negative) activation/connectivity values with a larger group of brain regions and/or (1b) use fMRI data to construct the activation, correlation, and/or covariation matrixes and select regions in with weaker (close to o) activation to connectivity values with a larger group of brain regions; and (2) use structural data to construct the structural connectivity matrix and select regions from 1(a)/1(b) with higher number of white matter connections.

If structural analysis is used to guide functional analysis, the process may include: (1) use structural data to construct the structural connectivity matrix and select regions with lower number of white matter connections; and (2a) use fMRI data to construct the activation, correlation, and/or covariation matrixes and select regions from (1) with stronger (positive and/or negative) activation to connectivity values (activation/connectivity) with a larger group of brain regions; and/or (2b) use fMRI data to construct the activation, correlation and covariation matrixes and select regions from (1) with weaker (close to 0) activation to connectivity (activation/connectivity) values with a larger group of brain regions.

The structural analysis may start with acquiring dMRI images of the patient at step 152. The dMRI images are analysed to construct brain structural connectivity matrix, at step 154. The target locations for stimulation may be determined based from the structural connectivity matrix of step 154. The process may proceed with computing stimulation parameters and applying stimulation from steps 106 and 108.

Using the results from the functional connectivity based analysis for selecting a first set of potential targets, the structural connectivity may be used to identify priority targets and/or additional targets by selecting a set from within and/or in addition to the first set of potential targets to define a set of targets for stimulation treatment.

fMRI guided stimulation treatments may be used to show percentage increase from baseline on the following whole brain measures: total cortical gray matter volume and white surface total area. The structural analysis may be used in combination with the functional analysis for patients experiencing neurodevelopmental disorders, such as, for example, autism spectrum disorders, and neurodegenerative diseases, such as, for example, dementias and Alzheimer's disease. Embodiments may use structural analysis for disorders or conditions of a patient in which structural changes occur within the brain. Embodiments may use structural analysis as additional processing steps to identify target locations for stimulus, such as TMS treatments, based on structural connectivity.

At step 152, the process may include acquiring dMRI images. The structural processing steps use dMRI tractography. The structural connectome constructed using dMRI tractography (alone or in addition to those derived through other imaging modalities, such as fMRI described herein) may be used study underlying shite matter tracts of the cortical regions shown as fault in the functional connectivity maps, such as based on activation, covariation, and correlation.

At step 154, the process may include analyzing dMRI images to construct brain structural connectivity matrix. A brain structural connectivity matrix may be generated based on white matter tractography from the whole brain. A matrix is made of rows and columns representing brain gray matter regions of interest (ROI) (parcels). Exemplary parcellation may be brain gray matter parcellation based on Glasser, and the value in an element of the matrix is the strength of the white matter connection between the two corresponding ROIs, quantified as the number of streamlines. Using voxel-specific directional diffusion information from diffusion-weighted MRI (dMRI), computational tractography produces three-dimensional trajectories through the white matter within the MRI volume that are called streamlines.

At step 156, the target locations for treatment are selected. Selecting target locations for stimulation may include choosing the regions of interest with the higher number of white matter connections. The selection of the higher number of white matter connections may be from the pre-selected potential targets from an another analysis method, such as, for example, the functional connectivity analysis. The selection of the higher number of white matter connections may be independent of any other analysis and may provide additional target locations for stimulation. Selecting targets for stimulation includes choosing a predetermined number of target locations and/or selecting a number of regions of interest in which the number of white matter connections are above a threshold. Selecting targets for stimulation includes choosing regions of interest with the higher number of white matter connections form the pool of targets based on fMRI functional connectivity.

As illustrated, a system and method may include acquiring imaging, such as dMRI images, at step 152. The system and method may then analyze the dMRI images to construct a brain structural connectivity matrix, at step 156, in order to identify or select locations for stimulation at step 156. The structural analysis may be performed before and/or after the analysis of the functional analysis, steps 102 and 104. A first set of identified targets (such as from step 104) may be determined by a first process, such as the functional analysis, and then those first set of identified targets may be used within the structural analysis such that a final selection of targets is based on a priority of the first set of identified targets based on the structural analysis. Alternatively, each functional and structural analysis may be used separately so that a total target set is determined based on a combination of analysis between the functional and structural analysis.

FIG. 1, step 106, the method 100 may include selecting the appropriate TMS coil and the appropriate TMS stimulation, once the networks to be treated are identified. This computation may include the site of stimulation, as well as the parameters which determine results of stimulation, e.g., increasing or decreasing strength of nodes and networks. Parameters may include the strength of the magnetic pulse as well as their frequency and the number of pulses administered during a session, and subsequent sessions, or any combination thereof. By applying repeated pulses (repetitive TMS) at high-frequencies (e.g., >5 Hz), one can excite underlying cortical activity and low-frequency (e.g., <5 Hz) can result in inhibitory changes. The effects of TMS can propagate beyond the stimulation site, through connectivity, impacting a distributed network of brain regions, making the use of resting state functional connectivity (rsFC) a powerful tool for assessing the connectivity, and guiding the optimal coil position with regard to the targeted area.

In determining the intensity of the pulse, the systems and methods may use a pulse with intensity at 100-120% above the patient motor threshold (MT). Depending on the coil being used, Theta Burst stimulation may be applied in 50 Hz triplet bursts five times per second. Embodiments may use an intermittent Theta Burst Stimulation (iTBS), which means that the stimulation can be delivered in a cycle of approximately 2 seconds on and 8 seconds off over a period of 3 minutes. During a typical stimulation session, the patient may receive a total of 600 pulses and 200 bursts. This treatment is known to increase neuronal firing in a given region, and as a result, increases brain activity and functional connectivity in the target region modulating the neural circuit.

Inhibitory Theta Burst stimulation may be applied in 50 Hz triplet bursts five times per second. Continuous Theta Burst Stimulation (cTBS) may be used, which means that the stimulation is delivered continuously over a period of about 40 seconds for a total of 600 pulses. This protocol may be used to decrease neuronal firing which results in decreased regional brain activity and functional connectivity in the brain regions that need to be slowed down, modulating the neural circuit. FIG. 1, step 108, the method 100 may include stimulating the patient according to the parameters computed at step 106. The system and method for stimulating a patient may include using a TMS device and/or navigation system. Use of a navigation system may improve the appropriate placement of the stimulator at the initial and following treatment sessions. Other stimulation methods may also be used including, for example ultrasonic and/or electric stimulation.

Methods and systems are provided for determining networks and regions within a patient's brain for administering TMS treatments. Although explained herein in terms of TMS treatment, exemplary embodiments are not so limited. In exemplary embodiments, the treatment may also or alternatively include low intensity focused ultrasound (LI-FUS). In an exemplary embodiment, if the resulting brain region and/or network for treatment is identified as a cortical brain circuit, then the location may be stimulated with TMS. If the brain region and/or network for treatment is identified as a subcortical brain circuit, then the location may be stimulated with LIFUS. Other protocols and treatments may also be used, such as, for example electrical stimulation.

TMS is a non-invasive (does not enter your body) brain stimulation technique that is used to change brain activity and correct abnormal activity due to illness, using a magnetic field. This magnetic field can pass through the skull to the patient's brain, and induce an electric current at the site of stimulation (focal). TMS can modulate the resting-state activity of the brain and fine-tune DMN plasticity; the direction (increase or decrease in activity) and the extent of this modulation depends on designing a specific rTMS protocol for each individual patient's brain activity. TMS involves the use of a magnetic coil placed over the top side of the head that sends magnetic pulses through the skull (cranium) and into the brain.

The disclosure provided herein may provide different distinct aspects over conventional systems, such as, for example: (1) distinctions and personalization of each patient's brain, acknowledging that every brain is different; (2) treatment targets found from the images of the patient's brain; and (3) treatment delivery with laser precision to the malfunctioning site.

Consistency is important; with each TMS treatment, the networks that are being "retrained" with the application of the TMS pulses preferably has the same treatment, at the same location for it to begin to normalize the associated network connectivity. Therefore, precise location of treatment cites is desirable for improving success and providing longer-lasting wellness. Unlike Standard TMS, where a one-size-fits-all approach is used to select and direct the TMS coil, the personalized TMS Approach may use the unchanging anatomical features of the individual's face (landmarks) for registration, and real-time navigation to direct the treatment. This technology allows The systems and methods may provide the treatment precisely where it is needed for each treatment. The navigation system works based on optical (infrared) tracking, improving precision and accuracy. The accuracy of this optical navigation system is higher than other systems because the registration and real-time navigation are only dependent on the tracker and probe visibility to the infrared camera.

The systems and methods herein may use a precision neuronavigation guidance system, where millimeters of precision are attainable. The guidance system may use functional near infrared spectroscopy (fNIRS) with neuronavigation to deliver precise targeting for the TMS treatment in relation to the identified brain network. The Near infrared spectroscopy may use infrared light delivered through optical fibers to the scalp ad through the skull and into the brain. The infrared light is scatters or reflected by the brain tissue and blood. A secondary set of optical fibers on the scalp capture the infrared light as it exits the head. By detecting changes in the concentration of oxygenated and de-oxygenated hemoglobin in the blood which has been shown by the fMRI studies, a specific navigation map can be created of the head of the patient in relation to the networks used to determine the target TMS treatment locations.

Figure 2:
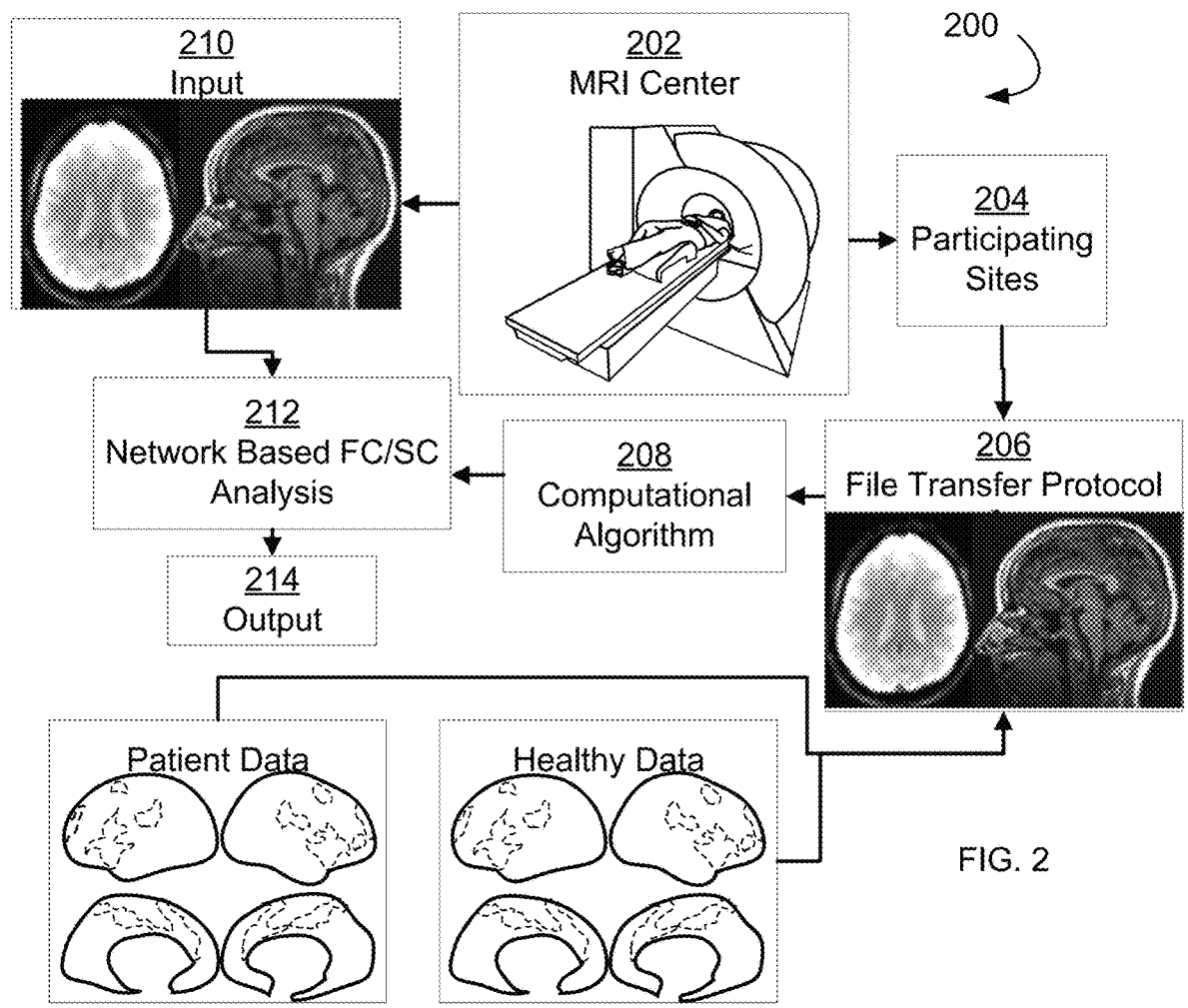
FIG. 2 is an illustrative working model explanation of the methods described herein.

The systems and methods delicately aim a magnetic beam at nodes of networks or circuits of the brain which are functionally disconnected from the normal areas. Using brain mapping technology, embodiments attempt to restore brain circuits to a healthier condition and alleviate the underlying abnormalities. FIG. 2 illustrates a working model explanation of the methods described herein. The method 200 may have a patient obtain a Magnetic Resonance Image (MRI) of their brain at an MRI center at step 202. The method may then perform functional and/or structural connectivity analysis on the fMRI images at step 212, and provide an output at step 214.

As illustrated, and explained above, the system may receive MRI data in different ways. The MRI information may be functional MRI (fMRI) and/or diffusion MRI (dMRI). fMRI is a type of MRI that measures the changes in blood flow that occurs with brain activity. fMRI demonstrates regional, time-varying changes in time-varying changes in brain blood flow. dMRI is a type of MRI in which image contrast is based on the diffusion of water molecules in tissue. The MRI scans may be obtained in different ways. For example, the system may simply generate an input into the functional connectivity analysis (using fMRI) and/or structural connectivity analysis (using dMRI) from the MRI center. The transfer may be through any method to communicate the information, including, without limitation direct connection or communication through a network, such as an online platform. The system may be configured to communicate through file transfer protocols and/or prefer preprocessing on the image data before using the MRI/fMRI/dMRI data as an input into the functional connectivity analysis at step 212. For example, the system may use public domain information such as the Human connectome MRI Protocol for data acquisition. Embodiments may use HCP Pipelines for data pre-processing. Embodiments may use Glasser and Cole-Anticevic atlases, or others as they are developed and made publicly available for use. The participating sites 204 may use the respective or desired file transfer protocols 206 to perform the desired computational algorithms 208 to pre-process the MM data before it is analyzed for functional and/or structural connectivity at step 212.

At step 212, the MRI (fMRI and/or dMRI) data may be received by the system as preprocessed according to the description herein, steps 204, 206, 208.

The system may analyze the functional and/or structural connections within the patient's brain. The pre-processed data may be used to compute the whole-brain activation, correlation, and covariation matrices in individual subjects. Determining the whole-brain activation includes determining a change in amplitude over time of the fMRI data. Determining the whole-brain correlation includes determining the change in frequency of the fMRI data over time. Determining the whole-brain covariation includes determining the change in frequency relative to a change in amplitude over time. As used herein, the covariation is understood to be a ratio of one of the correlation or activation to the other of the activation or the correlation. Therefore, although generally described herein as the correlation to the activation, covariation is also understood to include the reciprocal thereof and remain within the scope of the instant disclosure and definition.

Embodiments may also or alternatively have access to available data for assessing or determining a healthy control group that may include age, gender, race, or other genetic information relevant to the diagnosis and treatment in pathology and/or prevention. Pre-processed data from healthy controls along the age span and pre-post fMRI/TMS in neuropsychiatry may be used to compute average whole-brain activation, correlation, and covariation matrices of a health population.

For example, at 210, the MRI center may provide fMRI information of healthy patients and provide patient information relevant to the relationship to the individual patient, such as age, gender, ethnicity, etc. The system may also retain patient information including fMRI data, patient information relevant to the relationship, TMS protocols, and patient outcomes including responses to TMS treatments based on given TMS target locations. This information may be stored in a database and provided as an input 210 for the functional connectivity analysis of step 212.

The functional connectivity analysis performed herein includes receiving pre-processed fMRI data from the patient and a healthy control data set having metrics in relation to the patient. The metrics may include any combination of age, gender, ethnicity, etc. The metrics in relation to the patient may include characteristics of the healthy control group that are the same or within a given range of the characteristic of the patient. For example, gender may be determined based on whether the sex of the patient is the same as that of someone from the healthy control group. For an age, the healthy control group may be selective if they have an age within a range of that of the patient, such as the patient and the control group fall within pre-determined ranges (such as 5 or 10 year increments), or within a pre-determined range from that of the patient (such as 5 or 10 years older or younger than the patient). The age ranges may be based on recognized developmental levels of the brain, such as adolescence, adulthood, or based on deterioration stages/durations based on age or a given disease or condition, etc.

At step 212, the method includes generating whole brain activation, whole brain correlation and whole brain covariation matrices separately for the patient data and healthy control data set having metrics in relation to the patient. Therefore, the pre-processed patient fMRI data is used to compute whole-brain activation (change in amplitude over time), correlation (change in frequency over time), and covariation (change in frequency relative to change in amplitude over time) for each brain region. Embodiments include receiving pre-processed data from healthy controls along any combination of metrics including age span, gender, ethnicity, etc. For the pre-processed data from healthy controls, the fMRI data may be processed before and after (pre/post) TMS treatment. Embodiments include computing whole brain activation (change in amplitude over time), correlation (change in frequency over time), and covariation (change in frequency relative to change in amplitude over time) for each brain region for each of the pre-and post-treatment fMRI data sets of the healthy controls having metrics within a given range from the patient.

After obtaining the activation, correlation, and covariation matrices of the patient and the healthy control group, the matrices may be assessed in various ways of intra-subject analysis by comparing network coherence and network interactions within portions of the patient's brain, and/or inter-subject analysis by comparing network coherence and interactions between other subjects (the healthy control group and/or the group of subjects with same diagnosis) and the patient. The assessment of activation, correlation, and covariation matrices of the patient may include a first inter-network comparison. In this instance, the method may include computing changes between the activation, correlation, and covariation matrices between brain networks. Therefore, embodiments may include computing a change in amplitude, frequency, frequency relative to amplitude between, or any combination thereof for different brain networks to generate a network to network, inter-network comparison. For example, a first network may be compared against a second network, and then separately to a third network, through the nth network. A second network may then be compared against a third network, then a fourth network, and on through the nth network, and so on until each network has been compared against each other network.

The assessment of activation, correlation, and covariation matrices of the patient may include a first intra-network comparison. In this instance the method may include computing changes between the activation, correlation, and covariation matrices between cortical and subcortical regions within each network. Therefore, embodiments may include computing a change in amplitude, frequency, frequency relative to amplitude between, or any combination thereof for different brain regions within a network. Computing the changes between different brain regions within a network and all other members of the network combined (region to network) may be used to generate an intra-network comparison. For example, a first area of network may be compared against all members of the network (including and/or excluding the first area) combined, then a second area of the network may be compared against all other members of the network (including and/or excluding the second area) combined, and so on until each of the areas of the network and all networks of the brain have been analyzed.

The assessment of activation, correlation, and covariation matrices of the patient may include a second intra-network comparison. In this instance the method may include computing changes between the activation, correlation, and covariation matrices between cortical and subcortical regions within each network, similar to the first intra-network comparison. However, in this case, instead of the region to network comparison, a region to region comparison may now be made. Embodiments may include computing a change in amplitude, frequency, frequency relative to amplitude between, or any combination thereof for different brain regions within the same network. Embodiments may include computing a change in amplitude, frequency, frequency relative to amplitude between, or any combination thereof for different brain regions and other brain regions within a network (region to region) to generate an intra-network analysis. For example, a first brain region of a first brain network, may be compared against a second brain region of the first brain network, then to the third brain region of the first brain network, through the nth brain region of the first brain network. The second brain region of the first brain network may then be compared against the third brain region of the first brain network and each other region through the nth region of the first brain network. The rest of the brain regions may thereafter be compared against all other brain regions not already compared within that brain network. The method may then compare the next brain network, by comparing the first brain region of the second brain network, with each of the other brain regions of the second brain network, until each brain region within each network is compared against each other region of its same network.

The assessment of activation, correlation, and covariation matrices of the patient may include a second inter-network comparison, and a second region to region comparison. In this instance, however, the method may include computing changes between the activation, correlation, and covariation matrices between brain networks, similar to the first inter-network comparison, but between different region of those networks. Therefore, embodiments may include computing changes between the activation, correlation, and covariation matrices between brain regions of different brain networks. Embodiments may include computing a change in amplitude, frequency, frequency relative to amplitude between, or any combination thereof for different regions of different brain networks to generate a region to region, inter-network analysis. For example, a first region of a first network may be compared against a first region of a second network, and then separately to a second region of the second network, through the nth region of the second network. The first region may then be compared to the first region of a third network, through all of the regions of the third network, and so on until the first region of the first region has been compared against all of the regions of all of the other networks outside of the first network. Therefore, when compared with the region to region, intra-network analysis, each region may be compared against each other region of the brain thereby providing an entire brain analysis.

Embodiments of the present disclosure may also or alternatively include different comparisons of the patient against other groups, such as the healthy control group or the group of subjects with same diagnosis that may or may not be selected based on relationships with metrics of the patient, such as, for example, age, ethnicity, gender, condition/illness, treatment history, treatment efficacy, or any combination thereof A statistical comparison may be made of the measurements of the patient with the same measurements made for the healthy control. The healthy control group or the group of subjects with same diagnosis match the same age, gender, diagnosis or symptoms as the patient. However, other criteria of metrics may be made to select members of the healthy control group from that of a larger control group database. For example, the patient measurements may be compared against a healthy control group matching the same relationship metrics (such as having the same age and gender) as the patient and may include a comparison of any combination of the activation, correlation, covariation assessments including network to network, inter-network analysis; region to network, intra-network analysis; region to region, intra-network analysis, and/or region to region, inter-network analysis of the patient to the healthy control group.

The comparison of the patient with the healthy control group or the group of subjects with same diagnosis may be against one or more different control groups based on one or more different relationship metrics. For example, the patient measurements may be compared against a first healthy control group matching a first set of relationship metrics, such as age and gender, as the patient and may include a comparison of any combination of the activation, correlation, covariation assessments including network to network, inter-network analysis; region to network, intra-network analysis; region to region, intra-network analysis, and/or region to region, inter-network analysis of the patient to the first healthy control group. The patient measurements may also or alternatively be compared against a second control group matching a second set of relationship metrics, such as age and diagnosis or symptoms, as the patient and may include a comparison of any combination of the activation, correlation, covariation assessments including network to network, inter-network analysis; region to network, intra-network analysis; region to region, intra-network analysis, and/or region to region, inter-network analysis of the patient to the second control group. Different combinations of relationship metrics for the control groups may be used and fall within the scope of the instant disclosure. For example, a first healthy control group may comprise the same age and gender as the patient; a second control group may comprise the same age and gender as the patient, and may include an overlapping identification of symptoms or diagnosis; a third control group may comprise the same age and may include an overlapping identification of symptoms or diagnosis; a fourth control group may include only those with the same symptoms and/or diagnosis as the patient. The inter-subject analysis may be based on a comparison of one, two, three, or more different control groups. The healthy control group may be individuals with no personal and/or family history of neurological or psychiatric conditions.

The system may be configured to perform any combination of the following functional connectivity analysis:

(1) Network to network, inter-network analysis by computing a change in amplitude, frequency, and frequency relative to amplitude between different brain networks of the same patient, for each network of the patient;

(2) Region to network, intra-network analysis by computing a change in amplitude, frequency, and frequency relative to amplitude between brain regions with a network and all other members of the network of the same patient, for each region of the patient.

(3) Region to region, intra-network analysis by computing changes in amplitude, frequency, and frequency relative to amplitude between different brain regions within a network and all other members within the network of the same patient, for each region of the patient;

(4) Region to region, inter-network analysis by computing changes in amplitude, frequency and frequency relative to amplitude between different brain regions of different networks of the same patient, for each region of the patient.

(5) Statistical comparison of measurements of any combination of (1)-(4) from the patient compared to similar functional connectivity analysis of a healthy control group comprising individuals matching the same age and sex as the patient;

(6) Statistical comparison of measurements of any combination of (1)-(4) from the patient compared to similar functional connectivity analysis of a healthy control group comprising individuals matching the same age, sex, and diagnosis and/or symptoms as the patient.

After the various computations and comparisons of the inter-patient and/or intra-patient has occurred to assess functional connectivity of the patient's brain, the system may be configured to output recommended circuits for stimulation. The TMS protocol may also be customed as needed based on the TMS protocols from the healthy control groups. Exemplary protocols of TMS may include administering TMS at frequencies between 0 and 100 Hertz with amplitudes of 50 to 150 percent of an individual's motor threshold.

The system may analyze the functional and/or structural connections within the patient's brain. As illustrated in FIG. 1, the structural analysis may be performed independent of the functional analysis and/or may be performed in combination therewith. For example, functional analysis may be used to assess the patient and determine target treatment locations in which steps 102, 104, 110, 106, and 108 are performed. Another example, structural analysis may be used to assess the patient and determine target locations in which steps 152, 154, 156, 106, and 108 are performed. The functional and structural analysis may also be used in combination. The functional analysis may be performed first in which steps 102, 104, 110 are performed to identify a first set of potential target locations. Those first set of potential target locations may then be prioritized or analysed according to embodiments of the structural analysis to identify the target locations from within the first set of potential target locations, in which steps 152, 154, and 156 are performed to determine the ultimate parameters at step 106 and administer stimulation treatment at step 108. The processes may be switched such that the structural analysis is performed first to generate the first set of potential target locations that is then used within the functional analysis in order to identify the target locations from the first set of potential target locations for treatment. The processes may be performed in parallel (whether simultaneously or sequentially) such that the one treatment process does not feed into the other, but the entire brain is analyzed according to each embodiment and then the resulting target locations are prioritized together to identify final target locations.

The system may be configured at 212 to analyse the structural connections of the brain. This may include acquiring dMRI images of the patient from the MRI center 202. The dMRI images are analysed to construct brain structural connectivity matrix. The target locations for stimulation may be determined based from the structural connectivity matrix (Structural Connectivity (SC) analysis of algorithm 212). The process may proceed with computing stimulation parameters as the output at 214.

Using the results from the functional connectivity based analysis for selecting a first set of potential targets, the structural connectivity may be used to identify priority targets and/or additional targets by selecting a set from within and/or in addition to the first set of potential targets to define a set of targets for stimulation treatment.

MRI guided stimulation treatments may be used to show percentage increase from baseline on the following whole brain measures: total cortical gray matter volume and white surface total area. The structural analysis may be used in combination with the functional analysis for patients experiencing neurodevelopmental disorders, such as, for example, autism spectrum disorders, and neurodegenerative diseases, such as, for example, dementias and Alzheimer's disease. Embodiments may use structural analysis for disorders or conditions of a patient in which structural changes occur within the brain. Structural analysis may include additional processing steps to identify target locations for stimulus, such as TMS treatments, based on structural connectivity.

The system at 212 may include analyzing dMRI images to construct brain structural connectivity matrix. A brain structural connectivity matrix may be generated based on white matter tractography from the whole brain. A matrix is made of rows and columns representing brain gray matter regions of interest (ROI) (parcels). Exemplary parcellation may be brain gray matter parcellation based on Glasser, and the value in an element of the matrix is the strength of the white matter connection between the two corresponding ROIs, quantified as the number of streamlines. Using voxel-specific directional diffusion information from diffusion-weighted MRI (dMRI), computational tractography produces three-dimensional trajectories through the white matter within the MRI volume that are called streamlines.

The structural connection of the patient's brain may be analysed through MRI data to generate a brain structural connectivity matrix. MRI data may be used to run structural connectivity analysis (tractography). The structural data is used to run structural connectivity analysis (tractography). The structural data may be T1w/T2w. T1-weighted (T1w) and T2-weighted (T2w) that are MRI sequence weighted scans in which T1w MRI may enhance the signal of fatty tissue and suppresses the signal of the water, while T2w MRI may enhance the signal of the water. The structural data (such as, for example, T1w/T2w) is used for structural connectivity analyses (such as tractography) to study whole brain structural architecture.

The system may be configured to output 214 the target locations for treatment that are selected from the algorithm 212. Selecting target locations for stimulation may include choosing the regions of interest with the higher number of white matter connections. The selection of the higher number of white matter connections may be from the pre-selected potential targets from an another analysis method, such as, for example, the functional connectivity analysis. The selection of the higher number of white matter connections may be independent of any other analysis and may provide additional target locations for stimulation. Selecting targets for stimulation includes choosing a predetermined number of target locations and/or selecting a number of regions of interest in which the number of white matter connections are above a threshold. Selecting targets for stimulation includes choosing regions of interest with the higher number of white matter connections form the pool of targets based on fMRI functional connectivity.

At step 214, the output may comprise a selection of regions for administering TMS. In order to obtain the selection of regions, the system may be configured to analyze the various computations made to determine functional and/or structural connectivity, the comparisons performed in step 212. The system may be configured to select the top threshold percentage of brain regions that satisfy select conditions for each step of the analysis performed in step 212 in which regions and/or networks of the fMRI data is analyzed to determine functional connectivity and/or for regions with higher number of white matter connections to determine structural connectivity. The computations made for determining functional connectivity may include, as an example, any combination of (1) network to network, inter-network analysis, (2) region to network, intra-network analysis; (3) region to region, intra-network analysis; (4) region to region, inter-network analysis; and (5) One or more statistical comparisons of measurements of any combination of (1) through (4), above, from the patient compared to similar functional connectivity analysis of a control group, in which the control group may be selected on one or more combination of relationship metrics, such as, for example age, gender, symptoms, diagnosis, ethnicity, etc. The computations made for determining structural connectivity may include, as an example, any combination of (1) generating brain structural connectivity matrix based on white matter tractography from the whole brain; (2) generating brain structural connectivity matrix based on white matter tractography from a subset of the brain based on another brain analysis method (such as functional connectivity); (3) create a matrix representing brain gray matter regions of interest based on a desired parcellation; (4) determining a value in an element of the matrix as the strength of the white matter connection between two corresponding regions of interest; and/or (5) using voxel-specific directional diffusion information from diffusion-weighted MRI to produce three dimensional trajectories through white matter (streamlines).

The system may be configured to select threshold percentage of brain regions that satisfy the following conditions from the above computations made for determining functional connectivity of the patient based on intra-patient comparisons:

7. Select a first threshold of regions in which the lowest change in amplitude, frequency, frequency relative to amplitude, or a combination thereof occurs with the largest number of brain networks and regions.
8. Select a second threshold of regions in which the highest change in amplitude, frequency, frequency relative to amplitude, or a combination thereof occurs with the largest number of brain networks or regions of the patient.

The comparisons are intended to identify regions of the patient's brain that are outliers in activity, either having the lowest change or the highest change with the most other regions and networks of the patient's brain. In other words, each of the computations 1-4 above can be ranked for each region of the brain based on the change in amplitude, frequency, and frequency relative to amplitude. The regions that occur below a third threshold may be grouped together and the total number of each region within below the third threshold may be determined (the frequency distribution of the regions below the third threshold). Similarly, the frequency distribution of the regions above a fourth threshold may be determined. The regions having the highest occurrence in each group (occurring below the third threshold or above the fourth threshold) are then used in the determination of steps 7 and 8, above. The comparisons and identified regions based on intra-patient data provide an intra-patient output in which a number of regions are identified based on the analysis of the activation, correlation, and covariation information of the patient's data.

A threshold may be used to separate the number of identified regions. The identified networks may be determined based on different thresholds. For example, the first and second thresholds to determine the final number of regions may be for example, the top 1%, 5%, 10%, 15%, 25%, or other threshold. The thresholds may be the same or different. Different thresholds may be used for different comparisons. For example, when determining the highest and lowest changes in amplitude, when separating regions for the frequency distribution, the regions may be separated at the 50% range so the top half regions are analyzed for determining the highest change, while the lower half of regions are analyzed for determining the lowest change.

The system may be configured to select threshold percentage of brain regions that satisfy the following conditions from the above computations made for determining functional connectivity of the patient as compared to one or more healthy control groups, inter-patient comparisons:

9. Compare the intra-subject outputs (e.g., steps 7 and 8) with outputs in the healthy control group having the same first metric relationship (the same age and sex in the example using steps 5-6), and select the regions that are outside of a determined normal range when compared to the healthy control group.
10. Compare intra-subject outputs (e.g., steps 7 and 8 or 9) with outputs in the control group having the same second metric relationship (the same diagnosis and symptoms in the example using steps 5-6), and select the regions that have the maximum change in the activation, correlation, and covariation pre- and post-TMS treatment.

In order to save computation, the order of steps may be run in different orders, and on different inputs. For example, the last step above, 10, may be based on the regions identified from steps 7 and 8 or those that are narrowed by the filter from step 9.

At step 9, the system may compare the intra-subject outputs from steps 7 and 8 to obtain the regions with values below a fifth threshold and above a sixth threshold of the mean in the healthy control group matching the first metric relationship. The fifth and sixths threshold may be the same or different. The fifth and sixth threshold may be based on a number of standard deviations, such as 1, 2, 2.5, or 3 standard deviations away from the mean. The identified regions from step 9 may thereafter be compared in step 10 to the pool of patients matching the second metric relationship. In this case, a subset of regions from step 9 may be selected for those regions that have the greatest change of the activation, correlation, and covariation between the pre-and post-TMS treatments from the pool of patients of the control group having the second metric relationship. In other words, the regions of the control group matching the second metric relationship (e.g., same diagnosis and/or symptoms, with or without the same age, gender, and/or ethnicity) are compared by taking the absolute value different between the pre- and post-treatment for each patient in the control group. The regions with the maximum change, greatest absolute value, are then identified as the output of step 10. A seventh threshold may be used to determine the cutoff, such as the top 1 percent, 5 percent, 10 percent, top 1. 2, 3, 4, or more regions.

The system may be configured to use structural connections to select target locations from the potential selections based on functional connectivity.

Embodiments may include an output including a report for the patient and/or practitioner administering the TMS treatment. The report may include one or more images of the patient's brain. For example, and of the BOLD images, comparisons of the activation, correlation, covariation, or other combination of images used herein may be provided. The report may include a visual display of the brain map. The report may include a statistical display. The report may include the recommended regions, networks, and/or circuits for stimulation by the TMS treatment. The report may include the TMS protocol customed as needed based on the comparisons made herein.

The stimulation parameters may also be provided that may be individualized to the patient. Once the regions from the above steps are identified to administer TMS, an excitatory (>5 Hz) or inhibitory (<5 Hz) TMS protocol may be chosen. Treatment coils may also be chosen based on focality and depth. Focality may be the width of the stimulated area (horizontal axes) and the depth may be the distance from the scalp to targeted area (vertical axes). Additional or alternate TMS treatment parameters may be determined from the parameters of the prior patient group having the best results pre- to post-TMS treatment. The treatment parameters from the patients that resulted in the greatest pre- and post-changes in the brain regions from the comparison of step 10 may be used to inform the treatment parameters for administering the patient. For example, the treatment parameters may include an average, a weighted average, an average after filtering, or the treatment parameters from the patient or patients having the greatest change for that identified region. The system may also compare the healthy control group data to determine treatment parameters. For example, once the region(s) are identified, a control group may be used to identify the patients with the highest change pre- and post-treatment for that region based on a third relationship metric (that may or may not be the same as the first or second relationship metric)—e.g., the control group may be used to identify a group of patients with the highest pre- and post-changes to a given region against the entire control group or as compared against a sub-set of the control group matching the same gender, age, ethnicity, or a combination thereof (or other combination of relationship metrics). The parameters from the identified healthy control group treatment(s) may be used alone or in combination, such as an average, to create a customized treatment protocol for the patient.

FIGS. 3A-8B illustrates flow diagrams and corresponding brain visuals for explaining the exemplary functional connectivity analysis. The system may be configured to perform any combination of the following functional connectivity analysis:

1. Network to network, inter-network analysis by computing a change in amplitude, frequency, and frequency relative to amplitude between different brain networks of the same patient, for each network of the patient;
2. Region to network, intra-network analysis by computing a change in amplitude, frequency, and frequency relative to amplitude between brain regions with a network and all other members of the network of the same patient, for each region of the patient.
3. Region to region, intra-network analysis by computing changes in amplitude, frequency, and frequency relative to amplitude between different brain regions within a network and all other members within the network of the same patient, for each region of the patient;
4. Region to region, inter-network analysis by computing changes in amplitude, frequency, and frequency relative to amplitude between different brain regions of different networks of the same patient, for each region of the patient.
5. Statistical comparison of measurements of any combination of (1) through (4), above, from the patient compared to similar functional connectivity analysis of a healthy control group comprising individuals matching the same age and sex as the patient;
6. Statistical comparison of measurements of any combination of (1) through (4), above, from the patient compared to similar functional connectivity analysis of a healthy control group comprising individuals matching the same age, sex, and diagnosis and/or symptoms as the patient.

Systems and methods may include determining a change in amplitude, frequency, and/or frequency relative to amplitude between different brain networks to networks, regions to regions, or regions to networks. The differences are determined based off of the spontaneous BOLD contrast fluctuations when the subject is at rest (the subject is presented with no specific stimulus or task). The BOLD contrast fluctuations may be determined from fMRI by comparing different brain regions and networks. The brain may be divided into different regions. The regions may be based on recognized brain regions, or other subdivisions based on the activity of regions of the brain based on different functional, connective, and/or developmental criteria, or as indicated in the fMRI images of the patient and/or of a healthy patient group. The networks of the brain may be identified as collections of regions. The collection of regions may be based on functional connectivity by statistical analysis of the fMRI BOLD signal of the patient and/or based on recognized networks of healthy patients. Other delineations of regions and networks may be used. FIG. 3B illustrates an exemplary brain subdivided in an exemplary 4 networks identified as n=1, n=2, n=3, and n=4. FIG. 3D illustrates the exemplary brain of FIG. 4B subdivided further into individual regions so that each network comprises a plurality of regions. The number of regions per network may be the same or different. For example, the first network, n=1, of FIG. 3B, is subdivided into four regions, while the second network, n=2, is subdivided into three regions. The illustrated regions and networks are for provided only to explain the associated flow diagrams and are not intended to be limiting as to actual brain regions and/or networks.

The exemplary functional connectivity analysis comprises various analysis of the frequency, amplitude, and frequency relative to amplitude changes based on the fluctuations of the spontaneous blood oxygenation level-dependent as determined from the fMRI. The comparisons are based on the regions and networks of the brain. Therefore, FIG. 3A illustrates a flow diagram for calculating the activation (amplitude of the spontaneous BOLD fMRI fluctuations), correlation (frequency of the spontaneous BOLD fMRI fluctuations), and covariation (correlation to activation of the spontaneous BOLD fMRI fluctuations) for the various brain networks, while FIG. 4A illustrates the calculations of the activation, correlation, and covariation for the various brain regions.

Figure 3A:
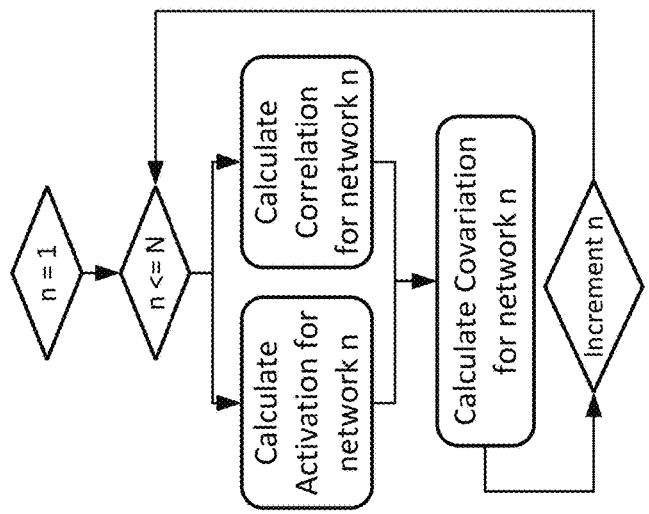
FIGS. 3A-3B illustrate exemplary analysis for determining covariation for each network within the brain of a patient.
Figure 3B:
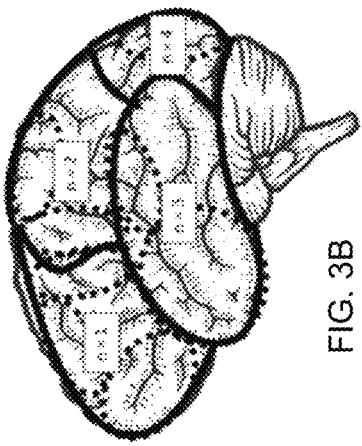

Referring to FIG. 3A, the BOLD fluctuations of the first brain network area is determined for each network of the brain. The network may be associated with a given value by determining a medium, average, or other statistical value associated with a distribution to associate an amplitude and/or frequency of the BOLD fluctuations to the given network. As illustrated, the analysis starts with the first network, n=1. If not all of the networks have been analyzed, which would not be the case of the first network, then the system calculated the activation for the first network and the correlation for the first network. From these values, the system can then calculate the covariation as the ratio of the correlation to the activation (or vice versa). The system then increments to the next network to determine the activation, correlation, and covariation thereof. The system progresses through each network until all networks (n≤N) have an associated activation, correlation, and covariation value.

Figure 4A:
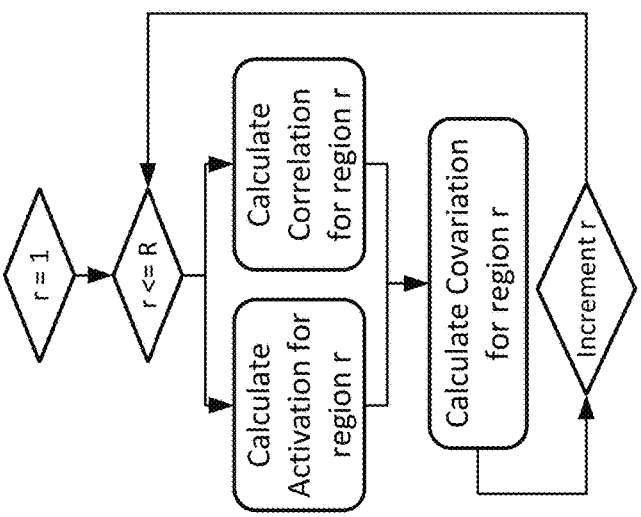
FIGS. 4A-4B illustrate exemplary analysis for determining covariation for each region within the brain.
Figure 4B:
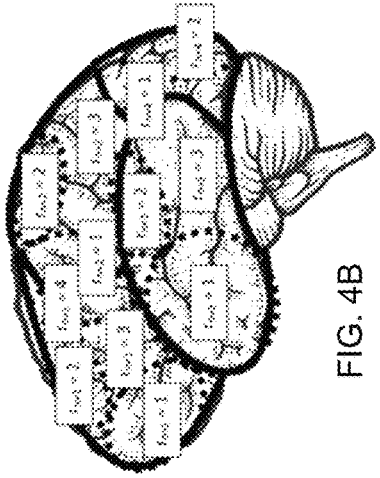

Referring to FIG. 4A, the BOLD fluctuations of the first brain region is determined for each region of the brain. The region may be associated with a given value by determining a medium, average, or other statistical value associated with a distribution to associate an amplitude and/or frequency of the BOLD fluctuations to the given area. As illustrated, the analysis starts with the first region. If not all of the regions have been analyzed, which would not be the case of the first region, then the system calculates the activation for the first network and the correlation for the first network. From these values, the system can then calculate the covariation as the ratio of the correlation to the activation (or vice versa). The system then increments to the next region to determine the activation, correlation, and covariation thereof. The system progresses through each region until all nodes ($r \leq R_{max}$) have an associated activation, correlation, and covariation value.

As used herein, all of the activation, correlation, and/or covariation of each network and/or region may be calculated and/or saved to a database. As described herein with respect to FIGS. 3A-8B, the covariation may be saved and analyzed between the various regions and networks. Therefore, the activation and correlation may be calculated during the calculation of the covariation, but not separated determined and/or saved to the system. Such intermediate determination is understood to be included in the definition of calculation the activation and/or correlation as used herein.

As illustrated, each network is identified is a numerical sequential value, while each region is identified as its network, and sequential numerical value for the region. Systems and methods may use any indexing system to associate the activation, correlation, and/or covariation of the given network and/or region. Therefore, as explained in the associated flow diagram of FIG. 4A, when comparing r≤Rmax, the given value of R is not necessarily restricted. Instead, the comparison is intended to illustrate that the current region is one of the regions that needs to be analyzed and has not previously been analyzed.

Figure 5A:
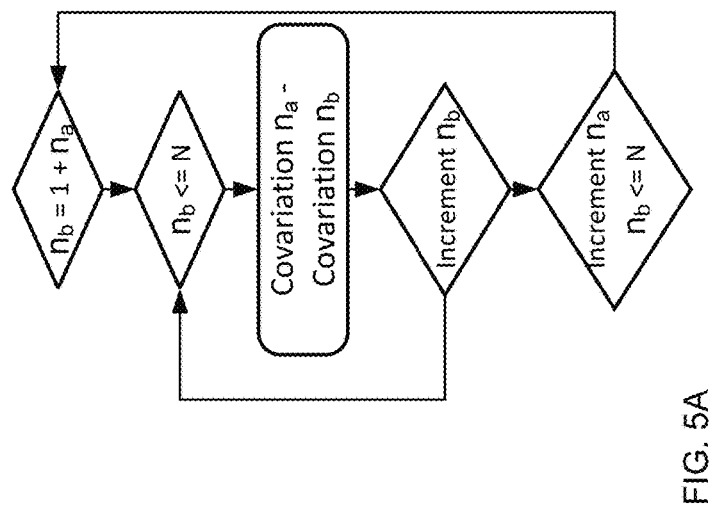
FIGS. 5A-5B illustrate exemplary analysis for comparing covariation between networks within the brain.
Figure 5B:
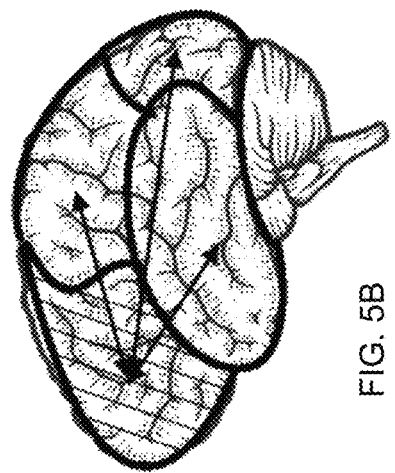

Exemplary embodiments include comparing each of the brain networks to each of the other brain networks. As illustrated in FIG. 5A, a first network selected to compare to all other networks. For example, $n_a=(n=1)$ from FIG. 3B, as indicated by the cross hatching of this network in FIG. 5B. That first network is then compared to the next network (n=2) by taking the difference of the covariation values from the information as determined from the algorithm described with respect to FIGS. 3A and 3B. That same first network is then compared to the next network (n=3) by taking the difference of the respective covariation values. Once the first network has been compared to all other networks, then the next network (n=2), is then compared against all other networks. The difference between a previous comparison may not be repeated. Therefore, if the difference of n1 from n2 has already been determined, then the difference of n2 from n1 is not necessarily also determined. Therefore, as next network is compared against all other higher order or previously uncompared networks. The comparison loop therefore is illustrated in terms of $n_b=n_a+1$ so that all previously uncompared networks from $n_a$ may be compared against $n_a$. The loop continues until all of the networks have been compared against all other networks. As illustrated in FIG. 5B, only the inner loop is illustrated in which $n_a=1$ has been compared to all other networks ($n_b=n_a+1=2$ to $n_b=N$).

Figure 8A:
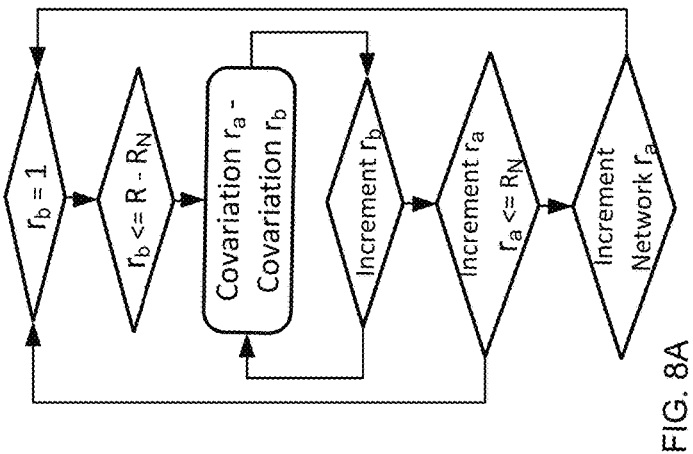
FIGS. 8A-8B illustrate exemplary analysis for comparing covariation of regions within one network to regions within other networks. The systems and methods may use any combination of the analysis with respect to the different covariation calculations and comparisons.
Figure 8B:
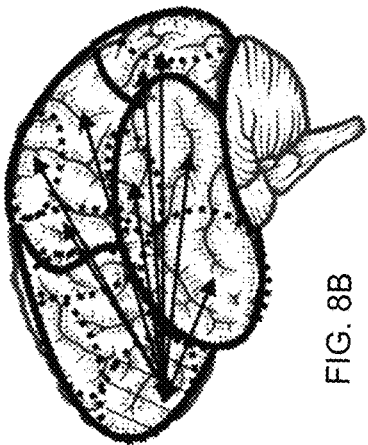
Figure 7A:
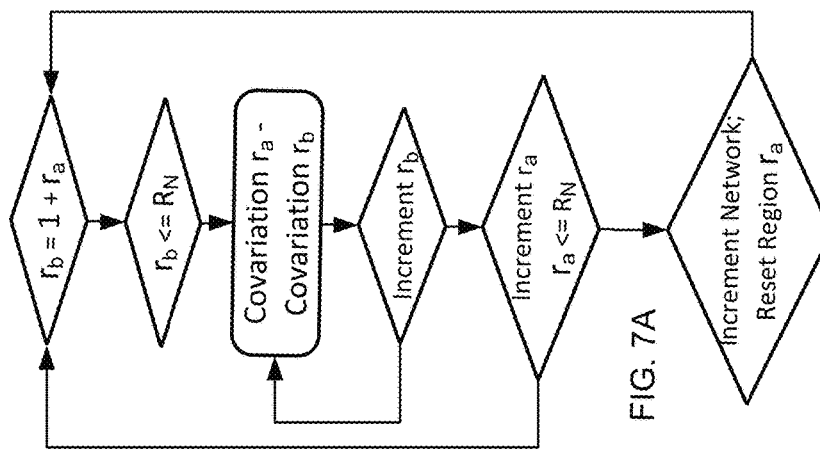
FIGS. 7A-7B illustrate exemplary analysis for comparing covariation between regions within the same network.
Figure 7B:
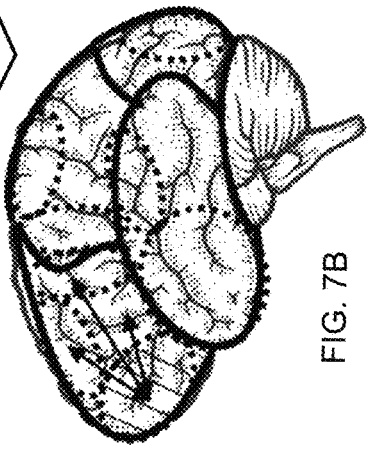

Embodiments include comparing each of the brain region to each of the other brain regions. The comparison may be handled in two segments in which a region within a network is compared against all other regions within the same network, region to region, intra-network as illustrated in FIGS. 7A to 7B, as well as each region within a network is compared against all other regions within the other networks, region to region, inter-network as illustrated in FIGS. 8A to 8B. The combination of these two loops results in each region being compared against each other region of the brain by taking the difference of the respective covariation values between each region. In other words, a first region selected to compare to all other regions, such as $r_a=(r_{n=1}=1)$ from FIG. 4B, as indicated by the cross hatching of this region of FIGS. 7B and 8B. Referring to FIG. 8B, that first region is then compared to the next region within the network ($r_b=(r_{n=1}=2)$) by taking the difference of the covariation values from the information as determined from the algorithm described with respect to FIGS. 4A and 4B. Referring to FIG. 8B, that first region is also compared against the next region with the next network ($r_b=(r_{n=2}=1)$) by taking the difference of the covariation values from the information as determined from the algorithm described with respect to FIGS. 4A and 4B. As the algorithm loops through either FIG. 7A or 8A, that first region is compared against the next region within the first network (FIG. 7B) or the next network (FIG. 8B). The respective loops continue until each region has been compared against each other region by determining a difference in the covariation between each of the regions.

Figure 6A:
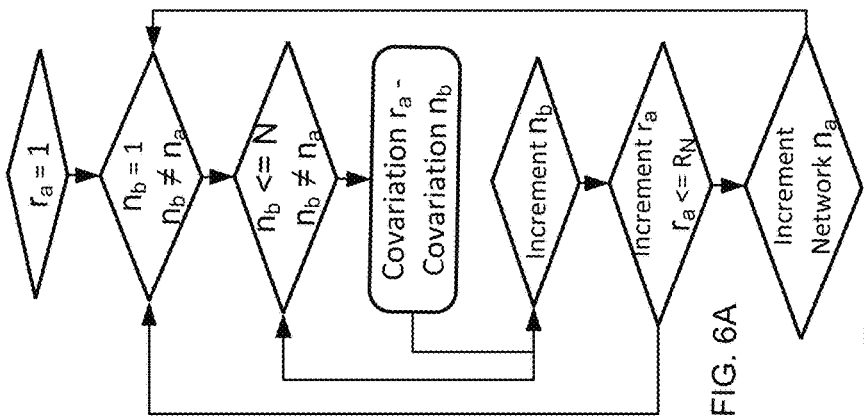
FIGS. 6A-6B illustrate exemplary analysis for comparing covariation of each region against each external network from the network containing the region being compared.
Figure 6B:
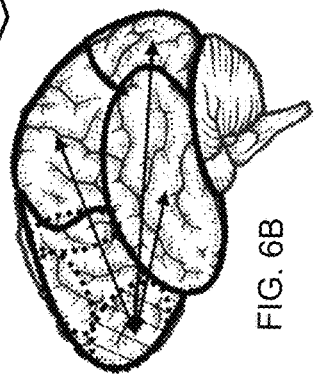
Figure 16A:
Figure 16B:
Figure 15A:
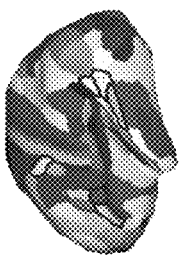
FIGS. 15A-15B are scans after fMRI guided TMS according to methods herein.
Figure 15B:
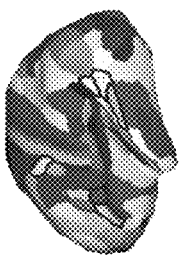
Figure 22A:
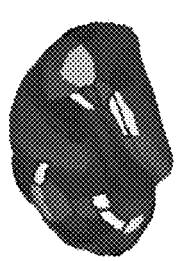
FIGS. 22A-22B are scans of a healthy control group matching the same age and sex as the patient.
Figure 22B:
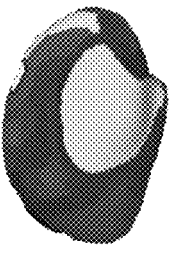
Figure 21A:
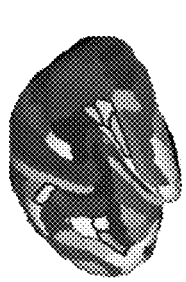
FIGS. 21A-21B are scans after fMRI guided TMS according to methods herein.
Figure 21B:
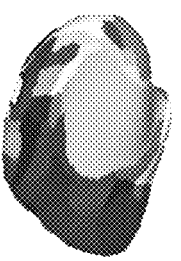
Figure 14A:
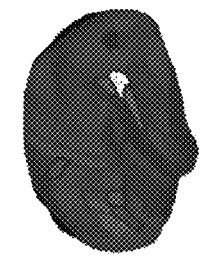
Figure 14B:
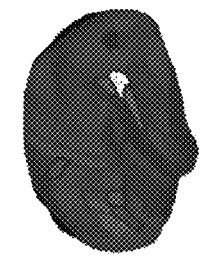

Embodiments include comparing each of the brain regions to each of the brain networks that does not include the brain region. As illustrated in FIG. 6A, a first region is selected to compare to all other networks. For example, $r=(r_{n=1}=1)$ from FIG. 4B, as indicated by the cross hatching of this region in FIG. 6B. That first region is then compared to the next network (n=2) by taking the difference of the covariation values from the information as determined from the algorithm described with respect to FIGS. 3A-4B. That same first region is then compared to the next network (n=3)

by taking the difference of the respective covariation values. Once the first region has been compared to all other networks, then the next region ($r=(r_{n=1}=2)$), is then compared against all other networks. The loop continues until all of the regions have been compared against all of the networks that does not include the region being compared. The loop continued until all of the regions have been compared against all of the networks, regardless of whether a region is included in a network or not. As illustrated in FIG. 6B, only the inner loop is illustrated in which $r=(r_{n=1}=1)$ has been compared to all other networks ($n_b=n_a+1=2$ to $n_b=N$).

After all of the comparisons above are determined, (network to network, region to region, and region to network), a statistical distribution may be created to obtain a first subset of regions and/or networks in which the differences from the above results (difference of covariation) is the lowest for the largest number of brain networks/regions and a second subset of regions and/or networks in which the differences from the above results (difference of covariation) is the highest for the largest number of brain networks/regions.

The first and second subset of regions and/or network are then compared against a healthy control group with the same age and/or gender as the patient. A third subset of regions and/or networks are identified from the first and second subsets where the regions that fall outside of a threshold from the mean of values of the covariation differences from the healthy group. For example, those regions that have corresponding covariation differences that are outside of (more or less than) two standard deviations from the mean of covariation differences from healthy individuals matching the same gender and age. The first threshold value may be within two standard deviations above a mean of the healthy control group, and the second threshold value may be within two standard deviations below the mean of the healthy control group. Matching a healthy control group may be against the patient based on a different range of parameters as would be understood by a person of skill in the art. For example, the comparison may be an exact match so that the gender and age of the patient is the same as those from the control group. The same age may be based on birth year. The comparison may also be on a range as would be understood by a person of skill in the art. For example, medical age groups are used in medical comparisons. Therefore, the same age may be the same age within the same age grouping. Exemplary age groupings may be 18-21, 22-35, 36-55, 56-65, 66 and older. Other groupings may also be used, such as for example, 18-24, 25-45, 46-65, and over 65. Other comparison ranges may also be used. For example, the same age based on birth year plus or minus a deviation, such as a year or five years. The matching may be based on ranges based on the condition and the changes a patient typically experiences based on the age range.

The first and second subset of regions and/or network also or alternatively may be compared against a healthy control group with the diagnosis/symptoms pre/post TMS treatment. A fourth subset of regions and/or networks are identified from the first and second subsets or from the third subset of regions and/or networks for those networks that are indicated as having the largest changes in covariation values from pre- to post-TMS treatment for the pool of patients with the same diagnosis and/or symptoms. In other words, an exemplary input to the system comprises a comparison pool of patient data in which the covariation difference before and after TMS is taken for each region and/or network of the patient's brain. The comparison pool also comprises the diagnosis and/or symptoms for the patient.

Each of the regions and/or networks from the third subset of regions is then compared to comparison pool to determine an associated difference of covariation of the respect region and/or network for the patients that have undergone treatment. The further subset therefore identifies those regions that are most likely to provide results for TMS treatment by having significant changes because of the TMS.

Embodiments may include comparisons of different features of an fMRI from different regions, networks, etc. of the brain. Relative comparisons may be used in which high, low, large, small, etc. are within the scope of the methods, systems, algorithms used herein. A person of skill in the art will understand the scope of these relative terms by referencing the purpose of the comparison and the relative values in the value set in which the relative term is used. For example, "high" compared to a data set may be 50% of the values in the higher end of the available range of data, or may be 75%, 80%, 90%, 95%, or other margin. A person of skill in the art will appreciate that the selection of the range may be informed by the purpose described in which the comparison is made. The relative term may be equal to, above, or below a set number (a threshold) or range as would be understood by a person of skill in the art based on the characteristic of the value, the purpose of the comparison, the function of the treatment or algorithm, the normal or average of a healthy control group, a range or one or more standard deviations away from normal or average of a data set for the characteristic (whether of a control group, healthy group, illness, comparison to other data within a data set, etc.). The setting of a threshold may be based on a statistical variation and/or in selecting a desired number of target locations for treatment.

An embodiment comprises a first input comparison control group comprising patient information including the patient's age, sex, gender, and/or other relevant diagnosis and/or treatment parameter. The first input comparison control group comprises a database of data from healthy patients comprising comparisons (differences) of covariation between region to region, region to network, and network to network. The first input comparison control group may then be used to compare the intra-subject outputs in order to determine those regions from the patient that are out of a desired range from those as compared to a healthy control group as represented by the first input comparison control group. The healthy control group may be compared on the same differences and regions with the largest difference from normalcy (the healthy group) are chosen as targets. In other words, if the patient generated a high covariation difference for region 1 from network 1 because of a comparison from region 1 from network 2, the healthy patients may be compared on that same difference (region 1, network 1 to region 1, network 2). Embodiments may also make comparisons based on individuals from the control group, averages over the control group (e.g., the healthy control group is averaged over all of the same region to network and region to region differences), or other basis of comparison.

An embodiment comprises a second input comparison control group comprising patient information including the patient's age, sex, gender, and/or other relevant diagnosis and/or treatment parameter. The second input comparison control group comprises a database of data from patients having the same symptoms and/or diagnosis where the data includes a covariation of each treatment region of the patient's brain compared before and after TMS treatment. In other words, the second input comparison control group comprises information about the changes that occur in regions of a patient's brain based on the application of TMS treatment to that region and the covariation is determined before and after the treatment to that region.

Embodiments may include comparing regions and networks of a patient's brain to other regions and networks. The comparisons may be performed in different ways. For example, as shown and described in the loops of FIGS. 3A-8B, each region may be compared against each other region, each network compared to each other network, each region compared to each network (without or without the network in which the region itself resides), or any combination thereof. In comparing a region to other regions, or to other networks, or networks to other networks, a combination of the other regions or networks may be in groups. For example, each region may be compared against each of the other regions individually, but also as a group. The comparison by a group may be by taking an average of the regions over the group of regions so that the comparison is being performed by a single region compared against a group of regions. A region is compared against a group of the other regions that occur within the same network. A region is compared against a group of the regions that comprise a network or a portion of a network, where the group of regions and the network are outside of the region or network in which the single region is located. The region is compared against a plurality of groups of regions so that the region is compared against all other regions of the brain.

The comparison of regions to regions, regions to networks, and networks to networks may not include all other regions and/or networks in a brain. The comparison of regions to regions comprise comparing regions to regions within the same network and/or regions outside of the same network. However, if portions of the brain are known to be functioning properly or not related to a given ailment or symptoms, then region(s) or network(s) may be removed from the comparison or regions and networks. However, it is still preferable to compare regions to other regions outside of the same network, networks to networks, or regions to networks outside of the network of the region for a more complete brain assessment for determining targeting of TMS treatments.

Embodiments may be used to treat various conditions. For example, embodiments may be used to treat various mental disorders, such as Alzheimer's disease, anxiety, obsessive compulsive disorder (OCD), PTSD, schizophrenia, cognitive impairment and other brain lesions, cognitive impairment caused by traumatic brain injury (TBI), insomnia, eating disorders, drug addiction, depression, attention deficit hyperactivity disorder (ADHD), attention deficit disorder (ADD), bipolar disorder, autism spectrum disorder, neurodevelopmental disorders and psychoses. Exemplary embodiments may also be used to reduce cognitive decline.

Embodiments of the present disclosure may be used with patients suffering from psychoses (auditory hallucinations). For example, FIGS. 9A-9F illustrates pre-TMS treatment, and FIGS. 10A-10F illustrates post-TMS treatment averaged across five patients suffering from Auditory Hallucinations (AH) psychoses in which the target brain regions identified for TMS treatment are outlined in bold lines. The illustrated images are from the covariation (amplitude to frequency) comparison of the BOLD fMRI data. The identified circuits for treatment according to the exemplary regions for treatment included in the Left Hemisphere: PGs, IP1, MIP, 7PL, VIP, IPS1, 10v 10r, 25, and the Right Hemisphere: 7PL, MIP, IP1, VIP, 7PC, OFC, pOFC, 25. As illustrated in FIG. 10A-10F, the circuits after TMS treatment are normalized. The patients experienced changes in their PANSS scores from severe (score of 6) to minimal (score of 2) in areas including P1Delusions, P2Conceptual disorganization, P3Hallucinatory behavior, P6Suspiciousness/presecution and P7Hostility. Patients were also able to reduce their medications to 50 percent after the time of their post-fMRI scan.

The scans of FIGS. 9A-10F are averaged over five patients suffering from Auditory Hallucinations (AH) psychoses so as not to disclose personal scans. As illustrated, the lighter areas of FIGS. 9A-9F were targeted for stimulation treatment and find improvement as illustrated in the improved areas illustrated in FIGS. 10A-10F.

Figure 13A:
FIGS. 13A-13B are a set of scans of a healthy control group matching the same age and sex as the patient.
Figure 13B:
Figure 12A:
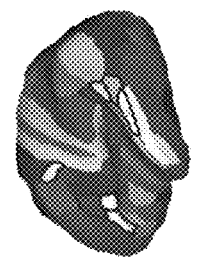
FIGS. 12A-12B are a set of scans after fMRI guided TMS according to methods herein.
Figure 12B:
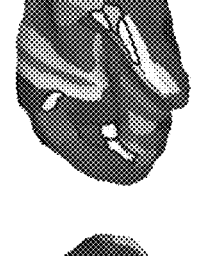
Figure 11A:
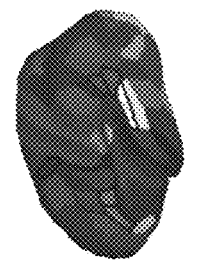
Figure 11B:
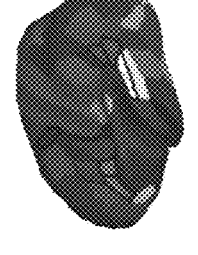

Embodiments of the present disclosure may be used for patients suffering from TBI. For example, FIGS. 11A-11B illustrates an exemplary baseline RSFC area map pre-TMS treatment according to embodiments, with FIGS. 12A-12B illustrating an exemplary RSFC map after the fMRI guided treatment. FIGS. 13A-13B illustrates an exemplary control group having the same age and sex as the patient from FIGS. 11A-12B. The illustrations are averaged over 5 exemplary subjects for the sake of illustration. The RSFC analysis according to exemplary methods described herein was run on five patients. The exemplary embodiments may identify circuits for treatment with TMS including the following regions within the language network for stimulation: Left Hemisphere: STSdp, TPOJ1, STV, SFL, 55b, 44, 45. Exemplary embodiments of the treatment protocol were excitatory, at 130% amplitude of individual motor threshold. The patients experienced symptoms including limitations of language production (speech comprehension, articulation and speed) and language comprehension (semantic processing) from severe (score 6) to mild (score 3). Exemplary maps provided for different RSFC areas are provided for example. See FIGS. 11A-31B.

A sudden blow or jolt to the head could cause TBI. Functional damage of these injuries has been investigated specifically in intrinsic connectivity networks (ICNs). TBI substantially disrupts ICN function associated with cognitive impairment. The two primary ICNs, the salience network (SN) and the default mode network (DMN) are believed relevant to treating TBI. In addition to the above findings, it is believed that the efficacy of standard TMS in treating TBI could be substantially improved by arming it with a guiding system based on brain networks.

Resting-state functional connectivity MRI (rsFC MRI) is an imaging technique capable of revealing the brain networks and the dynamics of their interaction. Embodiments may use rsFC MRI to visualize each patient's brain networks. RsFC MRI maps may also be used to find appropriate targets that will "normalize" the brain network's function and interaction with other networks. This is an effective way of treating TBI disabilities since, e.g., activity of ICNs is normally tightly coupled, which is important for attention control. The ability to restore the normal activity of ICN could reverse the loss of tight coupling of ICN as a result of damage to the structural connectivity of these networks. Loss of normal correlation between networks may produce abnormalities of network function and cognitive control.

Conventionally, the patient or those near the patient are required to provide symptoms in order to determine the severity of TBI. In some instances, physical detection may be made through structure lesions in the brain. The brain suffering neurological death will show lesions in the form of volume loss of the brain tissue at the structurally damaged areas of TBI. Essentially, these areas have no connectivity to other areas of the brain. Structural lesions can be detected through methods, systems, and instructions described herein through the comparison of rsFC MM comparisons by identifying areas that have no functional connectivity with a large number of brain areas to suggest a global effect. Other methods descried herein may use structural analysis to identify total cortical gray matter volume and white surface total area for identifying structural changes associated with TBI. Embodiments may be used to provide alternative diagnosis pathways for identifying structure lesions decoupled from the physical detection through brain tissue loss.

The systems, methods, and instructions provided herein may also be used to diagnose brain injuries that will lead to structural lesions before neurological death so that the brain areas may be treated or in which injury may be reduced. For example, The systems, methods, and instructions provided herein may identify functional lesions. A functional lesion may be an area of the brain that is functionally disconnected from a large number of brain areas; but may not yet be zero or may not have undergone physical loss. Areas with functional lesions may show an erratic or paroxysmic behavior, having a high and negative correlation/covariation less than zero. For example, one region as compared to other regions of the brain using rsFC MRI may show high and negative correlations so that one area is identifying as having very highly negative correlation to other areas of the brain. In this instance, the brain area may be considered as a functional lesion that, if left untreated, will have a high potential or likelihood to result in structural lesions and/or neurological death of the brain area.

In functional lesions, a global disruptive behavior by deactivating other brain regions with which they are negatively correlated may be detected. Functional lesions regions are highly negatively correlated; meaning that in an attempt to reconnect itself with the rest of the brain, the region deactivates a large number of brain regions, shutting down regions to which it is negatively correlated. High and negative correlation/covariation with a large number of brain regions may be used to identify functional lesions; these high and negative correlations/covariations are less than zero and show a large-scale decoupling effect (deactivation of a large group of brain regions).

The systems, methods, and instructions may therefore include early stage diagnosis and treatment options for detecting areas in jeopardy of brain damage before structure detection is evident or available. Using the fMRI to compare functional connections of brain areas, the systems, methods, and instructions may provide early detection of future brain injury by identifying areas of the brain that are functionally disconnected, but which have not yet experienced neurological death and/or physical deterioration. Embodiments may therefore provide early detection in order for treatments to intercede before neurological death, to limit damage, and/or to reverse damage.

Figure 20A:
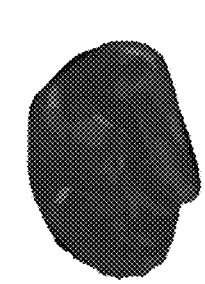
FIGS. 20A-20B are a set of scans at baseline showing target treatment areas at RSFC area SFL.
Figure 20B:
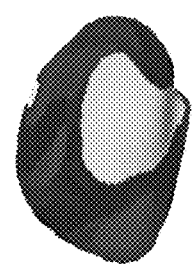
Figure 19A:
FIGS. 19A-19B are scans of a healthy control group matching the same age and sex as the patient.
Figure 19B:
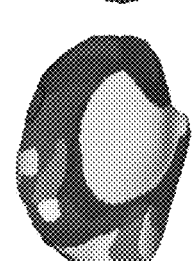

Embodiments may therefore be used to diagnose and treat TBI. Embodiments may not need to rely on the patient's physical symptoms or physical brain lesions to diagnose the severity of TBI. Embodiments may be used for early detection and/or treatment before brain damage or before significant brain damage or before neurological death. The structural lesion may have zero functional connectivity, or nearly zero connectivity with many brain regions, including, reduced, or near zero functional connectivity. FIGS. 19A-20B illustrates brain scans for a patient having experienced a stroke. FIGS. 19A and 20A illustrate images from an fMRI brain scan for patients experiencing a stroke showing close to zero functional connectivity. FIGS. 19B and 20B illustrate the corresponding image to show the corresponding structural degradation. The patient scans show no correlation/covariation with a large group of brain regions. The exemplary embodiment shows correlation/covariation values of 0 or close to 0.

In stage 1, prior to neuronal death, correlation/covariation may be less than zero with a large number of brain regions, indicating global decoupling effect, deactivating a large number of brain regions and categorized as functional lesions. In stage 2, when brain damage is usually present, correlation/covariation is near or at zero with a large number of brain regions, showing a pattern of global non-connectivity for structural lesions. The change in connectivity of an area to identify TBI may be according to the embodiments described herein in which an area of the brain as compared to all other areas of the brain stands outside a statistical deviation from the rest as having a low functional connection as a structural lesion or a high and negative correlation as a functional lesion. The comparison may also or alternatively be based on other patients that have been diagnosed and treated for TBI.

Embodiments of the methods may use advanced techniques to model brain dynamics to get insight into network dysfunction. For example, embodiments may use rsFC MRI to find out how structural network damage caused by axonal injury produces functional irregularities, which may be used to determine targets for TMS treatment. As another example, embodiments may detect "functional lesion(s)" to detect and/or treat brain areas in certain patients with TBI that are not detected structurally. Embodiments may be used to identify "lesions" when the brain area has not materialized structurally in the form of volume loss (neuronal death). By early treatment provided by early detection, structural damage may be limited, stopped, or even reversed by treating these early diagnosed lesions.

Embodiments herein may be used to identify structure lesions by finding areas of the brain without functional connection to other areas of the brain. In this instance, these areas of the brain may be targeted and/or eliminated from treatment. For example, these areas may be removed from the algorithms herein as the brain area may have already experience neurological death and therefore would not be receptive to treatment. Without removing these areas from selection, they may be identified through the above algorithms based on the criteria above as their dysconnectivity may identify these areas as preferred treatment areas. In other instances, if neurological death has not yet occurred, these areas may be highly desirable to treat before such physical damage is completed or continued. The pattern of connectivity of structural lesion versus functional lesion is very different.

Figure 18A:
FIGS. 18A-18B are scans after fMRI guided TMS according to methods herein.
Figure 18B:
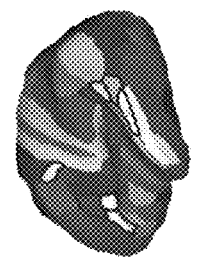
Figure 17A:
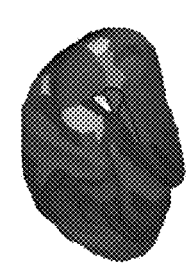
FIGS. 17A-17B are a set of scans at baseline showing target treatment areas at RSFC area STV.
Figure 17B:
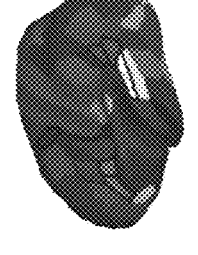

Embodiments of the fMRI-guided TMS treatments herein may be used to treat functional lesions that may result from TBI. Brain maps of functional lesions are usually very abnormal (erratic or paroxysmic behavior of neurons), usually with high and negative correlation/covariations with a large number of brain regions showing a global effect. Usually, these maps are very colorful in the negative end of the spectrum, i.e., light blue, green, purple, grey, etc. These lesions can fully recover or improve their function when these areas are targets with TMS treatments. FIGS. 18A-18B illustrates a frontal polar cortex (area TE1m, right) having a high negative correlation/covariation with a large group of brain regions (light blue and green areas). FIG. 18A illustrates a patient at baseline; and FIG. 18B illustrates a patient after treatment according to embodiments described herein.

Embodiments of MRI-guided TMS treatments herein may be used to treat structural lesions that may result from TBI.

Brain maps of structural lesions are usually non-colorful, i.e., dark red or brown, almost black, showing lack of connectivity with a large number of regions. In some instances, some activity may still be detected in these areas. If so, then these areas may partially recover their function after treatment with TMS.

Patients with TBI might show either or both type of function and/or structural lesions. Embodiments herein may be used to treat either or both with fMRI-guided TMS. Embodiments of the present disclosure may be used for patients to reduce further damage from TBI or reduce brain damage from functional disconnectivity. Embodiments herein may be used to provide early-stage diagnosis and treatment of brain areas prior to structural brain damage by identifying and/or treating functional lesions.

Embodiments of the present disclosure using fMRI may allow early detection of brain abnormalities prior to behavioral or structural manifestations (i.e., imaging-based biomarkers) for prevention and early interventions in neurological and psychiatric conditions. Embodiments may also allow interventions in later stages of the disease/condition when cortical atrophy and volume loss are present by: (1) recruiting healthy brain regions in affected pathways to compensate for function loss and; (2) stimulating atrophic areas to delay further deterioration and progression of the disease (when applied to neurodegenerative diseases like in Parkinson or Alzheimer's disease, where conditions get worse over time).

Embodiments may show and describe methods of identifying brain regions having high negative correlation and covariation with a large group of brain regions. These types of functional lesions can be detected in any brain region. The embodiments illustrated herein show single case scenarios for illustration. See FIGS. 99A to 127. Embodiments may be used to help prevent late complications of TBI, such as Alzheimer's disease and chronic traumatic encephalopathy. This may be due to the fact that axonal injuries could interact with neuroinflammation and neurodegeneration contributing to the formation of chronic complications. Embodiments may use network-level imaging to inform diagnosis, prognosis, and treatment planning for TBI.

Embodiments of the present disclosure may be used for patients to reduce or prevent cognitive decline based on aging. For example, FIGS. 32A-32D illustrate a baseline RSFC area map pre-TMS treatment, with FIGS. 33A-33D illustrating an RSFC map after the fMRI guided treatment. FIGS. 34A-34D illustrate a control group having the same age and sex as the patient from FIGS. 32A to 33D. The illustrations are averaged over five (5) subjects for the sake of illustration. The RSFC analysis according to methods herein was run on five patients. The embodiments herein identified circuits for treatment with TMS including the following regions within the frontoparietal and language networks for stimulation: Left Hemisphere: p9-46v, STSdp, TPOJ1. Embodiments of the treatment protocol were excitatory, at 130% amplitude of individual motor threshold. Patients were asymptomatic at the time of TMS treatment, so no change in symptomatic score was produced. The patients were selected for their risk factors for neurodegenerative diseases (cardiovascular and genetic predisposition). Exemplary maps provided for different RSFC areas are provided for example. See FIGS. 32A to 38D.

Aging can cause cognitive impairment, such as impairments caused by vascular degradations. Vascular cognitive impairment (VCI) is caused by blockage of micro vasculatures; and the inability to supply oxygen and nutrients to different brain regions causes a decline in cognition. Sometimes, this inability is caused by cerebrovascular injury. In addition to vascular-based dementia there is also degenerative dementia (which is most common in Alzheimer's disease). Combining these two types, covers the majority of cases of dementia.

TMS can be used to prevent cognitive decline by strengthening brain activity and connectivity in most vulnerable regions, like specific locations within the frontal and temporal lobes detected by our fMRI-based biomarkers. The methods herein may be successful in treating MCI patients using MRI guided TMS approach. Embodiments may also be used to develop a new protocol for preventing or reducing the decline of everyday memory in asymptomatic patients with risk of MCI and Alzheimer's disease, due to family history or cardiovascular disease.

Embodiments of a protocol may involve: (1) the analysis of resting state fMRI (rsfMRI) images taken of the patient's brain to construct brain networks, (2) the use of biomarkers to detect most vulnerable brain regions in each individual, and (3) the delivery of MRI guided TMS over a course of 20 sessions. Patients may receive a second MRI after the last session to compare baseline and post-treatment brain maps to calculate the efficacy measure. Patients may also receive another MRI at one-year follow-up to monitor evolution of brain activity and connectivity, and the need of another cycle of 20 sessions with MRI guided TMS may be assessed by biomarkers, and delivered as needed over the course of the lifespan. The methods herein for use with MCI patients suggest that MRI guided TMS could be an effective therapy for preventing cognitive decline and probably a tool to delay deterioration.

Embodiments of the present disclosure may be used for patients suffering from depression. For example, FIGS. 41A-41D illustrate a baseline RSFC area map pre-TMS treatment according to embodiments herein, with FIGS. 42A-42D illustrating an RSFC area map after the entire circuit based fMRI guided treatment according to embodiments herein. FIGS. 43A-43D illustrate an RSFC area map after a single region treatment of area 46 within the DLPFC according to conventional treatments. FIGS. 44A-44D illustrates an RSFC area map from the healthy control group matching the same age and sex as the patient from FIGS. 41A to 42D. The illustrations are averaged over ten (10) subjects for the sake of illustration. The RSFC analysis according to methods herein was run on ten patients with depression who did not respond to standard TMS approaches based on the 5-cm rule. The embodiments herein identified circuit including the following regions within the cingulo-opercular network for stimulation: Left Hemisphere: 46, PF; Right Hemisphere: 46, PF. Embodiments of the treatment protocol were excitatory, at 120% amplitude of individual motor threshold. Change symptomatic depression scores based on HAMD included starting from a baseline score of HAMD<7 in all subjects, remission after circuit-based fMRI-TMS, and HAMD>7 in all subjects after the single-region fMRI-TMS, where 50% improvement was achieved in HAMD scores in all subjects but none achieved remission. None of the patients included in these analyses responded to standard-TMS (5-cm rule). Exemplary maps provided for different RSFC areas are provided for example. See FIGS. 41A-7A-1 to 56D.

Major depression disorder (MDD) may be characterized by abnormal functional connectivity of brain networks. Research has revealed disrupted network connectivity in main MDD networks, i.e., default mode network (DMN), the central executive network (CEN), and the salience network (SN). There have also been reports of abnormality in cerebellar and thalamic circuits. The methods may deal with the qualitative aspects of the symptomatology of MDD using a unique tool (resting-state functional connectivity MRI or fMRI) that is capable of revealing alterations in the brain networks.

Embodiments herein may be used to identify the severity of depression with the alterations found in the DMN, CEN, SN, frontal and thalamic brain regions, insula, and the subgenual anterior cingulate cortex (sgACC). One reason that standard TMS does not produce very high outcomes is due to its inability to treat targets unique to each patient. Embodiments described herein may measure the patient's brain function and connectivity shortly before treatment begins, and using a sophisticated algorithm, identify specific brain regions that show abnormal behavior.

Embodiments may be used to show a clear functional connectivity involvement in MDD that is associated with its pathophysiology and treatment. However, embodiments of the use of fMRI enables embodiments of the method described herein to find targets, deliver treatments and assess their efficacy upon completion of treatment. Implementations of functional connectivity as a scientific biomarker may increase the chances of addressing the root cause of MDD. Just like any other disorder, diagnosis of the brain regions involved in depression in order to target them is important. Using fMRI, the methods described herein may find the brain regions which are not functioning normally. Exemplary fMRI-guided TMS protocols of depression of embodiments described herein may identify and treat these specific regions, most famously called the DLPFC. We have found decreased activity and abnormal connectivity in the left DLPFC of depressed patients; and this area is associated with behavioral dysregulation common in depression (e.g., decreased energy, insomnia, appetite changes).

The involvement of subgenual anterior cingulate cortex (sgACC) in the pathophysiology of depression and as a predictor of response is also shown. DLPFC hypometabolism might be secondary to limbic hyperactivity, and that DLPFC connectivity (negative correlation) with limbic regions are responsible for antidepressant response. It may be that optimal targets for TMS fall broadly within the sgACC "anticorrelated" region of DLPFC2-4. When a patient is depressed, there are certain areas in the brain that may be affected, for example, the dorsolateral prefrontal cortex, the hippocampus, amygdala, the lateral orbitofrontal cortex, the anterior cingulate cortex, and the posterior, the parahippocampal gyms, the insula, the temporal cortex, and the precuneus are all regions visualized and treated according to embodiments of regions and networks analyzed according to the method described herein for depression treatment. When blood flow and connectivity in these areas is outside the norm, further investigation may confirm that there is an area that is over-or under-functional and/or structural and that the functional and/or structural connectivity may be increased or decreased. By setting the TMS coil to deliver magnetic pulses in these specific areas at a specific frequency to target the circuitry there, then the specific regions of the brain integral to the symptoms can be brought back into proper function and the patient can feel joy again.

Systems and methods described herein may be used for patients suffering from autism spectrum disorders. For example, FIGS. 57A-57D illustrate a baseline RSFC area map pre-TMS treatment, with FIGS. 58A-58D illustrates an RSFC map after the fMRI guided treatment. FIGS. 59A-59D illustrate an exemplary control group having the same age and sex as the patient from FIGS. 57A-58D. The illustrations are averaged over 5 exemplary subjects for the sake of illustration. The RSFC analysis according to methods was run on five patients. The embodiments identified circuit for treatment including the following regions within the default and language networks for stimulation: Left Hemisphere: STGa, STSda, STSva, STSdp, STSvp. Embodiments of the treatment protocol were excitatory, at 110% amplitude of individual motor threshold. The patients experienced symptoms including limitations of social interaction, social communication, theory of mind starting at severe (score 6) and improved to mild (score 3) in all subjects. Exemplary maps provided for different RSFC areas are provided for example. See FIGS. 57A-71D.

Autism in DSMS is characterized as one of the so-called pervasive developmental disorders (PDD) which also includes Asperger's disorder and other pervasive developmental disorders not hereto specified. These groups of disorders are collectively called autism spectrum disorders (ASD). ASDs are characterized by impairments in social skills, repetitive behavior, and the communicative use of verbal and nonverbal language. Children with restricted and repetitive behavior share features such as intricacies of behavior and the inability to grasp concepts. ASD affects about 1 in 60 children, but there are currently no pharmaceutical treatments that can target the core networks implicated in ASD.

Recent evidence shows that repetitive transcranial magnetic stimulation (rTMS) holds high potential to alleviate the main symptoms of individuals with ASD. Individuals with autism have a Unique Brain Complexity. There is strong evidence that rTMS improves symptoms in young people with ASD. Our experience indicates that rTMS applied to DLPFC that is targeted to individual regions specific to the individual based on the embodiments described herein has efficacy as a novel intervention for EF deficits in ASD. By leveraging the methods of rsFC MRI technology described herein, TMS can be administered in a targeted and individual way to the patient with the capability to directly treat malfunctioning regions and acquire pre-/post-treatment neuroimaging measures, to document the effect of treatment on brain structures that are essential for EF performance. Embodiments of this capability allows us to examine the neural mechanisms for rTMS treatment efficacy. Embodiments may also include a longitudinal follow-up that enables assessment of the need for ongoing intervention to maintain treatment effects.

As in depression, the standard rTMS in ASD uses the site of treatment based upon fixed location relative to the motor cortex. Since autism is a disorder of the association cortex, and in particular, a disorder of connectivity that primarily involves intra-hemispheric connectivity, for treating ASD a connectivity-based targeting strategy for TMS would be to identify optimal TMS target coordinates in the bilateral DLPFC. Our prior experience suggests that in ASD with a predominance of social-cognitive malfunctions, embodiments of the method provided herein enables: (i) measurement changes in resting-state functional connectivity (rsFC) between nodes of involved networks, e.g., Theory of Mind (ToM) network of prefrontal cortex, orbitofrontal cortex, supplementary areas, anterior cingulate cortex, posterior cingulate, superior temporal cortex, superior/middle temporal gyms and inferior parietal lobe regions, with the culprit deep nuclei regions, e.g., ventral anterior nucleus of the thalamus. Such comparisons yield correlations that mediate treatment response; and (ii) a connectivity-based targeting approach applied at the single-subject level to identify optimized bilateral targets in the prefrontal cortex for TMS to individualize therapy. We, therefore, offer a novel, innovative approach with enhanced efficacy TMS guided by rsFC MRI.

This approach is fundamentally different from traditional approaches that target without looking into a patient's brain or understanding differences in brain organization. Instead, embodiments described herein stimulate the brain based on the individual brain's rsFC pattern. Embodiments described herein emphasize the network architecture of the human brain and as such use rsFC MRI to construct the networks implicated in each disorder. Concerning ASD, evidence such as the generalized dysfunction of the association cortex with sparing of primary sensory and motor cortex and white matter, combined with the absence of clinical signs of focal brain dysfunction, common in children with hypoxic-ischemic injury and cerebral palsy, such as visuospatial deficits, points to a distributed neural systems abnormality. This is why our treatment is based on networks. Others have used EEG-based functional connectivity to guide their TMS treatment of ASD. In comparison, results after administering a TMS treatment protocol using methods described herein indicate that patients under an anatomically precise technique would experience longer-lasting clinical improvements.

The systems and methods herein may be used for patients suffering from dementia. For example, FIGS. 72A-72D illustrate a baseline RSFC area map pre-TMS treatment according to embodiments described herein, with FIGS. 73A-73D illustrates a baseline map after the fMRI guided treatment according to embodiments described herein. FIGS. 74A-74D illustrate an exemplary control group having the same age and sex as the patient from FIGS. 72A through 73D. The illustrations are averaged over 5 exemplary subjects for the sake of illustration. The RSFC analysis according to exemplary methods described herein was run on five patients. Circuit were identified for targeted TMS treatment according to embodiments described herein including the following regions within the cingulo-opercular, somatomotor, default, frontoparietal and dorsal attention networks for stimulation: Left Hemisphere: semantic retrieval: lexical retrieval: FOP5, FOP4, FOP3, FOP2; TE1a, TE1m, TE1p, PHT, TE2a. The treatment protocol were excitatory, at 130% amplitude of individual motor threshold. The patients experienced symptoms including improvements in retrieval of lexical/semantic information starting from moderate severe (score 5) improving to mild (score 3) in all subjects. Exemplary maps provided for different RSFC areas are provided for example. See FIGS. 72A-98D.

Embodiments described herein are believed to be effective at halting, slowing, and/or reversing the effects of Alzheimer's Disease (AD). To date, pharmacological treatments have not obtained favorable results and that has created room for non-pharmacological interventions to be used for this disease. TMS can induce changes in brain activity and cause long-term modifications in impaired neural networks. Such capabilities of TMS hold many promises for clinical intervention. Standard TMS can cause changes in cortical excitability, increases brain plasticity, and facilitates the recovery by the reorganization of impaired neural networks responsible for cognitive impairment. However, standard TMS does not offer individualized targeting capabilities that can be rectified by using advanced MRI techniques. The methods described herein use fMRI to map the entire brain networks and then run a special analysis for each patient to find the right target for TMS treatment with the largest outcome.

As fMRI according to embodiments described herein may be used as a technique to produce biomarker-surrogate for neurodegenerative diseases. It may identify the presence of AD and allow for tracking progression, severity, guide TMS treatment, and offer an assessment of treatment effects. Growing evidence shows that interventions in neurodegenerative disorders must be applied in early or even pre-symptomatic phases of AD. As such, the use of a sensitive technique like fMRI for monitoring disease progression based on quantitative measures combined with clinical features offers a reliable and easy-to-track biomarker in this field.

Embodiments described herein may be used to restore a patient's foundation and reduce or recover from anxiety, such as Generalized Anxiety Disorder (GAD). The fMRI technology and methods described herein may bring clarity to a patient's treatment plan by allowing insights into how the individual patient's brain is working.

The unique combination of network-focused TMS and fMRI according to embodiments described herein may help patients find relief from anxiety, depression, and many other disorders of the brain. Simply put, the MRI images described herein and associated methods of analyzing the MRI images may help identify unique brain function to create a treatment plan unique to the patient. As described herein, fMRI measures brain activity by detecting changes associated with blood flow, and dMRI uses computational tractography to produce three-dimensional trajectories through the white matter within the brain volume. When an area of the brain is in use, blood flow to that region increases. Since several parts of the brain are key factors in the production of fear and anxiety, the fMRI helps identify the areas affected in the patient's brain. Embodiments illustrated herein show anxiety circuits. Two types of brain circuits show two different biomarkers for anxiety including frontal lobes or parieto-occipital sulcus. Some patients have both features and some patients are more inclined to frontal or parieto-occipital circuits.

For example, FIGS. 128A-128D illustrate a baseline RSFC area map pre-TMS treatment according to embodiments described herein, with FIGS. 129A-129D illustrate an RSFC map after the fMRI guided treatment according to embodiments described herein. The illustrations are averaged over five subjects. The RSFC analysis according to methods described herein was run on five patients. The embodiments described herein identified circuits for treatment with TMS including the following regions within the frontoparietal, cingulo-opercular and default mode networks for stimulation: right hemisphere: dorsolateral prefrontal, area 9-46d, right. The treatment protocol were inhibitory, at 90-100% amplitude of individual motor threshold (adjusted by penetration depth and type of coil used). The patients experienced psychological/physiological anxiety and panic attacks from a severe score of 6 to a minimal score of 2. Exemplary maps provided for different RSFC areas are provided for example. See FIGS. 128A through 137D

For example, FIGS. 138A-138D illustrate a baseline RSFC area map pre-TMS treatment according to embodiments described herein, with FIGS. 139A-139D illustrating an SFC map after the fMRI guided treatment. The illustrations are averaged over five subjects. The RSFC analysis according to methods described herein was run on five patients. Embodiments described herein identified circuits for treatment with TMS including the following regions within the frontoparietal, default mode and cingulo-opercular networks for stimulation: left hemisphere, parieto-occipital sulcus areas, area POS2, left. Embodiments of the treatment protocol were inhibitory, at 90-100% amplitude of individual motor threshold (adjusted by penetration depth and type of coil used). The patients experienced psychological/physiological anxiety and panic attacks from a severe score of 6 to a minimal score of 2. Exemplary maps for different RSFC areas are provided. See FIGS. 138A through 147D.

The systems and methods described herein may be used to treat bipolar disorder, also known as manic-depressive illness, which is a brain disorder that causes unusual shifts in mood, energy, activity levels, and the ability to carry out day-to-day tasks. Types of bipolar disorder include Bipolar I Disorder, Bipolar II Disorder, Cyclothymic Disorder, and Other Specified and Unspecified Bipolar and Related Disorders.

With fMRI imaging according to embodiments described herein, the network(s) not functioning properly that causes manic episodes to occur can be identified. With this technology, methods according to embodiments described herein may treat the specific areas precisely with a personalized treatment plan and precise neuronavigation.

Embodiments described herein may be used to treat ADHD. Attention-deficit hyperactivity disorder (ADHD) is a disorder characterized by persistent and inappropriate levels of over-activity, impulsivity, and inattention.

Two partially segregated attention networks may be involved in ADHD: the dorsal attention network (DAN) and the ventral attention network (VAN). Both networks are deeply involved in the attentional regulatory systems in the brain. The DAN is centered in the bilateral intraparietal sulcus (IPS) and the junction of the precentral and superior frontal sulcus (frontal eye fields, FEF), and enables the control of spatial attention by selecting sensory stimuli based on internal goals or expectations, and linking these goals to the appropriate motor responses. One of the major symptoms of ADHD, i.e., failure to ignore extraneous stimuli, is associated with the loss of functional connection (FC) in the DAN. The VAN is anchored in the right temporo-parietal junction (TPJ) and the ventral frontal cortex (VFC), and reorients attention to salient behaviorally relevant stimuli. In this regard, fMRI studies of ADHD have revealed a significant hypo-activation in the VAN and DAN compared with that in healthy controls, which is related to ADHD.

While task-based fMRI studies have made an important contribution to the understanding of brain function in ADHD, resting-state fMRI studies have also revealed hypo-connectivity in the DAN and VAN in children and adults with ADHD. Therefore, the network cause of ADHD may be related to hypo-connectivity in the attention networks, including the DAN and VAN.

Treatments according to embodiments described herein may be guided by resting-state fMRI and not task-based fMRI because the way a network responds to external stimuli (task-based studies) depends on the brain network's connectivity at rest (resting-state fMRI studies). As such, through computational mappings according to embodiments described herein, the method can identify and modulate the way these networks respond when engaged in attention demanding tasks. Moreover, resting-state fMRI may be easier to implement, allowing the identification of functional brain networks with greater sensitivity than task-based fMRI.

Systems and methods herein may be used to treat drug addiction. Imaging studies have discovered specific networks that cause the three stages of the addiction cycle. The main components of the networks are centered around the ventral tegmental area and ventral striatum for the binge stage. The structure that plays a dominant role in the withdrawal phase is the amygdala.

A number of networks are involved in the anticipation stage: Craving is controlled by the cingulate gyms, orbitofrontal cortex, dorsal striatum, prefrontal cortex, amygdala, and hippocampus; Loss of inhibitory control is caused by malfunctioning of the insula, the dorsolateral prefrontal, and inferior frontal cortices.

A sequence of neuroplasticity events from the ventral to the striatum and orbitofrontal cortex cause dysregulation of the prefrontal cortex, cingulate gyms, and amygdala, governing the transition to addiction. The identification of the neural networks involved in the transition stages of addiction have also offered insight into the vulnerability to developing addiction.

The underlying mechanism of TMS-induced effects that makes it an effective treatment for SUD patients is that it modulates the maladaptive brain networks of addiction. Embodiments of the methods described herein may use this network-level action supported by many preclinical and clinical findings to develop an even more effective TMS technique, including using resting-state functional connectivity MRI or fMRI guided TMS.

The methods described herein include mapping the brain networks and then using network analysis anchored on the deep brain regions implicated in addiction. This allows the methods described herein to determine a counterpart to the nodes on the malfunctioning network in the cortex which will become targets of neuronavigation-guided TMS treatment.

Embodiments described herein may also include fMRI to assess the severity of the addiction, as well as to guide the TMS treatment. This fMRI-guided TMS is a state-of-the-art, highly complex technique that uses infrared technology to precisely target the affected structures in the brain. Through this technique, embodiments described herein may offer multiple targets to apply TMS, which is highly effective in smoking and substance use cessation.

Upon completion of the treatment, the method may also include the use fMRI for objectively assessing the treatment effects. fMRI may be complemented with evidence-based self-help intervention, cognitive-behavioral interventions, and nicotine/substance replacement therapy. The major advantage of fMRI is that it directly engages the dysregulation of motivational networks.

Since such dysregulation is caused by heightened incentive salience and habit formation, reward deficits, and compromised executive function in three stages, it engages the networks identifiable by fMRI and accessible by TMS. It is established that rewarding effects of the substance—such as the development of incentive salience and drug-seeking habits in the binge stage—involve changes in dopamine and opioid peptides in the basal ganglia. Since direct stimulation of basal ganglia is not possible by TMS due to the weak intensity of its electric field in the deep brain regions, targeting secondary regions of subcortical areas anatomically connected to the DLPFC is only possible through the information that fMRI provides.

The analysis of fMRI according to embodiments described herein may find regions within the left DLPFC that can be used as target areas for treating SUDs.

Embodiments may also be used in reducing drug consumption.

Embodiments described herein may apply the same strategy in treating negative emotional states. Negative emotional states in the withdrawal-effect stage are caused by decreases in the function of the dopamine component of the reward system, and recruitment of brain stress neurotransmitters such as corticotropin-releasing factor and dynorphin. In the amygdala network, seed-based calculations may be used to find effective cortical targets by fMRI to increase the efficacy of TMS in treating negative emotional states.

Similarly, the same approach may be used to suppress the craving and deficits in executive function in the anticipation stage. Here, TMS targets are selected using fMRI knowing that this stage involves the dysregulation of afferent projections from the prefrontal cortex and insula, including glutamate, to the basal ganglia and extended amygdala. As such, the system, methods, and algorithms have been very effective in the treatment of addiction.

Embodiments described herein are believed to assist in eating disorders (EDs). fMRI TMS according to embodiments of the method described herein may be used to identify and correct the network(s) causing an eating disorder.

Eating palatable food increases activation in regions involved in reward such as the ventral and dorsal striatum, midbrain, amygdala, and orbitofrontal cortex. Increased or decreased functional resting-state connectivity has also been observed in EDs compared to controls, implicating networks associated with executive function, reward processing, and perception. Choosing low-fat vs. high-fat foods increases connectivity between dorsal caudate and DLPFC regions in patients with AN, which is implicated in actual food intake eaten, thus making the DLPFC a region of considerable interest.

By identifying the underlying network associated with the disorder through fMRI imaging and the embodiments described herein, the biological side of this disorder can be treated.

Embodiments described herein may be used to treat OCD.

Neuroimaging studies have provided strong evidence that OCD involves neural circuits. The most viable candidate for the culprit network in the pathophysiology of OCD is cortico-striato-thalamo-cortical (CSTC) circuits.

CSTC networks are believed to be involved in multiple cognitive functions such as inhibition of impulsive behavior, modulation of motor activity, and assignment of attention. Imaging studies have also shown that CSTC circuits have several interconnected circuits involving fronto-cortical and subcortical brain areas. These pathways oppose each other, giving the thalamus either: an inhibitory function causing reduction of movement through activation of the indirect pathway, or net excitation causing an increase of movement by activating the direct pathway.

Different CSTC networks are responsible for determining specific motor and cognitive functions. These selections are made by the specific fronto-cortical area included in the network.

The relationship between fronto-cortical areas and the basal ganglia may determine which actions are selected and which are suppressed. Stimulation or inhibition of appropriate behavior sequences depends on the change in the balance of activity between direct and indirect pathways. Failure in eliminating dysfunctional behavior sequences causes OCD symptoms.

OCD patients may have dysfunction in the core neural processes performed by CSTC circuits, e.g., response inhibition and sensorimotor gating. This means that patients with OCD are biased to perform habits at the expense of goal-directed actions. It is possible that different populations of striatal neurons differentially regulate the direct and indirect basal ganglia pathways, causing stereotypic motor behaviors.

The direct pathways (i.e., striatum, substantia nigra, globus pallidus interna) and indirect pathways (i.e., striatum, subthalamic nucleus, globus pallidus externa) may contribute to thalamic communication with the cortex and in the generation of motor patterns. This understanding explains why OCD symptoms may be caused by excess activity in direct versus indirect OFC-subcortical networks. fMRI may be used to detect the activity of the whole brain with special attention for the involved networks in OCD. The method may then be used to determine the targets specific to each individual patient based on the malfunctioning of different regions. These targets that vary amongst patients will then be treated by TMS for normalizing the functioning of the involved networks.

Embodiments described herein may be used to treat PTSD, which is an incapacitating condition with symptoms of nightmares or flashbacks, avoidance and hyperarousal following traumatic experiences.

The methods described herein including fMRI may be used to assess the role of three fundamental brain networks, namely the default mode network (DMN), central executive (CEN), and salience (SN) in the understanding of higher cognitive functioning. Hence, the technique that can address the issue of impairment of the functioning of these networks has the opportunity to make a big difference in PTSD. In spite of the success of standard TMS in treating PTSD, the fact that neural networks are not affected homogeneously calls for opting for a personalized treatment. Some embodiments of the disclosed method use resting-state functional connectivity MRI (rsFC MRI) as the guide to personalize TMS therapy.

Embodiments may include fMRI-TMS at a wide range of frequencies 1-20 Hz rTMS to theta burst (continuous/intermittent TBS) on specific targets in the right and/or left DLPFC. iTBS is a high-frequency rTMS that delivers brief trains of high-frequency pulses (50 Hz). The train is delivered at a 5 Hz frequency (every 200 msec), which is within the theta range of EEG [4-7 Hz]. iTBS may be used for its many advantages such as its ability to deliver effective treatments in 3 min, compared with the 37-min standard protocol for depression.

Embodiments described herein may be used to treat schizophrenia. TMS has been used for treatment of schizophrenia. A version of TMS called deep TMS or dTMS has shown significant improvements in negative symptoms when administered to the DLPFC in schizophrenia. In this case, patients may be treated using high-frequency (18 Hz) bilateral stimulation applied over the DLPFC, bilaterally, with deep TMS coils. Objective measures of improvement such as the Scale for the Assessment of Negative Symptoms and the Positive and Negative Syndrome Scales may be used to ensure the reliability of results. Resting-state functional connectivity MRI or rsFC MRI is an advanced imaging technique that provides functional connectivity (FC) of the brain that may be used according to embodiments described herein to measure the abnormalities of brain networks in schizophrenia.

Comparing schizophrenia patients with healthy controls, individuals with a clinical high risk for psychosis (CHR) and schizophrenia patients showed hypo-connectivity between posterior insula (PI) and somatosensory areas, and between dorsal anterior insula (dAI) and putamen. Furthermore, schizophrenia patients showed dAI and ventral anterior insula(vAI) hyper-connectivity with visual areas relative to controls and CHR individuals. FC has offered evidence for the dysconnectivity hypothesis of schizophrenia.

As resting-state fMRI (rsfMRI) can map functional brain networks, such as the default mode network (DMN), it makes the study of the systems-level pathology of schizophrenia possible. The connectivity of the DMN may be altered in patients with schizophrenia. Specifically, features discovered by rsfMRI may include: hyper-connectivity of the DMN is the common consensus of rsFC MRI studies; altered cortical-subcortical networks, including thalamocortical, frontolimbic, and cortico-cerebellar networks; reduced connectivity of the prefrontal cortex (PFC), particularly intra-PFC connectivity; patterns of functional connectivity within auditory/language networks and the basal ganglia correlate to specific clinical symptoms, including auditory-verbal hallucinations and delusions.

Embodiments described herein may use rsFC MRI and correlation analysis to identify targets for TMS treatment of schizophrenia. dAI functional connectivity with superior temporal gyms may positively correlate with positive symptoms of CHR. Furthermore, vAI connectivity with DLPFC may negatively correlate with the severity of the symptoms of first-episode schizophrenia. The methods described herein may give the capability of using rsFC MRI to map the whole-brain network topology and to use graph theory. Functional brain networks in schizophrenia may be characterized by reduced small-worldness, lower degree connectivity of brain hubs, and decreased modularity.

The sensitivity of functional connectivity is sufficient to detect differences in unaffected relatives, suggesting that functional dysconnectivity is an endophenotype related to genetic risk for schizophrenia. As we have broad support for dysconnectivity theories of schizophrenia, this feature of rsFC MRI may be used to identify targets for TMS treatment.

The methods described herein may be used to treat stroke and other brain lesions. There may be beneficial effects of repetitive transcranial magnetic stimulation (rTMS) on the left DLPFC for treating various neuropsychiatric or neuropsychological disorders.

In some embodiments, the disclosed method may target specific brain regions. For example, the default mode network (DMN), cognitive control network (CCN) and affective network (AN) may include a depression-related increase in functional connectivity (FC) in the same dorsal region (i.e., dorsal medial prefrontal) called the dorsal nexus. This result suggests that depressive symptoms are not associated with a specific network but rather the dysfunction of several brain networks. Further, PSD has been shown to cause changes in FC in DMN and AN. These networks may be involved in the pathogenesis of PSD.

Patients with first acute ischemic stroke onset were analyzed for the performance of a fMRI and found that the functional connectivity (FC) of the motor network in acute ischemic stroke is independently associated with functional outcomes. Specifically, the FC between ipsilesional primary motor cortex (M1) and contralesional dorsal premotor area (PMd), were independently associated with unfavorable outcomes, whereas the FC of the default mode network was not different between groups. These results showed that interhemispheric FC of the motor network is an independent predictor of functional outcomes in patients with acute ischemic stroke. High-frequency rTMS on the left DLPFC may enhance low-frequency resting-state brain activity in the target site and remote sites, as reflected by fALFF and FC. This way TMS may be used to reach remote sites affected by stroke.

Inversely, fMRI can be used to find the exact location of the cortical counterpart of the networks in which an inaccessible brain region has been affected by stroke. Embodiments described herein may comprise a complete brain assessment for determining target locations for TMS treatment. Embodiments described herein include the comparison of covariation of fMRI data between regions and networks of a patient's brain. Embodiments may include a complete assessment of these regions networks according to embodiments described herein. Embodiments may also provide focus to specific regions and networks based on the known associated functional connections in relation to a given condition, symptom, or illness. The focus may be to reduce the computations required in assessing the functional connectivity of the brain, and/or in providing particular attention, such as segmentation into smaller regions for more specific targeting of areas that are already believed to be beneficial for TMS treatment in relationship to a given symptom or disease. Such pre-knowledge of functional relationships as described herein may be used to determine the regions and/or region sizes of brain regions as described herein in making comparisons and assessments. Such pre-knowledge of functional relationships as described herein may be used to eliminate some comparisons and/or enlarge regions for comparisons for areas that are not of interest or not believed to be functionally related or relevant to the given symptom or disease.

The conventional TMS approach that is FDA approved uses the 5-cm rule for TMS targeting. This approach does not include any guidance through imaging, and is not personalized to account for variations of brain regions between individuals. Some attempts to use fMRI to guide TMS determine the most anticorrelated region of the DLPFC with the subgenual cingulate to detect a target for TMS stimulation for Depression. This approach focuses on only two specific regions of the brain with only a single relationship between these regions. Current embodiments described herein may include a more complete brain assessment to detect brain circuits including multiple targets for TMS and LIFUS. Embodiments may include an assessment of the entire brain as opposed to a specifically focused approach on the DLPFC. Cortical brain circuits may be selected for target stimulation with TMS. Subcortical brain circuits may be selected for targeted stimulation with LIFUS. Embodiments described herein may include a circuit-based approach that assesses multiple and interconnected brain regions for stimulation as opposed to the single region application on the DLPFC. Embodiments described herein may be used in depression, but also other brain injuries, such as TBIs or other brain lesions. Embodiments described herein identify and extract amplitude and frequency of brain activity within/between brain networks in order to analyze connectivity between circuits.

Specific brain conditions are shown and described herein with respect to functional connection analysis and the resulting likely regions of interest for target treatments for stimulation. Specific examples are provided herein, which are not intended to be limiting. Structural analysis may be added or used as described herein for any brain condition to find abnormalities and/or determine target locations for stimulation.

Total Cortical Gray Matter Volume and White Surface Total Area, in a prospective case series in neurodevelopmental disorders (such as Autism Spectrum Disorders) and neurodegenerative diseases (such as Dementias, Alzheimer's disease, etc.).

Tables 1-2 illustrate improvements of structural connectivity are provided here as examples of the success of the use of structural connectivity in analyzing neurodevelopmental conditions.

TABLE 1

| Total mm^3 | Cortical Grey Matter (before) | Cortical Grey Matter (after) | % change |
|---|---|---|---|
| P1 | 559513 | 563756 | 0.753 |
| P2 | 540735 | 549931 | 1.672 |
| P3 | 561866 | 569011 | 1.256 |
| P4 | 523163 | 527801 | 0.879 |
| P5 | 543242 | 552101 | 1.605 |
| mean | 542252 | 549711 | 1.35 |
| Sd | 15738.1 | 15938.3 | 0.41 |

TABLE 2

| Total mm^2 | White Surface Area (before) | White Matter Volume (after) | % change |
|---|---|---|---|
| P1 | 93033.3 | 95126.1 | 2.2 |
| P2 | 94151.8 | 96268.3 | 2.199 |
| P3 | 92178.6 | 94221.5 | 2.168 |
| P4 | 93173.8 | 95578.7 | 2.516 |
| P5 | 92227.1 | 95232.1 | 3.155 |
| Mean | 92932.8 | 95325.2 | 2.51 |
| Sd | 809.16 | 743.68 | 0.42 |

Table 1 provides a sample of five (5) patients with Autism Spectrum Disorder between the ages of 18 and 22 years old. All patients showed an increase in total cortical grey matter volume after completion of two months of fMRI-guided TMS treatment (5 times per week) when the method used structural connectivity. Individual and averaged measurements are displayed at baseline and after treatments. In healthy controls, the total cortical grey matter volume loss is about one (1) percent per year.

Table 2 provides a sample of five (5) patients with Autism spectrum Disorder between the ages of 18 and 22 years old. All patients showed an increase in white surface total area after completion of two month fMRI guided TMS treatments (5 treatments per week) using structural connectivity analysis according to embodiments described herein. Individual and averaged measurements are displayed at baseline and after treatments. In healthy children, the white surface total area generally increases over a three year interval (from nine years old to 12 years old) by 1.7%.

Tables 3-4 illustrate improvements of structural connectivity are provided here as examples of the success of the use of structural connectivity in analyzing neurodegenerative disorders.

TABLE 3

| Total mm^3 | Cortical Grey Matter (before) | Cortical Grey Matter (after) | % change |
|---|---|---|---|
| P1 | 559513 | 563756 | 0.753 |
| P2 | 540735 | 549931 | 1.672 |
| P3 | 561866 | 569011 | 1.256 |
| P4 | 523163 | 527801 | 0.879 |
| P5 | 543242 | 552101 | 1.605 |
| mean | 542252 | 549711 | 1.35 |
| Sd | 15738.1 | 15938.3 | 0.41 |

TABLE 4

| Total mm^2 | White Surface Area (before) | White Matter Volume (after) | % change |
|---|---|---|---|
| P1 | 93033.3 | 95126.1 | 2.2 |
| P2 | 94151.8 | 96268.3 | 2.199 |
| P3 | 92178.6 | 94221.5 | 2.168 |
| P4 | 93173.8 | 95578.7 | 2.516 |
| P5 | 92227.1 | 95232.1 | 3.155 |
| Mean | 92932.8 | 95325.2 | 2.51 |
| Sd | 809.16 | 743.68 | 0.42 |

Table 3 provides a sample of five patients with Dementias (Alzheimer's disease) of patients in the age range of 69 to 72 years old. All patients showed an increase in total cortical grey matter volume after completion of six month of fMRI guided TMS treatments of 5 weeks per week. Individual and averaged measurements are displayed at baseline and after treatments. Local gray matter loss rates (5.3 plus or minus 2.3% per year in AD verse 0.9 plus or minus 0.9 percent per year in controls.

Table 4 provides a sample of five (5) patients with Dementias (Alzheimer's disease) of a patient age range of 68 to 72 years old. All patients showed an increase in white surface total area after completion of six months of fMRI guided TMS treatments (at 5 times per week). Individual and averaged measurements are displayed at baseline and after treatment. In healthy individuals ranging from 30 to 90 years of age, a 26% reduction in white matter tissue volume has been observed, relative to a 14% reduction in gray matter tissue volume.

The computing devices described herein are non-conventional systems at least because of the use of non-conventional component parts and/or the use of non-conventional algorithms, processes, and methods embodied, at least partially, in the programming instructions stored and/or executed by the computing devices. For example, embodiments may use configurations of and processes involving a unique magnetic devices for administering magnetic fields to a patient according to methods and algorithms for specific treatment targeting as described herein, configurations of and processes involving a unique transcranial magnetic stimulation device or low frequency intensity focused ultrasound device with and without high precision navigation, unique processes and algorithms for determining specific brain circuits of a patient's brain that is personalized per patient, unique configurations and processes for targeting and placing the TMS for application to the specific brain circuits personalized per patient, or combinations thereof. The systems and methods described herein also include algorithms for identifying and extracting amplitude and frequency of brain activity within and between brain networks for precise and personalized TMS treatment. Embodiments may be used to identify target locations for TMS treatment of neurological and psychiatric conditions such as, without limitation, traumatic brain injury, brain lesions, psychoses, depression, maintenance. Autism, dementia, among others. Exemplar embodiments described herein may also or alternatively be used in prevention and not simply pathology, such as prevention of cognitive decline due to age. Embodiments may be used to improve the length of a treatment effect so that the beneficial therapeutic treatment effects may last longer. Embodiments may include combinations of functional connection and/or structural connection to determine target treatment areas that are personalized to the individual. The use of a combination of functional and/or structural connections may provide a more complete analysis of an individual's brain function based on the individual and/or the brain condition to find target locations for stimulation that are most likely to make improvements to a patient's condition.

Embodiments comprise a non-transitory computer-accessible medium having stored thereon computer-executable instructions for determining one or more target regions for transcranial magnetic stimulation (TMS) treatment of a patient, wherein the computer-executable instructions are configured when executed by one or more processors to perform a method. A method for determining one or more target regions for transcranial magnetic stimulation (TMS treatment of a patient may include steps for: receiving functional magnetic resonance imaging (fMRI) data of a head of the patient; analyzing functional connections of the patient's brain through analysis of the fMRI data by determining changes in any combination of a first fluctuation in amplitude of the fMRI imaging data, a second fluctuation in frequency of the fMRI data, or a third fluctuation in frequency relative to amplitude of the fMRI data; and determining one or more target regions for TMS treatment of the patient based on the determination of any combination of the first fluctuation, the second fluctuation, or the third fluctuation.

Embodiments of the non-transitory computer-accessible medium, instructions, or methods may include any combination of: comparing the determination of any combination of the first fluctuation, the second fluctuation, or the third fluctuation with measurements of a health control group matching an age range and gender of the patient.

Embodiments of the non-transitory computer-accessible medium, instructions, or methods may include the analyzing the functional connections of the patient's brain including the first fluctuation, second fluctuation, or third fluctuation, includes any combination of: determining activation, correlation, covariation, or a combination thereof matrices between different brain networks of the patient's brain; matrices between regions within a network of the patient's brain; matrices between regions within a network and all other regions of the network combined; matrices between different brain regions within a network and all other regions within the same network; and/or matrices between different brain regions of different networks.

The non-transitory computer-accessible medium, instructions, or methods may include any combination of: selecting a first plurality of brain regions having a low change in activation, correlation, covariation, or a combination thereof with a larger number of brain networks or regions; selecting a second plurality of brain regions having a high change in activation, correlation, covariation, or a combination thereof with a large number of brain networks or regions; comparing the first plurality of brain regions and the second plurality of brain regions with brain regions from a health control group matching an age range and gender of the patient, and/or selecting the brain regions above a first threshold value and below a second threshold value to create a potential target group of brain regions for TMS treatment.

The non-transitory computer-accessible medium, instructions, or methods may include the first threshold value within two standard deviations above a mean of the healthy control group, and the second threshold value is within two standard deviations below the mean of the healthy control group.

The non-transitory computer-accessible medium, instructions, or methods may include any combination of the potential target group of brain regions for TMS treatment is compared with a second control group matching the patient's symptoms, diagnosis, or a combination thereof, and determining a subset from the potential target group of brain regions by determining which of the regions has the greatest change in fMRI data from pre-TMS treatment to post-TMS treatment from the second control group; and/or administering TMS treatment to the patient based on at least one parameter from a treatment plan of a member from the second control group having a brain region of the greatest change in fMRI data from pre-TMS treatment to post-TMS treatment.

The non-transitory computer-accessible medium, instructions, or methods may include receiving diffusion-weighted magnetic resonance imaging (dMRI) data of a head of the patient; analyzing structural connections of the patient's brain through analysis of the dMRI data by comparing strength of a white matter connection between combinations of parcels within the patient's brain; wherein determining one or more target regions for TMS treatment of the patient is based on the analysis of structural connections. The non-transitory computer-accessible medium and/or methods may include determining one or more target regions comprises selecting target locations for stimulation with a higher number of white matter connections as compared to other potential targets.

The non-transitory computer-accessible medium, instructions, or methods may include the analysis of structural connections of the patient's brain is conducted after the analysis of functional connections and the determination of the one or more target regions are first determined based on the functional connections and then a final subset are selected using the analysis of structural connections.

The non-transitory computer-accessible medium, instructions, or methods may include performing functional connectivity analysis by: defining a plurality of brain networks of the patient and a plurality of brain regions of the patient; comprising comparing covariation between a brain network and each of another brain network of the plurality of brain networks for each of the plurality of brain networks of the patient, comparing covariation between a first brain region to each of another brain region within a same brain network as the first brain region for each of the plurality of brain regions, comparing covariation between a second brain region to each of another brain region within a different brain network as the second brain region for each of the plurality of brain regions, comparing covariation between a third brain region to each of another brain network different from the brain network in which the third brain region is contained for each of the plurality of brain regions; selecting a first set of regions in which a lowest change in covariation comparison occurs with a largest number of brain regions of the plurality of regions; selecting a second set of regions in which lowest change in covariation comparison occurs with a largest number of brain regions of the plurality of regions; comparing the first set of regions and the second set of regions with a healthy control group and determining a first set of potential targets from the first set of regions and the second set of regions that are outside of a determined normal range as compared to the healthy control group; and determine a target set of regions from the comparison of the first set of regions and the second set of regions with the healthy control groups.

The non-transitory computer-accessible medium, instructions, or methods may include determining one or more target regions for transcranial magnetic stimulation (TMS) treatment of a patient for treating a mental disorder, the method comprising: receiving functional magnetic resonance imaging (fMRI) data of a head of the patient; analyzing functional connections of the patient's brain through analysis of the fMRI data by determining changes in any combination of a first fluctuation in amplitude of the fMRI imaging data, a second fluctuation in frequency of the fMRI data, or a third fluctuation in frequency relative to amplitude of the fMRI data; determining one or more target regions for TMS treatment of the patient based on the determination of any combination of the first fluctuation, the second fluctuation, or the third fluctuation; applying TMS treatment at the one or more target regions; and improving a mental disorder of the patient.

The non-transitory computer-accessible medium, instructions, or methods may include the mental disorder being selected from Alzheimer's disease, anxiety, obsessive compulsive disorder, post-traumatic stress disorder, schizophrenia, insomnia, eating disorders, cognitive impairment, drug addiction, depression, attention deficit hyperactivity disorder, attention deficit disorder, bipolar disorder, autism spectrum disorder, neurodevelopmental disorders, and psychoses.

The non-transitory computer-accessible medium, instructions, or methods may include receiving diffusion-weighted magnetic resonance imaging (dMRI) data of a head of the patient; analyzing structural connections of the patient's brain through analysis of the dMRI data by comparing strength of a white matter connection between combinations of parcels within the patient's brain; determining one or more target regions for TMS treatment of the patient based on the analysis of structural connections.

The non-transitory computer-accessible medium, instructions, or methods may include receiving diffusion-weighted magnetic resonance imaging (dMRI) data of a head of the patient; analyzing the structural connection of the patient's brain through analysis of the dMRI data by generating a brain structural connectivity matrix constructed based on white matter tractography from the whole brain; and determining one or more target regions for TMS treatment of the patient based on the analysis of structural connections.

The non-transitory computer-accessible medium, instructions, or methods may include receiving fMRI data; construct covariation matrixes using the fMRI data; selecting a first set of potential targets with stronger covariation values with a first large group of brain regions, selecting a second set of potential targets with weaker covariation with a second large group of brain regions, or selecting a combination of the first set of potential targets and the second set of potential targets; receive dMRI data; use dMRI data to construct a structural connectivity matrix; select target regions from the first set of potential targets, the second set of potential targets, or the first and second set of potential targets with a higher number of white matter connections.

The non-transitory computer-accessible medium, instructions, or methods may include receiving fMRI data; construct covariation matrixes using the fMRI data; selecting a first set of potential targets with stronger covariation values with a first large group of brain regions, selecting a second set of potential targets with weaker covariation with a second large group of brain regions, or selecting a combination of the first set of potential targets and the second set of potential targets; receive dMRI data; use dMRI data to construct a structural connectivity matrix; select target regions from the first set of potential targets, the second set of potential targets, or the first and second set of potential targets with a higher number of white matter connections.

The non-transitory computer-accessible medium, instructions, or methods may include receive dMRI data; use dMRI data to construct a structural connectivity matrix; select a set of potential targets with a lower number of white matter connections; receiving fMRI data; construct covariation matrixes using the fMRI data; selecting a first set of targets from the set of potential targets with stronger covariation values with a first large group of brain regions, selecting a second set of targets from the set of potential targets with weaker covariation with a second large group of brain regions, or selecting a combination of the first set of targets and the second set of targets.

The non-transitory computer-accessible medium, instructions, or methods may include the structural data comprising T1w/T2w is used to construct the structural connectivity matrix.

The system described herein can be based in software and/or hardware. While some specific embodiments of the invention have been shown the invention is not to be limited to these embodiments. For example, most functions performed by electronic hardware components may be duplicated by software emulation. Thus, a software program written to accomplish those same functions may emulate the functionality of the hardware components in input-output circuitry. The invention is to be understood as not limited by the specific embodiments described herein, but only by scope of the appended claims.

Although embodiments of this invention have been fully described with reference to the accompanying drawings, various changes and modifications will be apparent to those skilled in the art. Such changes and modifications are to be understood as being included within the scope of embodiments of this disclosure as defined by the appended claims. Any of the disclosed components may be used in any combination. For example, any component, feature, step or part may be integrated, separated, sub-divided, removed, duplicated, added, or used in any combination and remain within the scope of the present disclosure. Embodiments are exemplary only, and provide an illustrative combination of features, but are not limited thereto.

The foregoing merely illustrates the principles of the disclosure. Any examples set forth in this specification are not intended to be limiting and merely set forth some of the many possible embodiments for the appended claims. Those skilled in the art will readily recognize various modifications and changes that may be made without following the example embodiments and applications illustrated and described herein, and without departing from the true spirit and scope of the following claims.

All references cited and/or discussed in this specification are incorporated herein by reference in their entireties and to the same extent as if each reference was individually incorporated by reference.

What is claimed is:

1. A non-transitory computer-accessible medium having stored thereon computer-executable instructions for determining one or more target regions for transcranial magnetic stimulation (TMS) treatment of a patient, wherein the computer-executable instructions are configured when executed by one or more processors to perform a method, comprising:
receiving functional magnetic resonance imaging (fMRI) data of a head of the patient;
analyzing functional connections of the patient's brain through analysis of the fMRI data by determining changes in any combination of a first fluctuation in amplitude of the fMRI imaging data, a second fluctuation in frequency of the fMRI data, or a third fluctuation in frequency relative to amplitude of the fMRI data;

selecting a first plurality of brain regions having a change in activation, correlation, covariation, or a combination thereof with a larger number of brain networks or regions that is lower than that of other brain regions;

selecting a second plurality of brain regions having a change in activation, correlation, covariation, or a combination thereof with a larger number of brain networks or regions that is higher than that of other brain regions;

determining one or more target regions for TMS treatment of the patient based on the determination of changes in any combination of the first fluctuation, the second fluctuation, or the third fluctuation by comparing the first plurality of brain regions and the second plurality of brain regions with corresponding brain regions from a healthy control group matching an age range and gender of the patient, and selecting a potential target group of brain regions above a first threshold value and below a second threshold value; and causing TMS treatment to be administered to the patient at the one or more target regions selected from the potential target group of brain regions.

2. The non-transitory computer-accessible medium of claim 1, wherein the computer-executable instructions are further configured to perform: comparing the determination of changes in any combination of the first fluctuation, the second fluctuation, or the third fluctuation with measurements of a healthy control group matching an age range and gender of the patient.

3. The non-transitory computer-accessible medium of claim 1, wherein the analyzing the functional connections of the patient's brain including the first fluctuation, second fluctuation, or third fluctuation, includes determining matrices of activation, correlation, covariation, or a combination thereof between different brain networks of the patient's brain.

4. The non-transitory computer-accessible medium of claim 1, wherein the analyzing the functional connections of the patient's brain including the first fluctuation, second fluctuation, or third fluctuation, includes determining matrices of activation, correlation, covariation, or a combination thereof between regions within a network of the patient's brain.

5. The non-transitory computer-accessible medium of claim 1, wherein the analyzing the functional connections of the patient's brain including the first fluctuation, second fluctuation, or third fluctuation, includes determining matrices of activation, correlation, covariation, or a combination thereof between regions within a network and all other regions of the network combined.

6. The non-transitory computer-accessible medium of claim 1, wherein the analyzing the functional connections of the patient's brain including the first fluctuation, second fluctuation, or third fluctuation, includes determining matrices of activation, correlation, covariation, or a combination thereof between different brain regions within a network and all other regions within the same network.

7. The non-transitory computer-accessible medium of claim 1, wherein the analyzing the functional connections of the patient's brain including the first fluctuation, second fluctuation, or third fluctuation, includes determining the matrices of activation, correlation, covariation, or a combination thereof between different brain regions of different networks.

8. The non-transitory computer-accessible medium of claim 1, wherein the first threshold value is within two standard deviations above a mean of the healthy control group, and the second threshold value is within two standard deviations below the mean of the healthy control group.

9. The non-transitory computer-accessible medium of claim 1, wherein the potential target group of brain regions for TMS treatment is compared with a second control group matching the patient's symptoms, diagnosis, or a combination thereof, and determining a subset from the potential target group of brain regions that have a greatest change in fMRI data from pre-TMS treatment to post-TMS treatment from the second control group.

10. The non-transitory computer-accessible medium of claim 1, wherein the computer-executable instructions are further configured to perform: causing TMS treatment to be administered to the patient based on at least one parameter from a treatment plan of a member from the second control group having a brain region of the greatest change in fMRI data from pre-TMS treatment to post-TMS treatment.

11. The non-transitory computer-accessible medium of claim 1, wherein the computer-executable instructions are further configured to perform:
receiving diffusion magnetic resonance imaging (dMRI) data of the head of the patient;
analyzing structural connections of the patient's brain through analysis of the dMRI data by comparing strength of a white matter connection between combinations of parcels within the patient's brain;
wherein determining one or more target regions for TMS treatment of the patient is based on the analysis of structural connections.

12. The non-transitory computer-accessible medium of claim 11, wherein the determining one or more target regions comprises selecting target locations for stimulation with a higher number of white matter connections as compared to other potential targets.

13. The non-transitory computer-accessible medium of claim 12, wherein the analysis of structural connections of the patient's brain is conducted after the analysis of functional connections and the determination of the one or more target regions is first determined based on the functional connections and then a final subset is selected using the analysis of structural connections.

14. A method of treating a patient using transcranial magnetic stimulation (TMS) treatment, comprising:
determining one or more target regions for stimulation using the non-transitory computer-accessible medium of claim 1; and
stimulating the patient using TMS at the one or more target regions.

* * * * *